(12) United States Patent
Novosselov et al.

(10) Patent No.: US 8,561,486 B2
(45) Date of Patent: Oct. 22, 2013

(54) PARTICLE INTERROGATION DEVICES AND METHODS

(75) Inventors: Igor V Novosselov, Seattle, WA (US); Peter C Ariessohn, Lake Tapps, WA (US); Evan D Dengler, Seattle, WA (US); Michelle Hickner, Seattle, WA (US)

(73) Assignee: Enertechnix, Inc, Maple Valley, WA (US)

( * ) Notice: Subject to any disclaimer, the term of this patent is extended or adjusted under 35 U.S.C. 154(b) by 403 days.

(21) Appl. No.: 13/078,999

(22) Filed: Apr. 3, 2011

(65) Prior Publication Data

US 2011/0186436 A1    Aug. 4, 2011

Related U.S. Application Data

(63) Continuation-in-part of application No. 12/834,860, filed on Jul. 12, 2010, now Pat. No. 8,307,723.

(60) Provisional application No. 61/225,007, filed on Jul. 13, 2009, provisional application No. 61/318,313, filed on Mar. 27, 2010.

(51) Int. Cl.
   *G01N 1/12*    (2006.01)

(52) U.S. Cl.
   USPC ...................................................... 73/864.32

(58) Field of Classification Search
   USPC ............................... 73/864, 864.32; 250/288
   See application file for complete search history.

(56) References Cited

U.S. PATENT DOCUMENTS

| | | | |
|---|---|---|---|
| 3,970,428 A | 7/1976 | Barringer |
| 4,580,440 A | 4/1986 | Reid |
| 4,819,477 A | 4/1989 | Fisher |
| 4,909,090 A | 3/1990 | McGown |

(Continued)

FOREIGN PATENT DOCUMENTS

| WO | 2008049038 | 4/2008 |
|---|---|---|
| WO | 2010095123 | 8/2010 |

OTHER PUBLICATIONS

Conrad, FJ et al. 1979. Selection of a gas chromatographic material for use in explosives vapor preconcentration. J Chromatography 176:37-41.

(Continued)

*Primary Examiner* — Hezron E Williams
*Assistant Examiner* — Rodney T Frank
(74) *Attorney, Agent, or Firm* — K Karel Lambert; Lambert Patent Services LLC

(57) ABSTRACT

Devices, apparatus and methods are disclosed for non-contact pneumatic sampling and sampling of surfaces, persons, articles of clothing, buildings, furnishings, vehicles, baggage, packages, mail, and the like, for contaminating aerosols indicative of a hazard or a benefit, where the contaminating aerosols are chemical, radiological, biological, toxic, or infectious in character. In a first device, a central orifice for pulling a suction gas stream is surrounded by a peripheral array of convergingly-directed gas jets, forming a virtual sampling chamber. The gas jets are configured to deliver millisecond pneumatic pulses that erode particles from solid surfaces at a distance. In another aspect of the invention, a suction gas stream is split using an air-to-air concentrator so that a particle-enriched gas flow is directed to a particle trap and any particles immobilized in the particle trap (including any adsorbed vapors associated with the particles) are selectively analyzed to detect trace residues associated with explosives.

20 Claims, 36 Drawing Sheets

(56) References Cited

U.S. PATENT DOCUMENTS

| | | |
|---|---|---|
| 5,092,218 A | 3/1992 | Fine |
| 5,123,274 A | 6/1992 | Carroll |
| 5,395,589 A | 3/1995 | Nacson |
| 5,425,263 A | 6/1995 | Davies |
| 5,465,607 A | 11/1995 | Corrigan |
| 5,565,677 A | 10/1996 | Wexler |
| 5,675,070 A | 10/1997 | Gelperin |
| 5,854,431 A | 12/1998 | Linker |
| 6,073,499 A | 6/2000 | Settles |
| 6,156,212 A | 12/2000 | Rader |
| 6,324,927 B1 | 12/2001 | Ornath |
| 6,334,365 B1 * | 1/2002 | Linker et al. ............... 73/864.81 |
| 6,345,545 B1 | 2/2002 | Linker |
| 6,523,393 B1 | 2/2003 | Linker |
| 6,604,406 B1 | 8/2003 | Linker |
| 6,664,550 B2 | 12/2003 | Rader |
| 6,828,795 B2 | 12/2004 | Krasnobaev |
| 6,848,325 B2 | 2/2005 | Parmeter |
| 6,870,155 B2 * | 3/2005 | Krasnobaev et al. ......... 250/283 |
| 6,887,710 B2 | 5/2005 | Call |
| 6,906,322 B2 | 6/2005 | Berggren |
| RE38,797 E | 9/2005 | Linker |
| 6,972,408 B1 | 12/2005 | Reilly |
| 7,141,786 B2 | 11/2006 | McGann |
| 7,208,122 B2 | 4/2007 | Swager |
| 7,256,396 B2 | 8/2007 | Reilly |
| 7,260,483 B2 | 8/2007 | Gard |
| 7,275,453 B2 | 10/2007 | Ishikawa |
| 7,299,710 B2 | 11/2007 | Syage |
| 7,574,930 B2 * | 8/2009 | Bunker ...................... 73/864.33 |
| 7,605,367 B2 | 10/2009 | Miller |
| 7,997,119 B2 * | 8/2011 | Wu ............................. 73/31.03 |
| 8,113,069 B2 * | 2/2012 | Settles ...................... 73/864.35 |
| 2006/0102837 A1 | 5/2006 | Wang |
| 2007/0158447 A1 * | 7/2007 | Bunker ........................... 239/1 |
| 2009/0084201 A1 * | 4/2009 | Almirall et al. ........... 73/864.81 |
| 2010/0252731 A1 | 10/2010 | Reilly |

OTHER PUBLICATIONS

Moore, DS. 2009. Recent advances in trace explosives detection instrumentation. Sens Imaging 8:9-38.

* cited by examiner

300a

300b

300c

Table I. Vapor Pressures of Selected Analytes

| Analyte | VP [ppt] |
|---|---|
| EGDN | 5.00E+08 |
| DMDNB | 2.70E+06 |
| NG | 5.80E+05 |
| TNT | 9.50E+03 |
| PETN | 18 |
| RDX | 6 |

| Table 2. | PARTICLE CAPTURE | | VAPOR CAPTURE | |
|---|---|---|---|---|
| | Volatiles | Liq. Eluate | Volatiles | Liq. Eluate |
| RDX | + | + | - | - |
| PETN | + | + | - | - |
| TATP | ± | + | - | - |
| TNT | + | + | ± | np |
| APNC | + | + | - | np |
| NG | + | + | + | np |
| DMDNB | + | + | + | np |
| EGDN | ± | + | + | np |
| 2-EH | ± | ± | + | np |
| CXO | ± | ± | + | np |
| DAOH | ± | ± | + | np |
| FUEL OIL | + | + | + | np |
| GUNPOWDER | - | + | - | - |

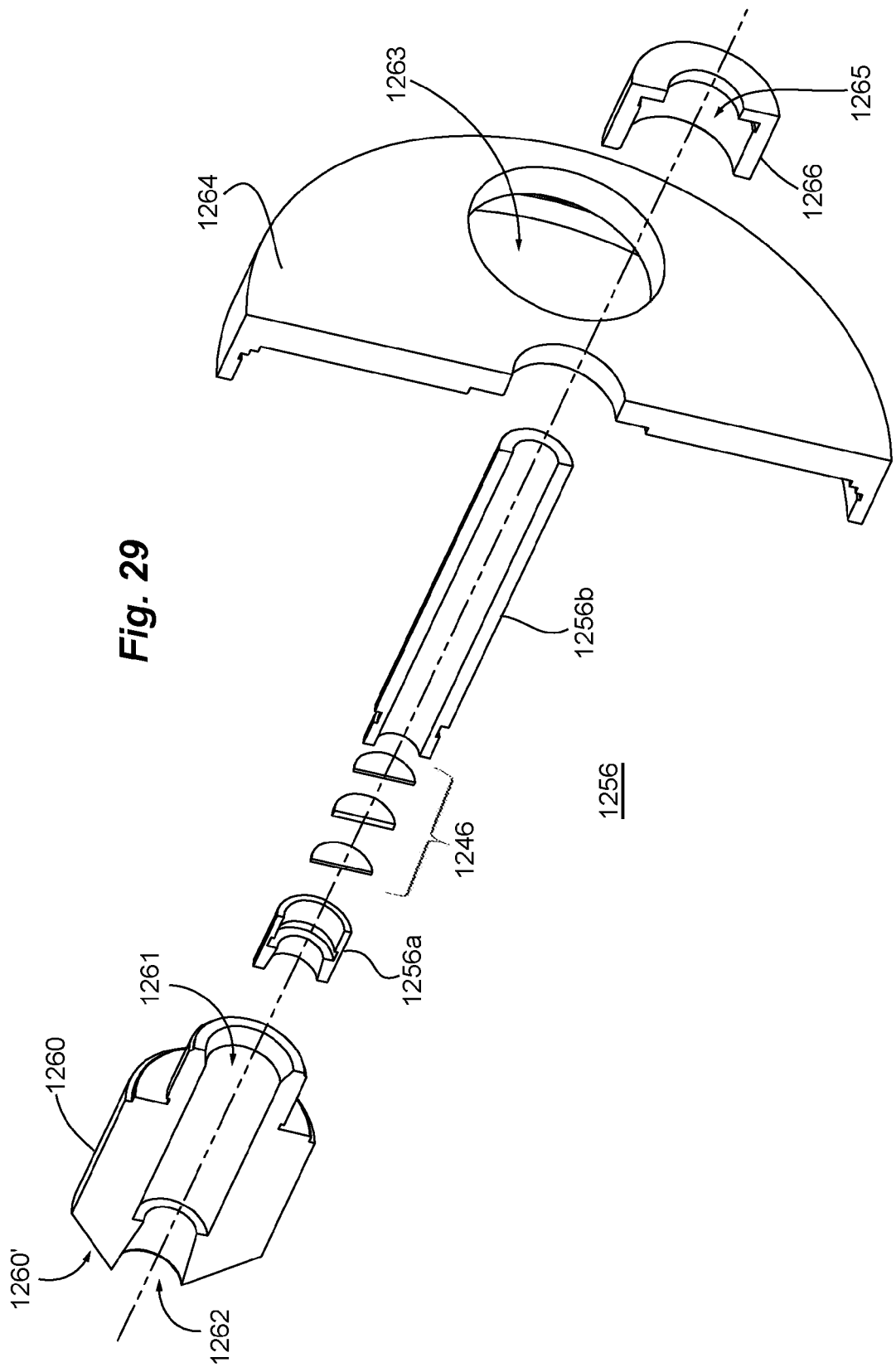

PARTICLE INTERROGATION DEVICES AND METHODS

CROSS-REFERENCE TO RELATED APPLICATIONS

This application is a continuation-in-part of U.S. patent application Ser. No. 12/834,860, filed 12 Jul. 2010, which claims the benefit of priority under 35 U.S.C. §119(e) from U.S. Provisional Patent Application No. 61/318,313 filed Mar. 27, 2010 and from U.S. Provisional Patent Application No. 61/225,007 filed Jul. 13, 2009; said patent documents being incorporated herein in entirety for all purposes by reference.

GOVERNMENT SUPPORT

The United States Government may have certain rights in this invention pursuant to Grant Nos. HSHQDC-08-C-00076 and HSHQDC-09-C-00131 awarded by the Department of Homeland Security.

FIELD AND BACKGROUND OF THE INVENTION

The invention relates to sampling and concentrative apparatus and methods for collection of trace analytes from surfaces and substrates where the analyte is in the form of a particulate or a vapor adherent to a particulate and particularly to such apparatus and methods as are useful in surveillance for trace explosives residues.

There is a need for inspection and sampling of persons, articles of clothing, buildings, furnishings, vehicles, baggage, cargo containers, dumpsters, packages, mail, and the like for contaminating residues (termed here more generally "trace analytes") that may indicate chemical, radiological, biological, illicit, or infectious hazards. Applications involve detection of trace materials, both particles and optionally vapors, associated with persons who have handled explosives, detection of toxins in mail, or detection of spores on surfaces, while not limited thereto.

Current methods for surface sampling often involve contacting use of swabs or liquids, but methods for sampling by "sniffing" are preferred. To inspect mail or luggage for example, the sampling method of U.S. Pat. No. 6,887,710 involves first placing the article or articles in a box-like enclosure equipped with airlocks, directing a blast of air onto the exposed surfaces in order to dislodge particles associated with the articles, then sampling the gaseous contents of the box by drawing any resulting aerosol through a sampling port. However, the process is inherently slow because each article or person must be moved into the box or chamber and the box sealed before sampling, an obvious disadvantage when large numbers of articles or persons must be screened, or when the articles are larger than can be reasonably enclosed, such as a truck, shipping container, or the hallway surfaces of a building. Similar comments may be made regarding the teachings of U.S. Pat. No. 6,324,927 to Ornath, where an enclosed shaker is used to dislodge particles.

An approach for sampling persons is seen in U.S. Pat. No. 6,073,499 to Settles, aspects of which are also discussed in "Sniffers: fluid dynamic sampling for olfactory trace detection in nature and homeland security", J Fluids Eng 127:189-218.

McGown in U.S. Pat. No. 4,909,090 describes a hand-held vapor sampler, optionally with a shroud for enclosing a sampling space, for using low pressure puffs of hot air to vaporize illicit substances on surfaces and trap any vapors on a collector coil. The coil contains ribbon-like windings of metal which have a thin coating of material such as an organic polymer effective in absorbing organic molecules such as cocaine. However, particles are not sampled and would not be successfully aspirated under the conditions described, which relies on a 250 Watt lamp and a spring-actuated plunger for generating a puff of air. Improvements to the collector/desorber device are disclosed in U.S. Pat. No. 5,123,274 to Carroll.

Ishikawa in U.S. Pat. No. 7,275,453 discloses a cover enclosure in contact with a surface, the enclosure with internally directed jet for operatively flushing and ejecting particles from the surface. The particles may be collected by means of an inertial impactor and thermally gasified from the impactor for detection of chemical constituents by mass spectroscopy. Use of a plate-type inertial impactor avoids the need for a fine-mesh filter, such as would become clogged.

Various particle and vapor traps are disclosed in patents to Linker of Sandia Labs, including U.S. RE38,797 and U.S. Pat. Nos. 7,299,711, 6,978,657, 6,604,406, 6,523,393, 6,345,545, 6,085,601 and 5,854,431, by Corrigan in U.S. Pat. Nos. 5,465,607 and 4,987,767, and Syage in U.S. Pat. No. 7,299,710, but implementation has proved difficult because particles have been found to poison commonly used vapor trap materials and means for efficiently separating particles and vapors are not recognized.

Teachings by Hitachi in U.S. Pat. No. 7,275,453 relate to an unusual inertial impactor with central void for discarding particles in excess of the cut size of the impactor. This has the unfortunate effect of dramatically reducing the amount of analyte available for detection. Also disclosed is a heatable rotary trap, as has longstandingly been used in the art.

Detection technologies are known. Of particular interest for detection of explosives are electron capture (often combined with gas chromatography), ion mobility spectroscopy, mass spectroscopy and chemiluminescence (often combined with gas chromatography).

One common analytical instrument for detection of nitrate-type explosives relies on pyrolysis followed by redox (electron capture) detection of $NO_2$ groups (Scientrex EVD 3000), but is prone to false alarms. Also of interest is differential mobility spectroscopy as described in U.S. Pat. No. 7,605,367 to Miller. Ion mobility spectroscopic (IMS) detectors are in widespread use and typically have picogram sensitivity. IMS requires ionization of the sample, which is typically accomplished by a radioactive source such as Nickel-63 or Americium-241. This technology is found in most commercially available explosive detectors like the GE VaporTracer (GESecurity, Bradenton, Fla.), Sabre 4000 (Smiths Detection, Herts, UK), Barringer IonScan™ 400, and Russian built models.

The luminescence of certain compounds undergoing reaction with electron-rich explosive vapors has been improved with the introduction of amplifying fluorescent polymers as described in U.S. Pat. No. 7,208,122 to Swager (ICx Technologies, Arlington Va.). Typically vapors are introduced into a tubular sensor lined with a conductive quenchable fluorescent polymer by suction. These sensors lack a pre-concentrator and work only for analytes with electron-donating properties. More recent advances have extended work with fluorescent polymers to include boronic peroxide-induced fluorescence, as is useful for detecting certain classes of explosives.

Other analytical modalities are available, and include the MDS Sciex CONDOR, Thermedics EGIS, Ion Track Instruments Model 97, the Sandia Microhound, Smith's Detection Cyranose, FIDO® (FLIR Systems, Arlington Va., formerly ICx Technologies), Gelperin's e-nose (U.S. Pat. No. 5,675,070), Implant Sciences' Quantum Sniffer, and others. However, these technologies are associated with aspiration and analysis of vapors, which are typically in vanishingly small concentrations, either because a) the vapor pressure of the material is inherently small, or b) if vapor pressure is larger, then significant quantities of a more volatile analyte will have been lost due to ageing of the material prior to sampling. Some of these detectors also have had maintenance issues, often related to fouling due to aspiration of particles.

Aerodynamic focusing has been used to produce particle beams or ribbons in a gas stream, process in which the gas streamlines are separated into a particle-depleted sheath flow and a particle-enriched flow. The two flows can then be separated, resulting in particle concentration. An aerodynamic lens particle concentration system typically consists of four parts: a flow control orifice, at least one focusing lenses, an acceleration nozzle, and a skimmer. The choked inlet orifice fixes the mass flow rate through the system and reduces pressure from ambient to the value required to achieve aerodynamic focusing. The focusing lenses are a series of orifices contained in a tube that create a converging-diverging path resulting in flow accelerations and decelerations, through which particles are separated from the carrier gas due to their inertia and focused into a tight particle beam or ribbon. The accelerating nozzle controls the operating pressure within the lens assembly and accelerates particles to downstream destinations. The skimmer is typically a virtual impactor with virtual impactor void for collecting the particle beam or ribbon while diverting the greater mass of the particle-depleted bulk flow, thus concentrating the particle fraction.

Focusing of a range of micron and submicron size aerosol particles has been carried out using aerodynamic forces in periodic aerodynamic lens arrays [see Liu et al, 1995, Generating particle beams of controlled dimensions and divergence, Aerosol Sci. Techn., 22:293-313, Wang, X et al, 2005, A design tool for aerodynamic lens system, Aerosol Sci Techn 39:624-636; US Pat. Appl. Doc. 2006/0102837 to Wang]. Such arrays may be used as inlets to on-line single-particle analyzers [see Wexler and Johnston (2001) in Aerosol Measurement: Principles, Techniques, and Applications, Baron and Willeke eds, Wiley, New York, and U.S. Pat. No. 5,565,677 to Wexler]. As known in the art, a major class of skimmers generally comprise a cone or plate with a hole in the center (i.e., are virtual impactors).

Aerodynamic lenses have been used in particle mass spectrometers and as an adjunct to ion mobility spectroscopy, (for example as described in U.S. Pat. Nos. 7,256,396, 7,260,483, and 6,972,408 and more recently in US Pat. 2010/0252731), where high vacuum is used (0.1 to 30 mTorr). In this system, analyte vapors released from a very well collimated particle beam (typically <0.25 mm diameter) are laser ablated and ionized in flight and the resulting vapors are conveyed in a buffer gas at high vacuum, typically with Einzel lensing, to a mass spectrometer or an ion mobility spectrometer. The downstream analyzer can be badly damaged by the entry of intact particles. Moreover, the particle-by-particle approach taught in the art substantially limits application for high throughput analysis and is not scaleable except by an impractical redundancy of parallel systems.

Related systems are described in PCT Publication WO/2008/049038 to Prather, U.S. Pat. No. 6,906,322 to Berggren, and U.S. Pat. No. 6,664,550 to Rader. However, these devices are readily overloaded when confronted with large amounts of complex mixtures, interferents, and dust, such as are likely to be encountered in routine use.

Thus, strategies are needed to improve analyte collection efficiency and avoid interferences. There is a need for a front end device with directional head for mobilization of particles from substrate to aerosol, a head that can be portably directed to dislodge particles and optionally vapor residues from target surfaces, then efficiently capture and concentrate them before presentation to an analytical instrument of choice, an approach that optimizes sensitivity and can speed deployment because the need to enclose the target surface in a sealed chamber or shroud is overcome. In particular, there is a need for a front end collection system that may be used in environments where a small amount of a target analyte must be detected in the presence of larger amounts of ubiquitous background particulates, for example dust and water with small amounts of target analyte, and with means for regenerating capture surfaces.

The preferred devices, systems and methods overcome the above disadvantages and limitations and are useful in detecting hazardous particles, vapors and volatiles associated with objects, structures, surfaces, cavities, vehicles or persons.

SUMMARY

Disclosed is a pneumatic sampler head with "virtual sampling chamber" for sampling hazardous contaminants such as traces of explosives, infectious agents, or toxins on persons, articles of clothing, buildings, furnishings, vehicles, cavities, dumpsters, cargo containers, baggage, packages, mail, and the like.

A first system includes a sampler head with a central collection intake operated under suction and an array of jet nozzles directed convergingly toward the apex of a virtual cone extending from the sampler head. A virtual sampling chamber is formed when streamlines of gas discharged by the jet nozzle array impinge on an external surface. The jets serve to dislodge and mobilize particulate and vapor residues on a surface and the suction intake draws them into the sampler head. Use of the jet-enclosed virtual sampling chamber extends and directs the reach of the suction intake, which would otherwise draw air from behind the intake.

Surprisingly, gas jets operated in a millisecond-scale pulse mode are found to be more effective than gas jets operated continuously in collecting particulate and/or vapor residues with the sampler head. The virtual sampling chamber may be formed and collapsed in less than a second in response to a single synchronized jet pulse while under suction, or may be formed intermittently, such as by a train of synchronized pulses separated by a fraction of a second or longer, during operation. The sampler head may be compact for portable hand-directed operation or scaled up and operated robotically for screening of vehicles, cargo containers, and so forth, while not limited thereto.

In one sampling system, the device is a pneumatic sampler head for sampling residues, including particulate and vapor residues, from an external surface of an object, structure, vehicle or person, which comprises a) a sampler head with forward face and perimeter; b) a suction intake port disposed centrally on the forward face and an array of two or more jet nozzles peripherally disposed on the forward face around the suction intake port, wherein the jet nozzles are directed at a virtual apex of a virtual cone with base resting on the forward face; c) a positive pressure source for firing or propelling a gas sampling jet pulse or stream with streamlines from each nozzle of the array of jet nozzles; d) a suction pressure source for drawing a sampling return stream of gas into the suction intake port, the suction pressure source having an inlet and an outlet; where the streamlines of the gas sampling jet pulses are directed toward the virtual apex of the virtual cone, the streamlines tracing an involuted frustroconical "U-turn" under the attraction of the suction pressure source and converging with the sampling return stream at the suction intake port along a central axis of the virtual cone when impinging on the external surface.

The out-flow of the gas sampling jets and in-flow of the sampling return stream form a "virtual sampling chamber" with the gas sampling jet pulses directed linearly along the walls of the virtual cone toward its apex and the sampling return stream directed along the central axis of the virtual cone toward its base, and further wherein the involuted frustroconical "U" fluidly connects the gas sampling jets and the sampling return stream at a virtual frustrum when impinging on an external surface. In preferred embodiments the device is operative at up to 1 foot from the external surface.

Surprisingly, we have found that pneumatic pulses or streams emitted from a concentric array of gas interrogation jet nozzles directed in trajectories along the walls of a virtual cone will turn inward when directed at a surface and return to a common suction intake port mounted in the sampler head in the center of the jet array. The sampler head may be held at a distance and aimed at the surface to be interrogated. Targetable jet nozzles and laser guidance may be used to shape the pulse geometry if desired. Particles or vapors removed from the interrogated surface are efficiently mobilized in the "virtual sampling chamber" and aspirated through the suction intake, where they may then be concentrated and analyzed by a variety of methods.

In use, pneumatic pulses initially follow directional vectors converging along the virtual "walls" of a "virtual cone", but upon contact with a surface disposed at a distance from the base of the cone $D_f$ which is less than the height of the cone $D_c$, a virtual frustrum is formed by involution of the streamline vectors so that the streamlines flow back along the central axis of the cone into an intake duct centrally mounted on the face of the sampler head. The virtual cone thus becomes a closed "virtual sampling chamber" where objects or surfaces brought within the cone are stripped of volatiles and loose particulates and carried into the sampler head. Once entrained in the suction intake, particles or vapors in the stream of air may be concentrated for collection or analysis.

Sampling jet and suction intake gas flows may be discontinuous or continuous, balanced or imbalanced, subsonic or sonic in character. In one application, the in-flows and out-flows from the sampler head are equal and opposite and form a closed loop, so that vapors or particles not trapped in the sampler head are recirculated and accumulate in the loop. In a preferred embodiment, the jet pulse out-flow is powered by an independent pressure source and is exceeded by the suction in-flow to achieve a net positive sampling, such as when a millisecond sampling pulse out-flow is followed by a suction in-flow of longer duration to ensure that the sampled air volume is greater than volume of the pulsed air jet:

$$V_{(SUCTION)} > V_{(JET\ PULSE)}$$

In practice, it has proved useful to operate the gas jets in single pulse mode or pulse train mode while under continuous or semi-continuous suction. In single pulse mode, the gas jets fire as a short burst after first activating the suction intake. In pulse train mode, a series of short bursts are emitted from the gas jets while operating the suction intake. A surface, substrate or object may be sampled with a single pulse or with a series of pulses. The sampler head may be moved or stationary between pulses, or a series of pulses may be emitted while the sampler head is moving and suction is engaged.

In another sampling system, the array of interrogation jet nozzles is surrounded by a perimeter of circumferential slits that emit a curtain wall of lower velocity gas forming a virtual shroud, skirt or apron around the virtual cone of the higher velocity convergent jets. This air is conveniently supplied by the exhaust of the suction intake. The exhaust of a blower used to power the suction intake, for example, may also be used to provide the gas flow for the curtain wall.

In yet another aspect, the invention is a method for sampling a residue from an exterior surface of an object, structure or person, which comprises contacting a virtual sampling chamber as described herein with an exterior surface at a distance less than the height $D_c$ of the virtual cone, whereby residues dislodged from the external surface by the gas jets are swept into a sampling return stream by the suction intake. The virtual sampling chamber may be employed intermittently with triggering, or cyclically, or continuously, but is preferentially pulsed with a pulse interval selected so that the jet pulse volume may efficiently be aspirated before firing a second pulse.

In a preferred aspect, one approach to a pneumatic sampler head combines biomimetic "sniffing" and interrogation jets for aerosolizing particles and optionally vapors, the combination serving as an efficient front end particle and/or vapor residue concentrator and capture device for use with a variety of analytical tools and instruments.

With respect to explosives surveillance and detection, the invention is an apparatus for concentration and collection of samples of explosives and explosives-associated particulate materials for analysis. The apparatus comprises a) a sampler head with directional nose, the nose having an intake port and upstream channel for receiving a first sample as a suction gas flow having a volume and a velocity and conveying the suction gas flow to an air-to-air particle concentrator, the air-to-air particle concentrator for accelerating and inertially dividing the suction gas flow according to a flow split into a particle-enriched flow in a first downstream channel and a bulk flow in a second downstream channel; b) a particle trap disposed in the first downstream channel for immobilizingly accumulating particles from the particle-enriched flow; c) a means for stripping a constituent or constituents of the accumulated particles and optionally for analyzing or detecting an explosive or explosive-associated residue therein.

Systems having on-board means for analyzing particle constituents are termed "fully integrated systems" and may be differentiated from systems for interfacing with remote analytical instrumentation, for example those systems where an insertable cartridge containing the sample is conveyed to a stand-alone analytical instrument for analysis. Integrated systems include those having detectors coupled to the particle trap by hydraulic or pneumatic coupling means and systems with particle traps having "in situ detection" capability, i.e., those having a detector operative for detecting analytes within the particle trap.

The particle trap may be a pervious screen, a centrifugal impactor, a bluff body impactor, or other impactor. The pervious screen may be selected from a ceramic filter or mesh, a glass filter or mesh, a plastic filter or mesh, or a metal filter or mesh.

The air-to-air particle concentrator may be an aerodynamic lens with skimmer, an inlet particle separator with splitter, a vortex particle separator with particle diverter, or an elutriative particle separator with particle diverter. The air-to-air concentrator preferably includes at least one aerodynamic lens or lens array disposed in the upstream channel and fluidly connected to the skimmer. The skimmer typically includes an inlet for receiving a particle beam or ribbon from the aerodynamic lens element, and splits the gas stream so that a bulk flow is diverted to a lateral flow channel and a particle-enriched flow is directed to a collector duct for particle capture and analysis. The skimmer is provided with a skimmer body, a skimmer nose, a lateral flow channel for receiving the bulk flow, and a virtual impactor mouth in fluid communication with a collector duct for receiving the particle-enriched flow. A particle trap is disposed in the collector duct. The particle trap has a trap hollow volume proportionate to its preconcentration factor.

The particle trap is typically mounted proximate to and downstream from the skimmer in the collector duct, and is preferably incorporated in the skimmer body. The skimmer body and particle trap optionally can be heated or cooled on command. Variations are possible within the scope of the invention. For example, the particle trap may be an insertable cartridge that is inserted either along (i.e., co-axial with) or across (i.e., transaxially to) the collector duct. In another instance, the particle trap may be mounted in a passage through a cylindrical body resembling a stopcock, rotation of which alternates the passage from a first position fluidly confluent with a gas flow in the collector duct and a second position fluidly confluent with a smaller-bore injection duct, the injection duct for extracting and analyzing constituents of any particles immobilized in the trap. In yet another embodiment, the particle trap is mounted in a crosswise body with first passage, wherein the crosswise body is slideably positionable to alternate between a first position that is fluidly confluent with the collector duct and a second position that is fluidly confluent with a smaller bore injection duct, the injection duct for extraction and analysis of the particle trap contents. The collector duct, any cartridge or particle trap therein, and related structures of the skimmer body assembly are optionally heated using ohmic, conductive, radiative or convective heating elements of the art. Optionally, by providing two traps on a reciprocating member, one trap may be used for collection of particles while the other trap is analyzed and regenerated, thus providing for continuous collection and analysis. Valveless injection for analysis is provided.

Also optionally provided is a means for injecting a volume of a carrier gas, a solvent, or a mixture thereof into the trap hollow volume of the particle trap. In a preferred system, liquid elution is used for stripping materials to be analyzed from any trapped materials, but the invention is not limited thereto.

Means for stripping a particle constituent or constituents (inclusive of adsorbed vapors) from materials accumulated in the particle trap include a) introducing a volume of a hot carrier gas into the particle trap; b) directing an infrared emission, a microwave emission, or a laser emission at the particle in the particle trap; c) resistively heating the particle trap; d) injecting a solvent or solvent vapor; e) sensing a particle constituent in situ in the particle trap and then stripping said trap; or f) a combination of one or more of the above means. Stripping may be performed to prepare accumulated particulates in the trap for analysis, such as by removing interferents or by concentrating analytes of interest in a "strippate", or may be performed after in situ analysis to regenerate the trap for a next sample. Optionally stripping may be coupled to further concentration of analytes in a secondary focusing trap.

Means for analyzing particle constituents further generally comprise a) means for performing a liquid chromatographic step; b) means for performing a gas chromatographic step; c) means for performing an affinity binding step; d) means for performing an ionization step; e) means for performing an electrophoretic step; f) means for performing a spectrometric, fluorometric, or photometric step; g) means for performing a mass spectroscopic step; h) means for performing an electron capture step; i) a combination of one or more of the above means; j) means for in situ detection; or k) other analysis and detection means known in the art.

The step for analyzing any immobilized particles may be performed in situ in the traps, or may be initiated by eluting any accumulated particle constituents of interest in a liquid volume, or by volatilizing the particle constituents in a carrier gas volume. Stripping may be performed before or after analysis, but is frequently used to prepare the captured material for analysis.

Also included are methods for sampling particulate residues from an object, structure, surface, cavity, vehicle or person to detect a threat. A method may comprise steps for: a) aspirating a first sample from a substrate or air, the first sample with a volume and a velocity into a suction intake of a sampling head and conveying the volume as a suction gas flow through an upstream channel, the volume containing particles and free vapors; b) inertially dividing the suction gas flow into a particle-enriched gas flow containing a particle concentrate and a bulk gas flow containing the bulk of the free vapors, and directing, according to a flow split, the particle-enriched gas flow to a first downstream channel and the bulk flow to a second downstream channel, wherein the first downstream channel and the second downstream channel bifurcate from the upstream channel; c) immobilizingly accumulating any particles for a time in a particle trap disposed in the first downstream channel; and d) analyzing any constituents of the particles (and any adsorbed vapors) accumulated in the trap to detect an explosive or explosive-associated residue therein. However, free vapors in the bulk flow are generally directed to atmosphere.

Typically, jets are used to assist in mobilizing, eroding and aerosolizing particles during sampling, as improves the effectiveness of a "particle-only" explosives residue sampling and analysis system.

A step for cleardown of the sampling system between analyses may also be provided. Cleardown is achieved by convectively, conductively or irradiatively heating the particle trap; by injecting a purgative solvent; by purging the particle trap under a forward or reverse flow of a gas stream therethrough; by replacing the particle trap (as with a new or reconditioned cartridge), or a combination of the above means. Cleardown thus is achieved by fully stripping the particle trap in preparation for a next sample or by replacing the trap.

Preferably the flow split and the velocity are configured to reduce elutriative losses of particles having an apparent aerodynamic diameter of 5 to 200 microns in the suction intake and wherein the flow split is generally greater than 100:1, the particles being informationally rich. In the systems claimed here, it is envisaged that the bulk flow is discharged to atmosphere without analysis.

Interchangeable sampler heads may be configured for sampling surfaces and also for interrogating spaces between surfaces, such as under pallets, between stacks of articles, inside vehicle compartments and trash cans, between boxes, in the nap or pile of a rugs, along floorboards, in bins of vegetables, and so forth, where we have found that combinations of jets with suction, can be optimized to improve overall sampling efficiency. Particulates are aerosolized by this treatment and entrained in the suction intake. High velocity jets also erode contaminated substrates to yield additional analyte.

Sampler heads may be interfaced with particle collection and analysis systems for detection of trace residues associated with explosives and explosives-associated compounds, detection of landmines, particles associated with biowarfare agents, residues or particles associated with narcotrafficking, smuggling of chemicals, and animals or animal parts, environmental contamination of surfaces with toxins, bacterial or other contamination in food processing facilities, bacteria, fungi, viruses and insects on agricultural and forest products, and so forth. These systems are thus useful as part of larger surveillance systems for surveillance of complex environments, such as traffic at a border crossing, flow of mail, monitoring of ecosystems, ingress and egress of persons to and from secure areas, and in forensic investigations, for example.

BRIEF DESCRIPTION OF THE DRAWINGS

The teachings of the present invention can be readily understood by considering the following detailed description in conjunction with the accompanying drawings, in which.

DETAILED DESCRIPTION

Figure 1A:
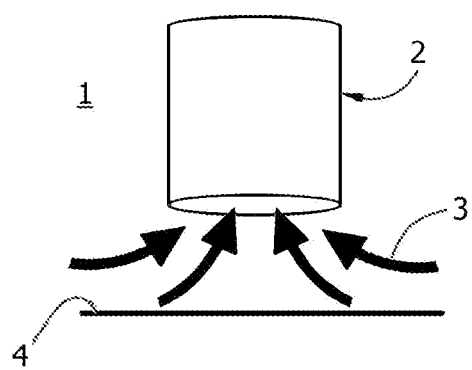
FIGS. 1A and 1B are schematic views showing devices of the prior art.

Although the following detailed description contains many specific details for the purposes of illustration, one of skill in the art will appreciate that many variations, substitutions and alterations to the following details are within the scope of the invention. Accordingly, the exemplary embodiments of the invention described below are set forth without any loss of generality to, and without imposing limitations upon, the claimed invention.

The invention has applications for surveillance and analysis of particulates and volatile residues borne upon persons, articles of clothing, interior or exterior surfaces of buildings, furnishings, vehicles, baggage, packages, mail, and so forth. The following definitions are provided for convenience.

"Particles" include dust, droplets, mists, explosives residues, chemical agents, biological particulate agents, and toxins, while not limited thereto, and are generally smaller than grains of sand. Before or during sampling, particles may form "agglomerates" that have aerosolization and settling characteristics distinct from the particles themselves. Of particular interest are particles in the range of 1 to 200 microns, more preferentially 5 to 100 microns, where most of the mass is generally found. Adsorbed vapors are frequently found as constituents of particles, including particles such as fibers, dust, soil, clay, hairs, skin cells, mists and so forth. Constituents of particles include analytes of interest, interferents, and matrix materials.

The terms "mobilization", "re-suspension", "aerosolization", and "re-aerosolization", refer to a phenomenon in which particles, initially resting on or adhering to a surface (or "substrate"), are advectively entrained in a moving gas volume in contact with the surface.

As use here, particle "aerosolization" can also involve erosion of surfaces such as cardboard, cloth, packing materials, paint, and standing water on surfaces, through the action of aggressive gas jets.

When the term, "air" is used, included as well for the purposes of the present disclosure are other gases and mixtures of gas more generally that may contain particles or vapors in dilute concentrations. For convenience, "air" includes all such gases to the extent that they act as diluents and carriers for target analytes, particles, volatiles, and vapors alike.

"Particle concentrators" include air-to-air concentrators generally, including aerodynamic lens particle concentrators, aerodynamic lens array concentrators, and micro-aerodynamic lens array concentrators when used in conjunction with a virtual impactor, skimmer or other means for inertially separating a gas flow into a particle-enriched flow (also termed "minor flow" or "scavenger flow") and a "bulk flow". Also included are cyclone separators, ultrasound concentrators, inlet particle separators, and vortex particle separators. Air-to-air concentrators split an intake flow into two downstream branches at a bifurcation, where the bifurcation may be a "skimmer", a virtual impactor, a "splitter", a simple "tee", or a particle diverter. The ratio of particle-enriched flow rate to bulk flow rate is determined according to a flow split, which is a function of the pressure drop in each of the two downstream arms, the cross-sectional area, and any resistance related to $C_v$. The particle-enriched gas stream, also sometimes termed a "particle beam" or a "particle ribbon" is delivered to an outlet of the particle concentrator or module and may be conveyed to an aerosol collector module (or "particle trap", see below). The "cut size" refers to the size of particles that are captured in the particle beam or ribbon, and is generally taken as the apparent aerodynamic size or diameter ($D_{50}$) for which 50% of the particles are captured. The cut size may be selected by design from 1 micron, or 5 microns or 10 microns, while not limited thereto.

"Aerodynamic focusing" refers to systems for forming generally collimated beams or ribbons of particles in a flowing gas stream. The systems contain three elements: an intake orifice for receiving a flowing gas stream, one or more focusing lenses disposed along the long axis of the gas stream, and an acceleration nozzle downstream from the aerodynamic lens or lenses. Aerodynamic lenses are constrictions in a channel that create converging and diverging flow accelerations and decelerations through which particle tracks converge by inertia on the center axis of flow, thereby depleting the surrounding gas streamlines of their particle content. Aerodynamic lenses may be of "slit" geometry or of "annular" geometry. Aerodynamic lens or lenses may also be disposed as arrays as described in U.S. Pat. No. 7,704,294 to Ariessohn, which is co-assigned.

"Skimmers" refer to systems for splitting a flowing gas stream at a junction so that a bulk flow and a particle-enriched flow are directed into separate, bifurcating downstream channels. Generally a "virtual impactor" is positioned to receive the minor flow in a collector duct. Skimmers are described for example in U.S. Pat. No. 7,875,095 to Ariessohn, which is co-assigned. Skimmers are related to particle splitters and particle diverters more generally, all operating by similar principles of inertia.

"Inlet particle separators" also use inertia to separate particles from surrounding gas in a moving stream. Air entering through an intake manifold is accelerated and then bent sharply. Clean, particle-depleted air flows around the bend, but particles having inertial mass are not deflected with the streamlines and are captured by a splitter lip, continuing into a "scavenger" bypass channel. The terminology may also refer to an outer bypass stream (herein a "particle-enriched flow") and a "core engine stream" (here a "particle-depleted bulk flow"). Inlet particle separators may be operated under vaneless conditions equivalent to slot-type aerodynamic lens geometry, or under swirl conditions, where vanes are used to generate a vortex-like flow regime in a cylindrical channel that forces particles to the outer wall of the channel, under and outside an annular splitter lip, and into a particle diverter duct. Clean air at the centerline of the vortex enters a downstream recovery manifold over and into the annular splitter, which can be modeled as an airfoil.

"Particle traps" or "particle collectors" include inertial impactors broadly, particularly centrifugal impactors, and also bluff body impactors and fine meshes or filters capable of capturing particles in a targeted size range. Special classes of impactors include liquid impingers and plate impactors. Also included are wetted wall impactors and rotary vane impactors. Filters for particle removal include membrane filters, depth filters, felts, mesh, mesh layers, and beds, also termed generally, "barrier filters". Also included are elutriative particle collectors. Particle collectors are described in U.S. patent application Ser. Nos. 12/364,672 (titled "Aerosol Collection and Microdroplet Delivery for Analysis") and 12/833, 665 (titled "Progressive Cut-Size Particle Trap and Aerosol Collection Apparatus"), which are coassigned and are hereby incorporated in full by reference.

Sensitivity of a trap is in part a function of preconcentration factor PF:

$$PF = C_f/C_0$$

where $C_0$ is the initial concentration of an analyte in a sample and $C_f$ is the post-collection and processing concentration. This experimental ratio may also be used to account for material lost in the trap during desorption.

"Stripping" refers to a process of removing captured materials from a particle trap, as in preparation for analysis or as in regenerating the trap for a next sample. Stripping may be performed with a combination of heat, solvent, gas, or solvent vapor, in combination with ultrasound, for example, and may involve selective extraction of constituents that are analytes of interest, interferents or matrix materials.

"Explosives residues" include 2,4,6-trinitrotoluene (TNT), nitroglycerin (NG), dinitroglycerin (DNG), ethylene glycol dinitrate (EGDN), cyclonite or hexogen (hexahydro-1,3,5-trinitro-1,3,5-triazine, RDX), octogen (HMX), pentaerythritol tetranitrate (PETN), dipicramide (DIPAM), ethylenedinitramine (EDNA), 1,3,5-triamino-2,4,6-trinitrobenzene (TATB), triacetone triperoxide (TATP), acetone peroxide/nitrocellulose (APNC), hexamethylene triperoxide diamine (HMTD), tetryl, ammonium nitrate, urea nitrate, ANFO (ammonium nitrate/fuel oil mixtures), plasticized blends of cyclomethylenetrinitramine (RDX) and PETN (Semtex), other polymer bonded explosives (PBX), for example, while not limited thereto. Explosives-associated compounds more generally, particularly volatile molecular analyte species such as ethylene glycol dinitrate (EGDN), dimethyldinitrobutane (DMDNB), mononitroluene, or isotopically labeled explosives used for "tagging" commercial explosives as a means of source identification, are also of use for detection [Steinfeld J I and J Wormhoudt. 1998. Explosives detection: a challenge for physical chemistry. Ann Rev Phys 49:203-32; Singh S. 2007. Sensors—an effective approach for the detection of explosives. J Hazardous Matl 1-2:15-28]. Dogs are very sensitive to DMDNB and can detect as little as 0.5 parts per billion in the air. Also of interest as targets for detection are those agents identified and listed by the Bureau of Alcohol, Tobacco and Firearms as explosives under section 841(d) of Title 18, USC. Firearms residues, both before and after ignition, may also be encountered.

Referring now to the figures, a conventional vacuum sampling device (1) with intake (2) is shown schematically in FIG. 1A. Under influence of suction pressure applied to the intake, flow streamlines (3) enter the intake port from the sides, sweeping across a proximate external surface (4) and picking up loose particles, but the devices have a reduced sensitivity due to dilution with ambient air and are relatively ineffective in mobilizing, eroding and aerosolizing particles. A device of this type is depicted in U.S. Pat. No. 3,748,905 to Zahlava. Also relevant is U.S. Pat. No. 5,476,794 to O'Brien.

Figure 1B:
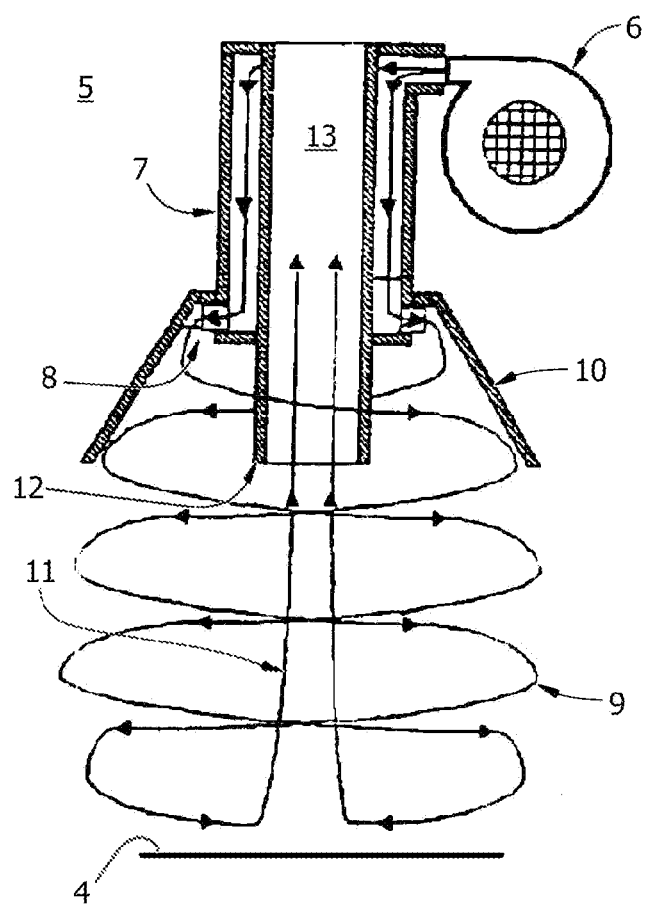
Figure 9:
Figure 10:
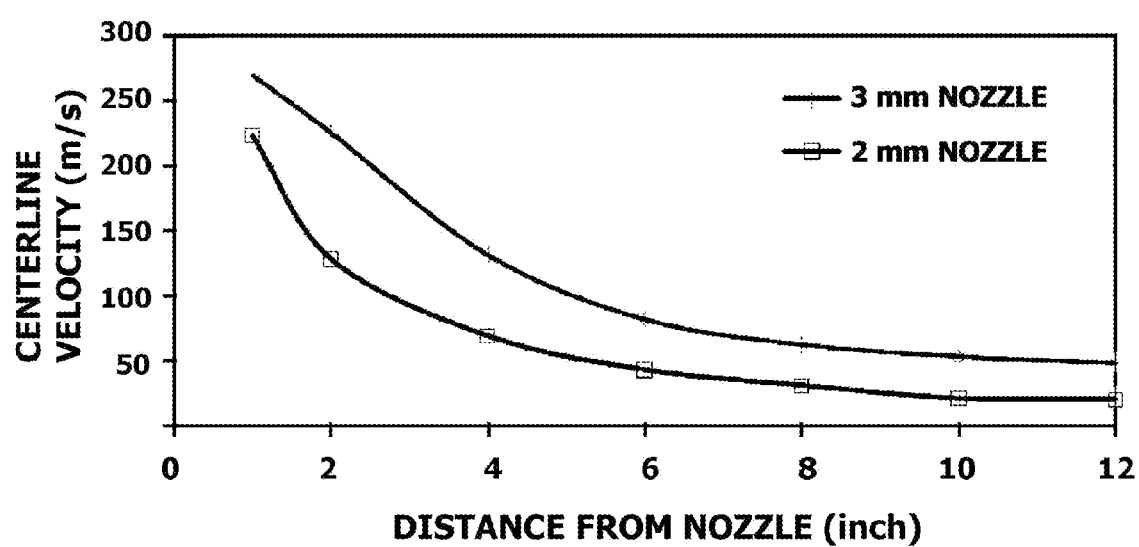
Figure 11:
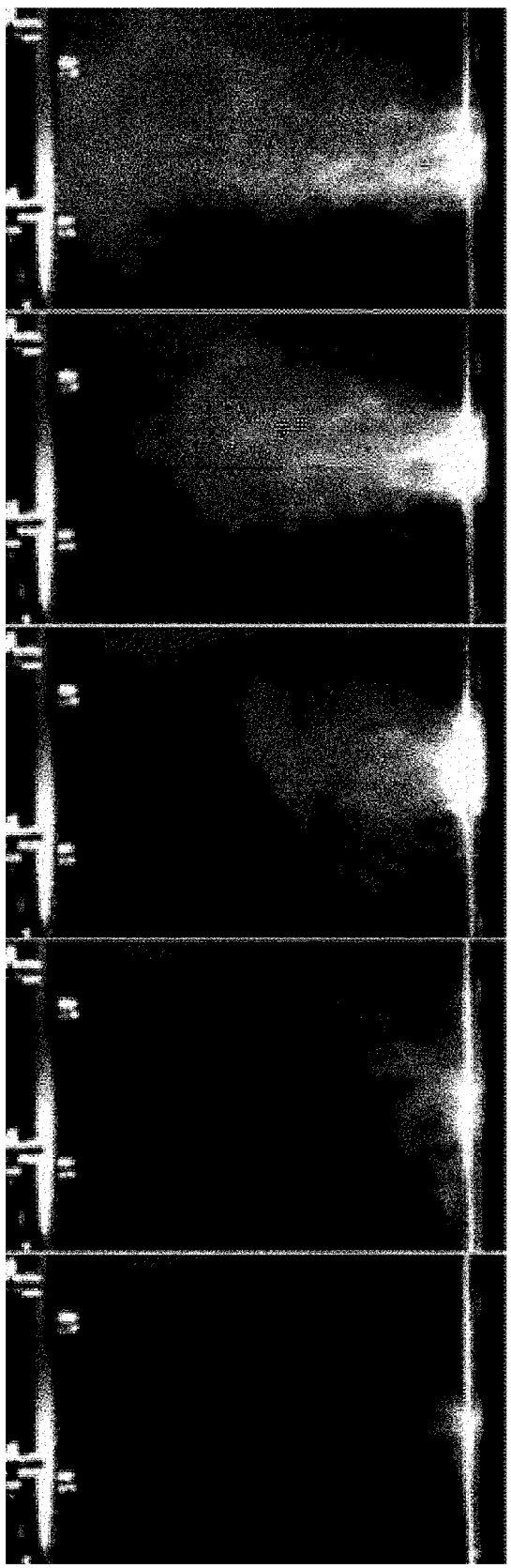
Figure 12:
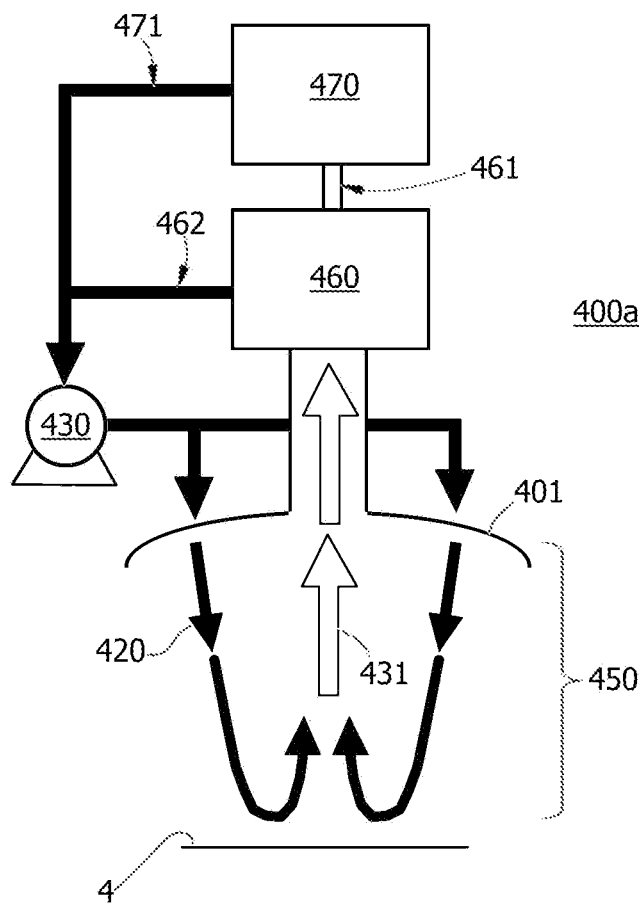

As described in U.S. Pat. Nos. 6,861,646 and 6,828,795, application of a cyclonic outer flow regime is reported to improve the ability to sample complex surfaces at a distance from the detector head. This is shown schematically in FIG. 1B. A blower (6) powers outflow of cyclonic streamlines (9) through lateral port (8) in housing (7). A bonnet (10) is used to shape the cyclone. A central vacuum intake (13) with lip 12 draws air from the base of the cyclone. Inflow streamlines (11) are seen to rise into the vacuum intake. An external surface (4) is shown to be swept by the cyclonic streamlines (9) and dislodged materials are entrained in the returning gas flow (11). Optionally a photon beam is used to generate heated vapors from a surface, which are detected by ion mobility spectroscopy. The device is reported to have an effective distance of up to 10 cm from the nozzle (U.S. Pat. No. 6,828,795, FIG. 9). Because the cyclonic streamlines (9) engage the external surface (4) at an essentially zero incidence angle, particle rolling is favored over particle detachment, limiting effectiveness in mobilizing, eroding and aerosolizing particles.

Contrastingly, we have directed sonic jet pulses or streams converging toward a virtual apex of a cone behind the surface to be interrogated without cyclonic flow. Cyclonic flow of the incident air stream is not believed relevant to the operation of our invention. We have found that for particle removal the impingement or incidence angle of a jet streamline, i.e. the angle of the streamline relative to a flat surface generally parallel to the sampler head, exhibits improved dislodgement and aspiration efficiency at an incidence angle of about 60 to 85 degrees (i.e., where 90 degrees is perpendicular).

Figure 2A:
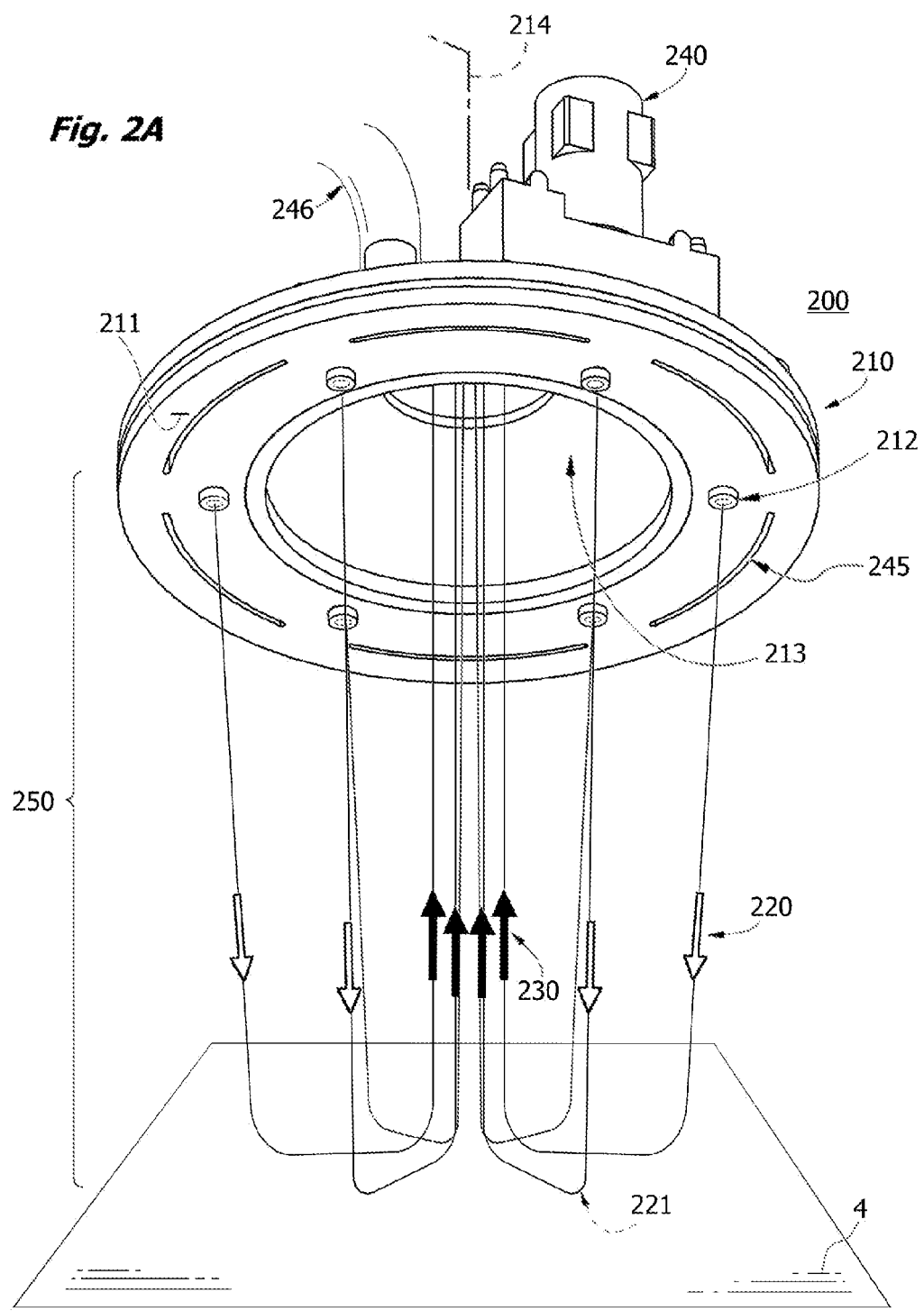
FIG. 2A is schematic depiction of a sampler head in operation, the sampler head having six sampling jets surrounding a central intake port. A "virtual sampling chamber" is formed.
Figure 2B:
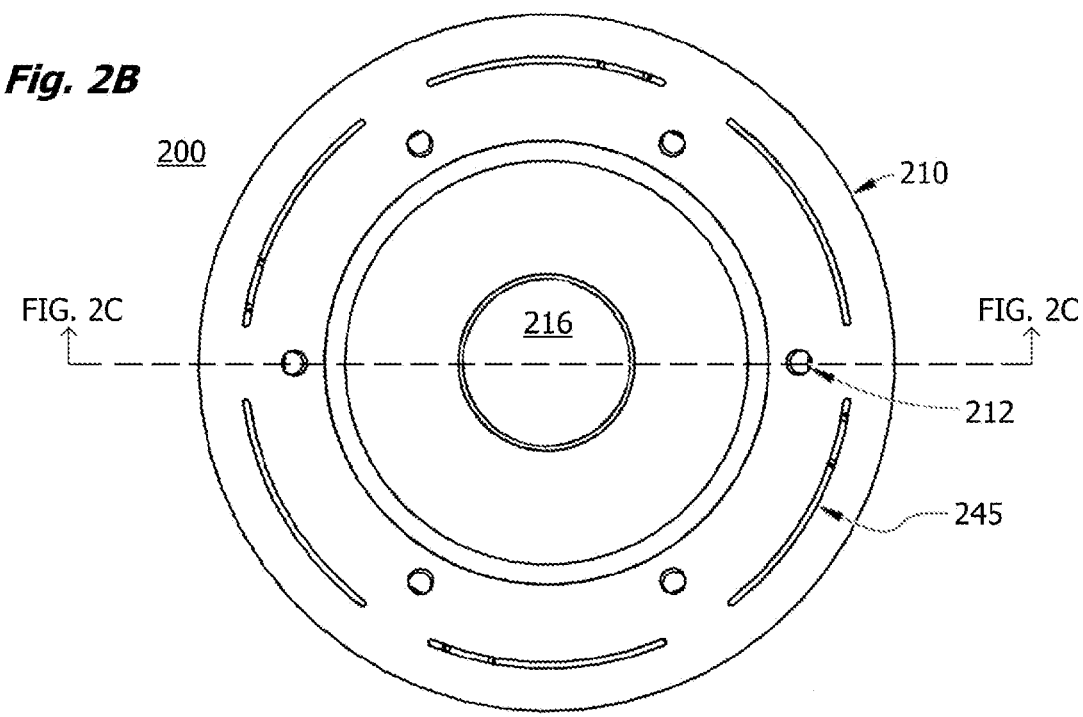
FIGS. 2B, 2C and 2D depict plan, section and elevation views of the six jet sampler head of FIG. 2A.
Figure 2C:
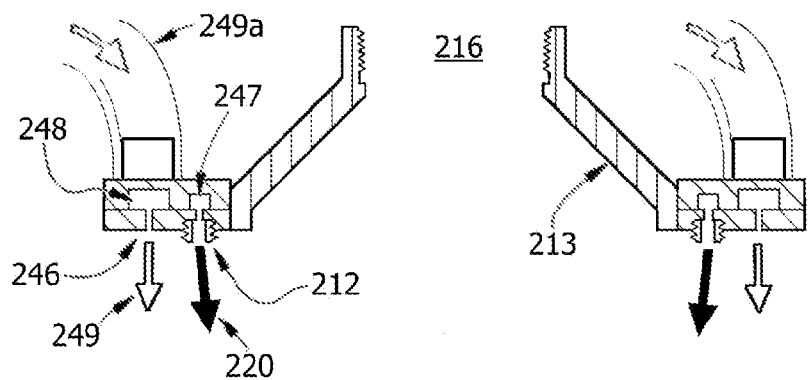
Figure 2D:
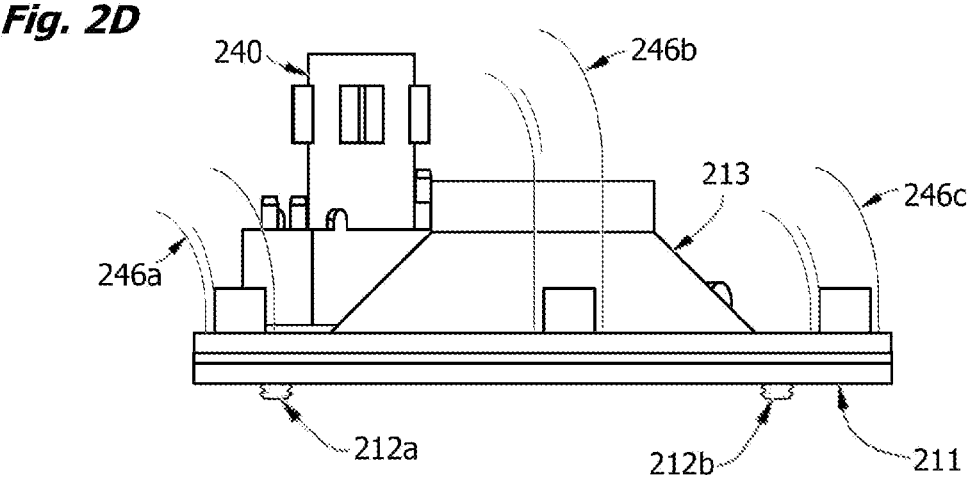

FIG. 2A depicts a "virtual sampling chamber" (250) formed of six jets of air emitted from sampling nozzles arrayed around a generally central suction intake port. The sampling jets are directed to form the walls of a virtual cone, shown here converging on an interrogated surface (4). When incident against the interrogated surface, the jets involute and are borne into the collector duct in the sampler head. In this way, particles or vapors dislodged or volatilized from the interrogated surface are entrained in the returning flow and enter the suction intake port for concentration and analysis.

In more detail, for a first embodiment (200) of the invention, sampler head (210) has a forward face (211) and a ring of jet nozzles (212) mounted in a circumferential array around a central axis (214). At the center of the forward face is a suction intake port (213) with conical inlet. Sampling jets (220) propelled from the jet nozzles (212) are directed to converge on an external surface (4), forming the walls of a truncated virtual cone. On striking the surface, the jets are turned inward and are returned under suction to the suction intake port (213). Suction is generated by a vacuum pump (or blower inlet) mounted in or connected to the sampler head. A bundled core of suction return streamlines (230) is shown at the central long axis of what is a "virtual sampling chamber" (250), the virtual sampling chamber having a truncated conical shape with base formed by the forward face (211) of the sampler head and frustrum by out-flow streamlines making an involuted frustroconical "U" turn (221) on the interrogation surface (4). The out-flowing gas jets (220) are connected with the bundled core of in-flowing return streamlines (230) directed into the suction intake by the frustroconical "U-turn" of the streamlines at the surface.

Also shown is a positive pressure source (240), here a diaphragm pump, for charging the gas jets and tubulation (246) for discharging a curtain wall flow through annular slit orifices (245) disposed as an apron around the sampler head, as will be discussed further below.

Figure 4:
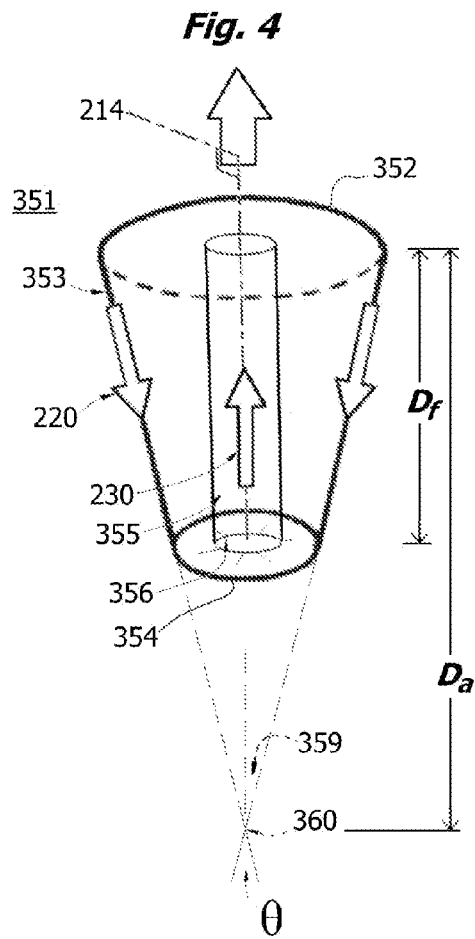
FIG. 4 is a pictographic representation of the geometry of a virtual sampling chamber.

The geometry of the conical "virtual sampling chamber" is illustrated schematically in FIG. 4. The virtual cone geometry (351) includes base (352), with central long axis (214), walls (353), apex or vertex (360), and frustrum (354). The walls of the virtual sampling chamber are formed by jets (220) flowing down the outside walls of a cone from the base to the apex. Returning flow (230) is formed by involution of the jets (220) where the cone is truncated on the frustrum. While not bound by abstract models, the returning flow is visualized as a cylinder (355) of negative pressure having a base (356) at the core of—and disposed on the long axis of—the virtual cone. An involuted frustroconical "U-turn" of the gas flow streamlines fluidly joins the gas jets (220) to the sampling return stream (230). The number of jets forming the virtual sampling chamber may be two, three, four, six, eight, or more, while not limited thereto. By shaping the jet streamlines (220) in fan or chisel shapes, a virtual cone or pyramid is readily formed with as few as two shaped jets.

As discussed further below, the sampling jets may be emitted as a single pulse or pulsed burst, and after an interval of a few microseconds, the emitted gas volume is efficiently recovered by application of a strong suction pulse. Thus it can be seen that the gas-walled sampling chamber is formed and then collapses—truly an evanescent manifestation of a virtual sampling chamber having a duty cycle of a few seconds, while not limited thereto. Individual pulse cycles may be repeated at defined pulse intervals, or in response to a triggering event.

Although not shown, the source of pressurized gas for the sampling jets and vacuum for the suction intake may include centrifugal, rotary vane, piston, or diaphragm pumps, or other pumps as known in the art. The exhaust of the suction gas generator may be used to drive the gas jets of the out-flow. A high pressure tank of a gas or pressure reservoir may be charged to a pressure setpoint and gas released using high-speed solenoid valves to generate sampling jet pulses. Pressurized gas may be stored in tubulations (such as elastic hoses) within the sampler head. An outermost peripheral annular curtain wall flow may also be used to further enclose the virtual sampling chamber, as will be described below.

Figure 46:
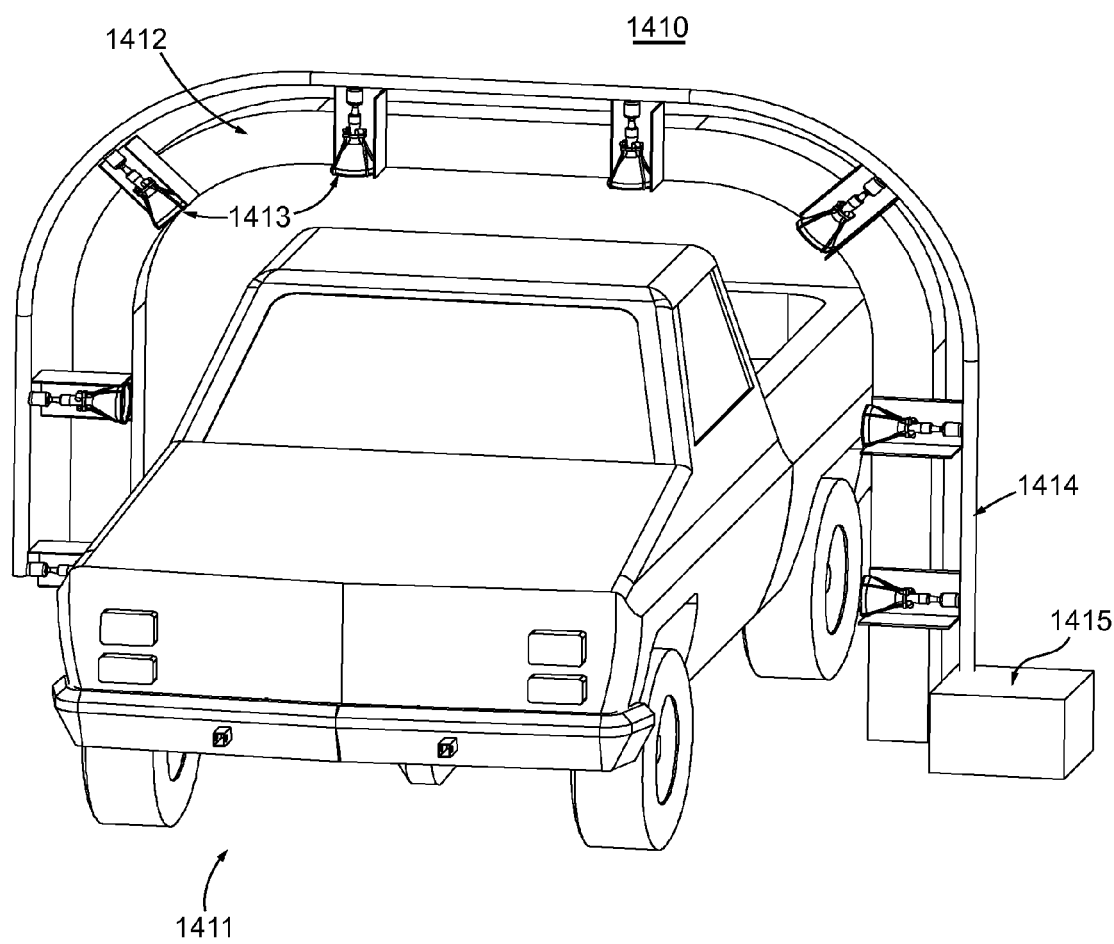
FIG. 46 pictorially depicts deployment of a sampling device array for inspection of vehicles.

Average jet flow velocities in the range of 20 to 300 m/s have been found useful in studies performed to date. The calculated average jet velocity at the outlet of a nozzle for smaller diameter nozzles approaches 300 m/s, which indicates that the velocity at the nozzle center line is sonic, and that it operates at choked conditions with higher than ambient air density. Supersonic jets may also be used. Modeling studies by computational fluid dynamics show that jet velocities and suction pressure diminish over distance from the sampling nozzle, but are capable of forming a virtual sampling chamber enclosing a distance $D_f$ of up to about 12 inches or more from the interrogated surface, where the distance $D_f$ is the height of a frustrum of a virtual cone as measured from its base (FIG. 4). In operation, the height of the virtual cone from base to apex is $D_c$, the virtual frustrum is formed with a height $D_f$, where the height $D_f$ is less than $D_c$. The distance $D_f$ may be 1 inch, 3 inches, 6 inches, 12 inches, or as found suitable for particular applications, according to the power of the jet pulses or streams.

Practical illustrations of the force of the jets in eroding residues from surfaces and forming aerosols are seen in FIGS. 11 and 39, where dry residues and liquid water are aerosolized.

The apex angle "theta" (or "vertex angle") of convergence of the jets forming the virtual cone may be varied as desired, but is found to be more effective in the range of 10 to 60 degrees, most preferably about 15 degrees. For a jet, the incidence angle is the external angle of the half angle of theta (359) and is 90 degrees for a jet normal to a surface. Incidence angle of a jet pulse is most effective in the range of 60-85 degrees. In some applications, in order to increase the standoff distance $D_c$, it may be desirable to use a jet that approaches normal (perpendicular) to the forward face of the sampler head. Instead of a virtual cone, a virtual sampling chamber that is generally cylindrical can be formed when the jets are essentially parallel in trajectory.

FIG. 2B is a face view of the underside of a sampler head (200), termed herein the forward face (210). In this view, the forward face is generally round, but is not limited thereto. Depicted are peripherally disposed gas jet nozzles (212) and annular slits (245) used for curtain wall flow. Within the bell of the sample intake port (213, FIG. 2C), is a suction inlet (216) which is ducted to a suction pressure source (not shown). Also shown is the cross-sectional plane of the view of the sampler head of FIG. 2C.

FIG. 2C is a cross-sectional view of sampler head (200). The suction intake port (213) is depicted as being conical, but is not limited thereto, and is shown here with a threaded suction inlet (216) for connecting to a negative pressure source. The central inlet is bounded by a plate for mounting the gas jet nozzles (212) represented by a black arrow (220) and containing the annular slits (246) use for curtain wall flow represented by an open arrow (249). Internal to the plate are distribution manifolds, a first plenum (247) for supplying pressurized gas to the jet nozzles (212) and a second plenum (248) for distributing make-up gas to the curtain wall slits (245). In this embodiment, the curtain wall flows (249) are supplied from a blower via tubulations (246*a*) and curtain wall plenum (248).

FIG. 2D depicts a corresponding elevation view. Shown is the conical shape of the suction intake port (213, external view), the flat forward face (211) of the sampler head, gas jets (212*a,b*) mounted in the forward face, tubulations for supplying curtain wall flow (249*a,b,c*), and a diaphragm pump (240) depicted earlier, which supplies pressurized air to the gas jet plenum (247) in this embodiment.

A computational fluid dynamics (CFD) model (300) of the pneumatic action of a sampler head with four jets (320*a,b,c,d*) is shown in FIG. 3A. With the exception of suction intake port (313) and suction pressure source (310), the mechanics of the device itself are not shown so that the pneumatic streamlines can be more readily visualized. The four sampling jets are directed downward at a surface (4) so that the jets converge slightly in proximity to the surface. The out-flow jet streamlines (321) surround a virtual sampling chamber (350). A suction return stream (332, formed by bundled parallel inflow streamlines 331) is shown directed upward within the core of the virtual sampling chamber. Out-flowing jet streamlines (321) bend at the bottom, involuting as a frustroconical "U" shaped squarish toroid (333) where contacting the external surface (4). As shown by CFD, vortex cyclonic flow does not develop under these conditions. FIGS. 3B through 3D represent figuratively the 'footprint' of the jet out-flow streamlines (321) and suction in-flow streamlines (331) on an interrogated external surface for three, four and eight jet configurations.

The impingement or incidence angle of a linear streamline forming the walls of a virtual sampling chamber is most effective for residue dislodgement and aspiration at about 5 to 30 degrees from normal (i.e. about 60 to 85 degrees from horizontal to the surface), which cannot be achieved in a cyclonic flow regime, where streamlines are essentially perpendicular to the bulk axis of flow and the impingement angle approaches zero. At lower impingement angles, rolling and sliding of particles is favored over lift-off. The higher impingement angle permits the use of higher intensity focused jets and the application of pulsatile sonic and supersonic flow regimes, which results in lift-off and removal of both particulate and volatile materials from irregular and complex surfaces, and in better re-aerosolization and aspiration efficiencies for particles.

Optionally, by balancing the "out-flow" of the jet nozzles and the "in-flow" of the suction intake, a closed loop may be formed in which sample residues are concentrated over multiple passes through a vapor or particle trap. The sampling device is intended for particle and vapor removal and for aspiration of dislodged particles and vapors into the sample head from surfaces or objects from a distance $D_f$ of up to about 1 foot, for example a vehicle driven between stanchions supporting sampling devices directed at intervals onto the surfaces of the vehicle (FIG. 46). The size and power of the jets and suction intake can be scaled for larger standoff distances if needed. In other embodiments, an open-loop is formed by firing the jets from a pressurized reservoir and ducting the bulk flow of the sampling return stream through a blower and filter to charge a curtain wall flow.

While configurations with four jets, six jets and eight jets are shown, other configurations and numbers of jets are envisaged. In selected geometries, a three-jet or a two jet sampler head, where the jets are fan shaped, is directed at a surface and a mated central suction intake is configured to capture materials ejected from the surface by the impinging jets, optionally with a curtain wall or apron of flowing air improve containment. Other variants for establishing a virtual sampling chamber are possible and are not enumerated here.

Figure 5:
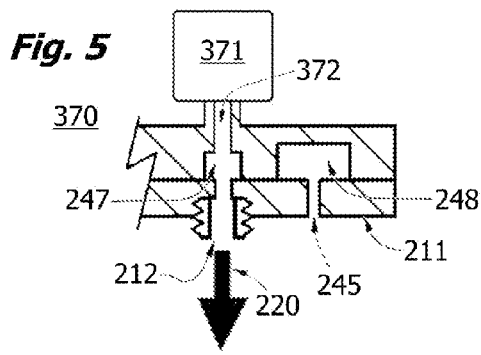
FIG. 5 shows a detail of solenoid valve control of a gas interrogation jet in a sampler head.

FIG. 5 depicts a detail of solenoid valve control of a gas interrogation jet in a sampler head. Jet control assembly (370) includes solenoid valve (371), control wiring not shown), and jet gas supply duct (372) fluidly connected to the jet plenum (247). Gas supplied to the plenum is rapidly distributed through the plenum manifold to all jet nozzles in the array. The array of jet nozzles is fired in synchrony. A jet pulse (220) is schematically depicted exiting jet nozzle (212) mounted on the forward face (211) of the sampler head. Also shown is curtain wall plenum (248) and curtain wall orifice (245). The curtain wall may be operated continuously or operated intermittently under solenoid control.

Figure 6:
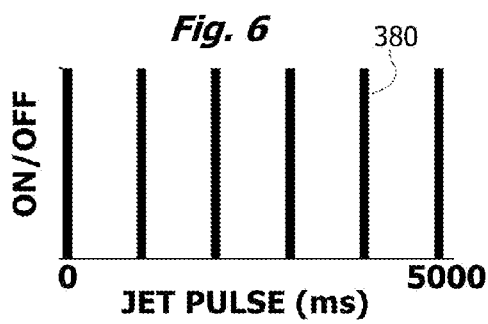
FIG. 6 represents a pulse train of gas jets firing in synchrony.
Figure 7:
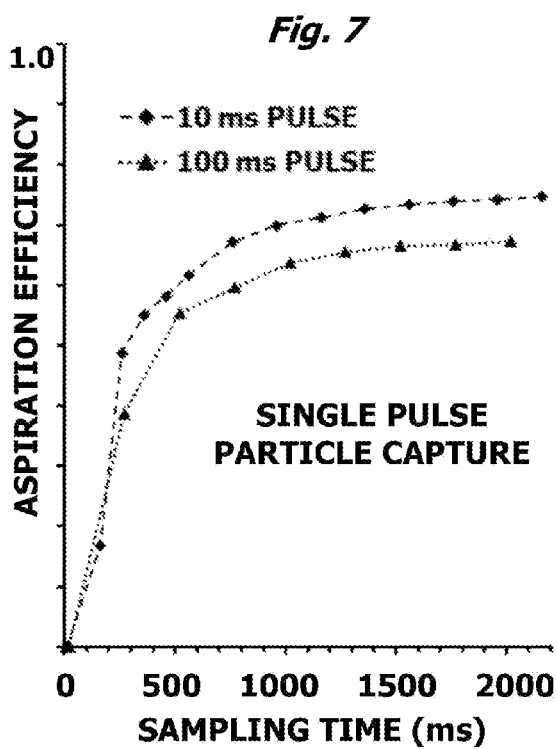
FIG. 7 is a plot showing single pulse particle aspiration efficiency $\eta_A$ as a function of pulse duration in an eight jet device.
Figure 8:
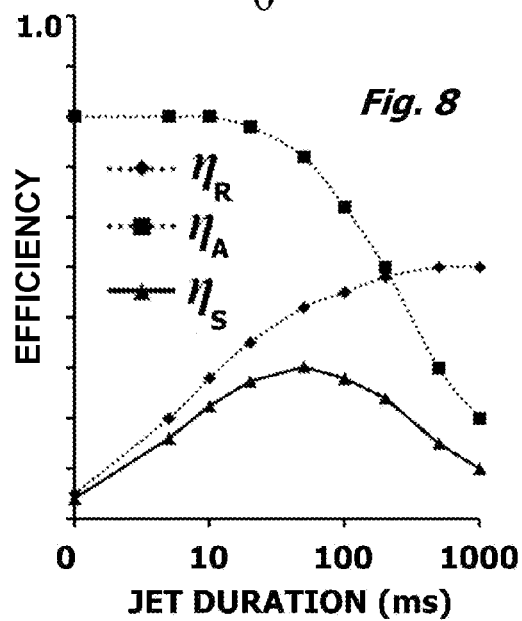
FIG. 8 is a plot showing particle s

FIG. 6 represents a pulse train of gas jets firing in synchrony over a period of 5000 milliseconds. Each gas jet pulse (380) originates as a pressurized wave of gas equilibrated through plenum (247) and discharged through an array of nozzles (212). Gas jet pulses are followed by a period of continued suction to capture materials dispersed in the virtual sampling chamber by virtue of the impact of the gas jet or shock wave on the external surface. During the suction part of the cycle, make up air may be supplied from the surrounding air column or from an optional curtain wall flow. While gas jet flow may be operated continuously, in practice this has not proved necessary, and discontinuous application of jet pulses with a limited duty cycle is advantageous. In one method of practice of the invention, sampling jet pulses as fired as synchronous pulses or as a train of synchronous pulses having a pulse duration of less than or about 20 microseconds and a pulse interval of less than or about 200 microseconds, thereby intermittently forming a virtual sampling chamber on the surface of a surface to be interrogated for volatile residues or particulate matter.

The effect of pulse duration and pulse separation is analyzed in FIGS. 7 and 8. Sampling efficiency may be viewed as an exercise in optimization of two processes, the process of entrainment of residues associated with the interrogated surface in the gas streamlines (i.e. the process of "removing" or "mobilizing" residues from a surface) and the process of capturing those vapors and particulate residues in the suction intake stream. The processes compete because excessive velocities of particles kicked up by the gas jets can propel them out of the sampling cone. Thus the overall sampling efficiency $\eta_S$ is approximated by the equation:

$$\eta_S=\eta_R*\eta_A,$$

where $\eta_S$ is the product of two efficiencies, the removal efficiency $\eta_R$ and the aspiration efficiency $\eta_A$.

In FIG. 7 the effect of pulse duration is shown to have a paradoxical effect on particle aspiration efficiency $\eta_A$ of an eight-jet sampler head. The upper curve (dashed line) shows the timecourse for particle capture following a single 10 ms jet pulse; the lower curve (dotted line) compares the timecourse for a single 100 ms pulse. With longer pulse duration, particle aspiration efficiency drops due to loss of particles from the sampling cone.

However, when corrected for removal efficiency, overall efficiency is shown in FIG. 8, where particle sampling efficiency $\eta_S$ is plotted as a function of jet pulse duration, showing the combined contributions of the dislodgement process and the aspiration process. For each condition, suction flow is commenced before triggering of the gas jet pulse and is sustained after termination of the pulse. Thus pulse duration is optimized by supplying sufficient time for aggressive scouring of the surface but using a minimal time to avoid loss of agitated particles from the containment zone.

Supplemental means for dislodging particles and volatile residues in the sampling cone include pulsatile flow regimes as described by Ziskind (Gutfinger C and G Ziskind, 1999, Particle resuspension by air jets—application to clean rooms. J Aerosol Sci 30:S537-38; Ziskind G et al, 2002, Experimental investigation of particle removal from surfaces by pulsed air jets. Aerosol Sci Tech 36:652-59), ionized plasmas directed through the sampling jets, liquid or solvent directed through the sampling jets, or shock waves directed from the sampler head. The gas in the loop may also be heated, chilled or humidified to improve performance, although caution is taken to avoid losses of volatile particles due to heating. If desired, the jet nozzle array may be operated in repetitive pulse mode, for example for sampling of a continuously moving belt.

FIG. 9 visually depicts the dynamic action of the interrogation jets. An array of eight jets can be seen to fire in synchrony in this graphical illustration. The appearance of the jets is enhanced by the introduction of particles in the gas flows which appear as the fine white pixilation against a black background. The duration of the pulse is about 20 milliseconds, during which high speed jet flow is clearly visible.

FIG. 10 is a plot of jet velocity versus distance from the nozzle orifice under experimental conditions. Velocities for a 3 mm and 2 mm diameter nozzle are shown. The jet flow velocities of the apparatus of FIG. 9 were measured by heated wire anemometry. The jets maintain a well defined linear core velocity for up to twelve inches away from the nozzle. Synchronous pulses having a centerline nozzle velocity of about Mach 0.3 are achieved. Supersonic pulses are also conceived. Flow rates of 200, 500, 800, 1000 sLpm or greater are achieved. Pulses of 5, 10, 15 or 20 ms duration may be actuated as frequently as every 20 ms if desired. Alternatively, pulses may be actuated at 50, 200 or 1000 ms intervals, for example.

FIG. 11 is a time lapse view of a jet pulse/suction cycle. In this graphical illustration, a time lapse view of the action of the array of gas interrogation jets on a field of particles on a solid surface is shown. The stationary nozzles are visible at the top of the image and a thin horizontal line of the solid surface is visible at the bottom of the image. Frames are taken at 5, 7, 11, 16 and 26 milliseconds, as shown here from left to right, where the explosion of particle dust as the pulse propagates against the solid surface is clearly visible. In the later frames, a plume of particulate is seen to rise and be channeled by a suction pressure into the central collection intake at the top of the image.

Also conceived is an apparatus combining functional elements for separating particles and vapors in an air-to-air concentrator followed by particle trapping for analysis. FIG. 12 depicts a schematic of a particle sampling apparatus (400$a$) with housing (401, represented schematically), particle concentrator (460) and particle trap (470). Gas containing residues and aerosols is collected in the intake (431) routed to the particle concentrator. Aerodynamic lenses for example organize aerosols into a stream consisting of a particle-depleted bulk flow and a particle-enriched flow, which may be separated by a skimmer into what are commonly termed the "minor flow" and the "bulk flow", where the bulk flow contains most of the particles exceeding a particular cut size.

A flow split is established whereby part of the gas flow, the "minor flow" (461) enriched for particles, is directed to the particle collector or trap (470). The particle-depleted "bulk" or "major" flow (462) is diverted, typically by use of a skimmer, and is ducted instead directly to the suction pressure pump. All the gas exhausted from the concentrator (462) and the gas exhausted from the particle trap (471) are returned to a common suction pressure source for recirculation through the sampler head. As shown in this example, the pressurized exhaust from the vacuum pump or blower (430) is used to drive sampling jets (420) forming the virtual sampling chamber (450). Particles resident on the interrogated surface (4) are dislodged and drawn into the sampler head. Material in the particle trap is periodically analyzed in situ by methods known in the art, or archived for example by removal of a filter cartridge for later analysis by chemical, biochemical or physical methods. Separate pumps may be used for out-flow and suction in-flows if asymmetric flow rates are desired. Gas flows may be filtered or purified before re-use if desired.

An apparatus with one or more combinations of particle and/or vapor analytical capability is also envisaged. Detection means for analysis and identification of particles or vapors are known in the art and may be selected for physical, chemical or biological analysis.

Figure 13:
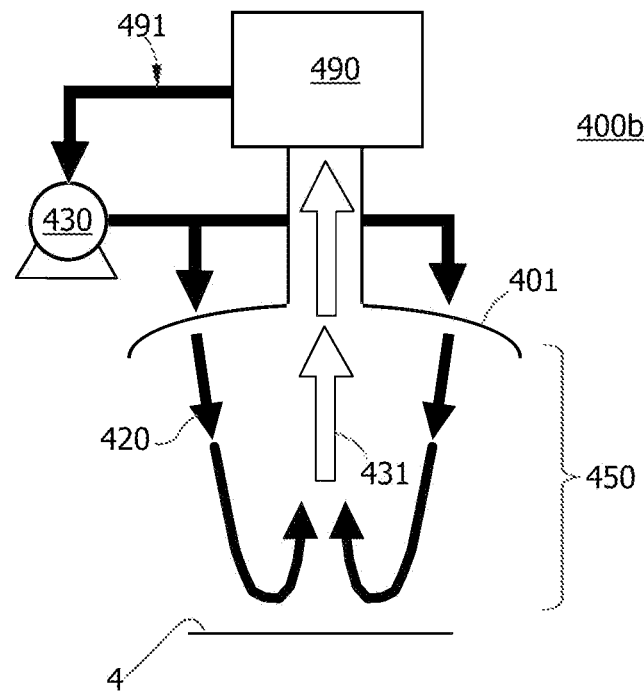

FIG. 13 depicts a schematic for one embodiment (400b) of a vapor sampling apparatus with vapor trap (490), vapor trap return flow (491), and housing (401). As shown, a virtual sampling chamber (450) is formed by gas jets (420) and a suction return stream (431) to the vapor trap. Vapor may be trapped, for example, as a condensate or by solid phase adsorption. A pump (430) recirculates the gas or air at the desired flow rate, with the linear velocity determined by the size of the jet orifices and the flow rate. The sampler head is held at a stand-off distance from the interrogated surface (4). Material collected in the vapor trap is periodically removed or volatilized for analysis by methods known in the art such as flash heating, ultrasound, or fast atom bombardment. Known in the art, for example, is the flash heater described by the Naval Research Laboratory [Voiculescu et al, 2006, Micro-preconcentrator for Enhanced Trace Detection of Explosives and Chemical Agents IEEE Sens. J. 6:1094-1104] and heating means disclosed by Spangler in U.S. Pat. No. 5,083,019, by Fite in U.S. Pat. No. 5,142,143, by Linker in U.S. Pat. Nos. 6,345,545 and 7,299,711, and by Combes in US Pat. Appl. Publ. No. 2009/0211336. Also contemplated is the oxidative flash heater of Pataschnick (U.S. Pat. No. 5,110,747). Included are flash bulb heaters, lasers, resistive heaters, hot purge gas, and microwave heaters as are generally known for heating.

Figure 14:
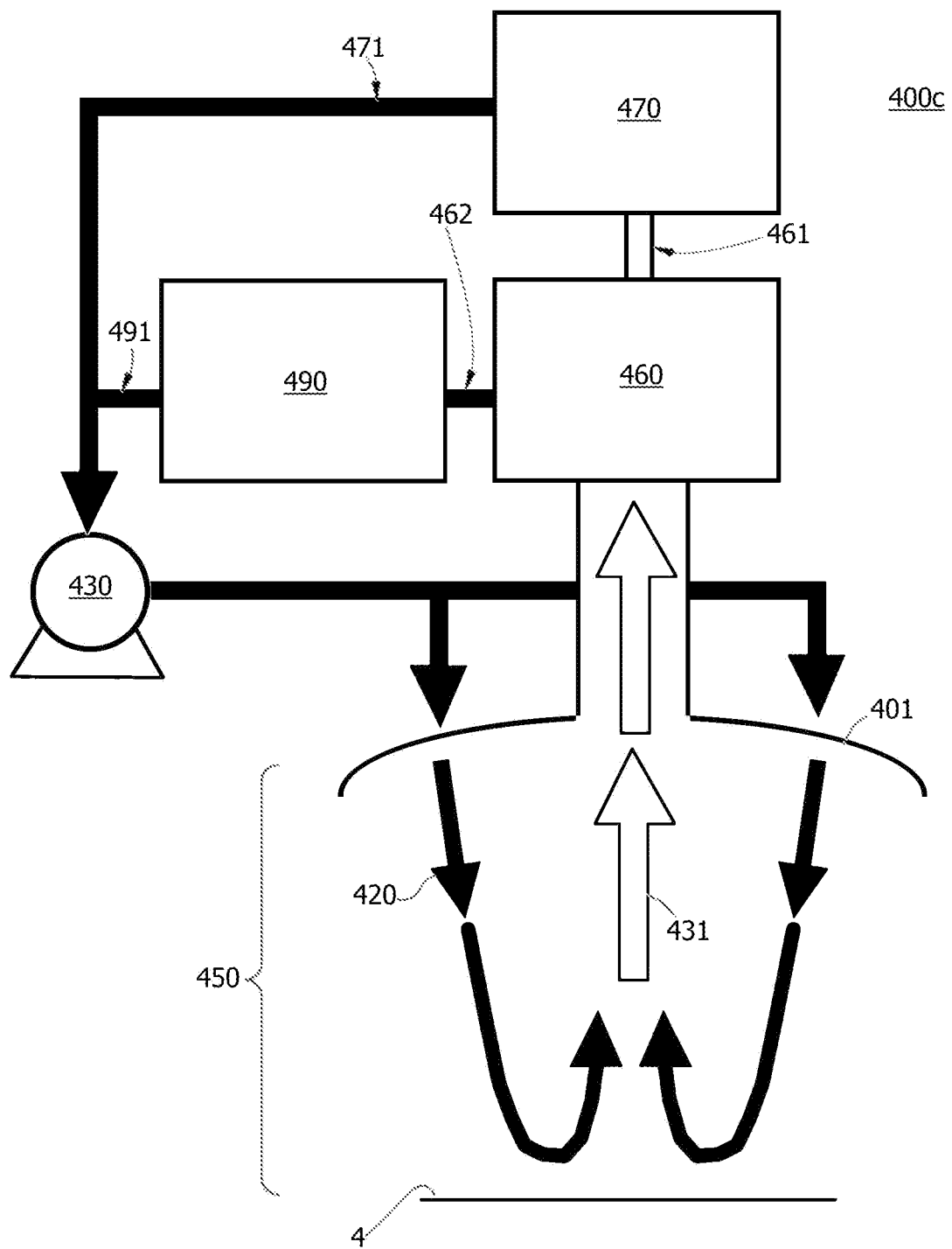

FIG. 14 is a schematic of an apparatus (400c) for capture of vapors and particles. Particles (and vapors associated with the particle fraction) are captured in the particle trap (470) and vapors that are conveyed by the particle concentrator (460) in the bulk or "major" flow (462) are captured in a vapor trap (490) before the gas (491) is recycled through vacuum/blower (430) and propulsed through the housing (401) as gas jets (420) into the virtual sampling chamber (450). Minor flow (461) from particle concentrator (460) is routed to the particle collector (470) and exhaust gas (471) is recycled through the vacuum/blower, essentially as a closed loop system, where there is a mass balance between jet in-flow gas and suction return stream (431) gas recovered from the virtual sampling chamber.

Equilibrium vapor pressures of explosive materials range widely, from over $4.4 \times 10^{-4}$ Torr for nitroglycerin (NG, which is considered to be a relatively volatile explosive), $7.1 \times 10^{-6}$ Torr for TNT, to $1.4 \times 10^{-8}$ Torr for PETN and $4.6 \times 10^{-9}$ Torr for RDX at 25° C. [Conrad F J 1984 Nucl Mater Manag 13:212]. Also to be considered, however, is the affinity of the vapor molecules for solid surfaces, which may suppress free vapor concentrations, thus reducing detectable thresholds. We find that detection of volatile compounds such a dinitrotoluene, a model substance for explosives detection which has an affinity for solid surfaces, can be improved by collecting particles that have equilibrated with vapors of the explosive. These particles are typically endogenous materials that are exposed to the explosive residues in the environment, for example road dust, silica, ceramic, clay, squamous epithelial cells, hairs, fibers, and so forth. By collection of exogenous particulate materials, explosives residues associated with the particulate debris are found to be more reliably detected.

Figure 15:
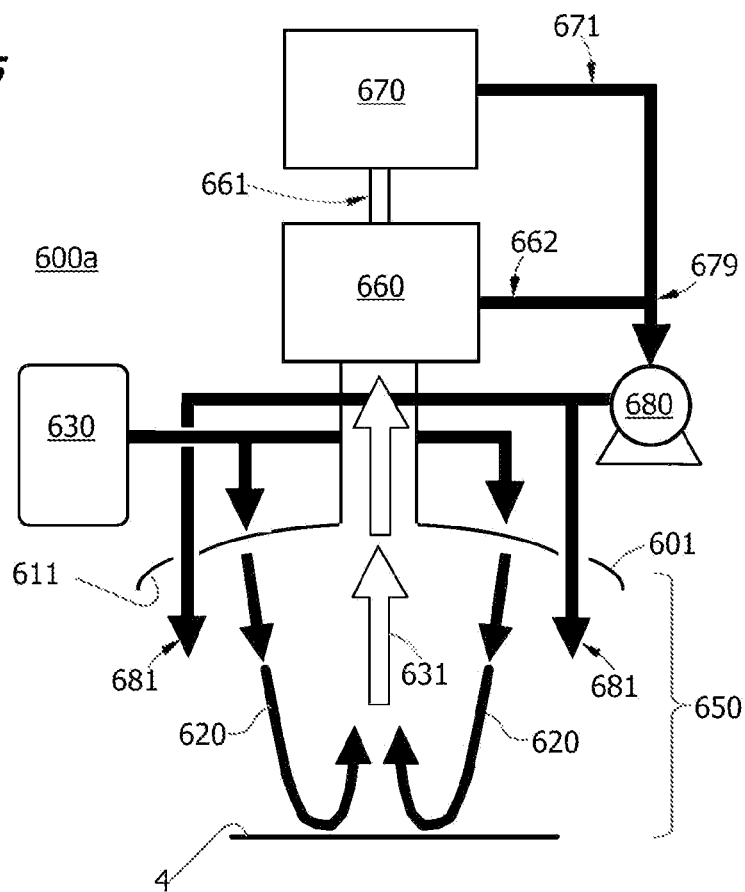
Figure 16:
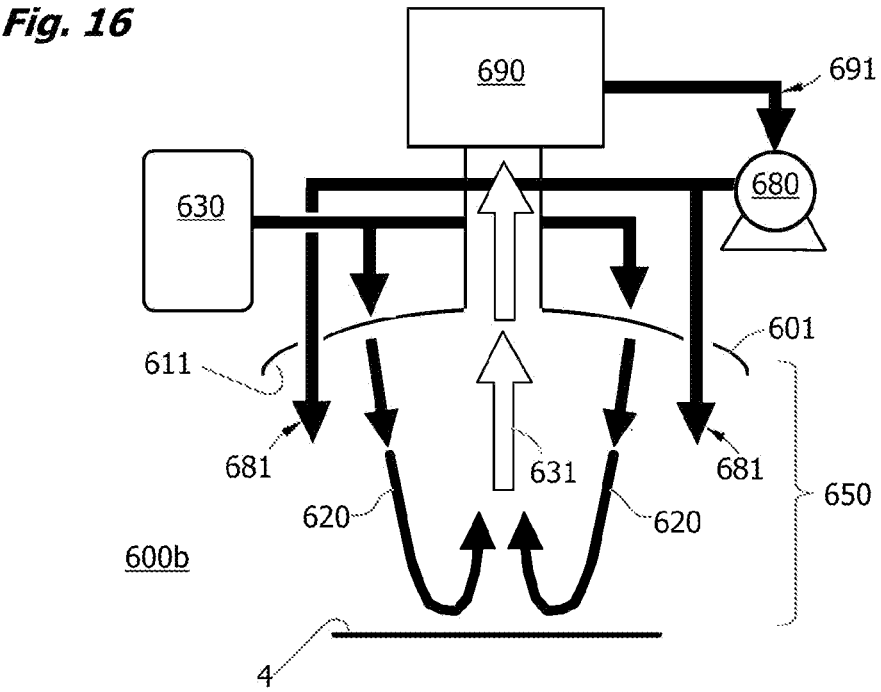

FIGS. 15 and 16 are schematics of pressurized pulse-driven devices (600a,b) augmented with curtain wall flow for capturing particles or vapors from an interrogated surface (4). In FIG. 15, the sampler head (601) comprises a suction pump/blower (680) that draws suction return flow (631) from a collector duct through a particle concentrator module (660) and a particle trap (670) in series. Bulk or "major" flow (662) and minor flow exhaust (671) are recombined as a single stream (679) for return to the suction pump as make up air. The suction pump exhaust is ducted to slit apertures on the outer perimeter of the sampler head. The slit apertures form a peripheral annulus outside the array of jet nozzles on the forward face (611) of the sampler head (601). These outermost slit apertures generate a curtain wall of flow (681) that surrounds and forms an apron around the virtual sampling chamber (650). The virtual sampling chamber is formed by pulsatile jet flows (620) from a pressurized air source (630), here shown as a 20 psig tank, although other pressures and pressure sources up to 60 or 100 psig have been found to be useful. In this configuration, the virtual sampling chamber is enclosed in the peripheral flow of the curtain wall but the sampling jets are pulsatile in nature. Single pulses or trains of pulses may be used. Generally the curtain air is continuously ON while sampling is pulsatile, but other suction regimes may be useful.

FIG. 16 shows a corresponding sampler head (601) for collection of vapors, where air captured in the suction return flow (631) by the collector duct is passed through a vapor trap (690) before being returned (691) to the suction/blower (680) and exhausted as curtain wall flow (681) through a peripherally disposed circumferential array of slits. Jet gas (620) is supplied from a pressurized tank (630).

Figure 17:
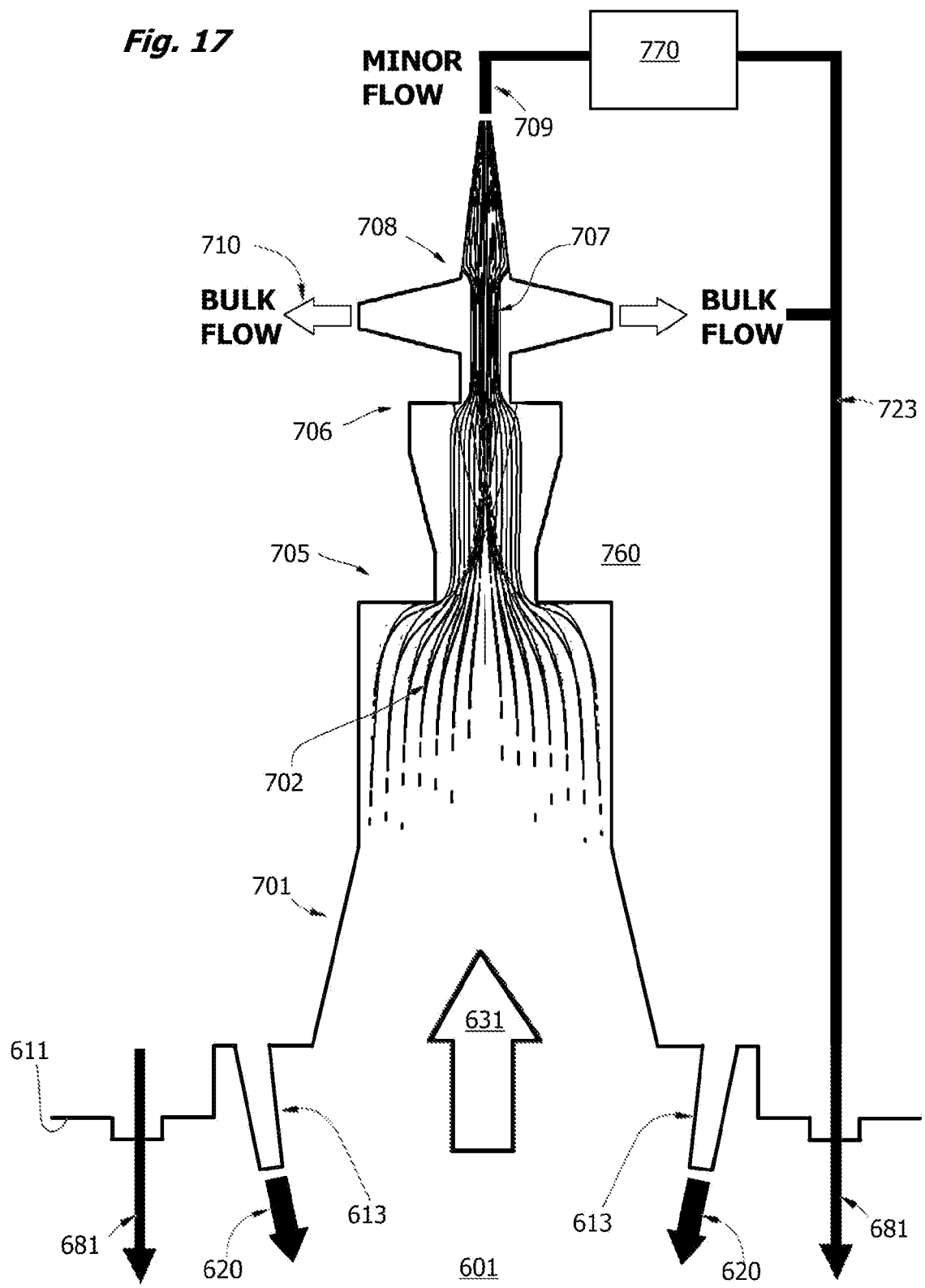

FIG. 17 depicts a cross-sectional view of a combination "sniffer head" and particle concentration device with annular aerodynamic lenses (705,706). Unlike slit-type aerodynamic lenses, these lenses are cylindrical in cross-section. A curtain wall flow (681) from annular slit nozzles disposed on the forward face (611) of the sampler head is used to enclose a virtual sampling chamber. Interrogation jets (620) are fired from nozzles (613) as pulsatile flow at a surface beneath the sampler head (not shown). Air within the virtual sampling chamber is carried into a suction intake member (701) so that any entrained particulate or vapor material in the suction return stream (631) is captured and drawn under suction through a particle concentrator (760). The particle concentrator shown here is comprised of a two-stage aerodynamic lens assembly (705,706) and a virtual impactor (708, "skimmer"). Particle tracks (702) are shown to be focused by the aerodynamic lenses so as to form a particle-enriched flow (707) surrounded by a particle-depleted bulk flow. The core and sheath are separated in the skimmer: bulk flow is diverted as "bulk flow" (710) and the particle-enriched flow (707) continues through collector duct and exits the concentrator as the "minor flow" (709). The degree of concentration is determined by the flow split between bulk and minor flow. The characteristics of the concentrator also determine a cut-size (as aerodynamic diameter). The configuration can be varied so that the cut size is in the range of 5 to 10 microns or less, for example, as is useful for a variety of applications. The minor stream may be directed through a particle trap or filter cartridge (770), and the exhaust is recycled (723) through a suction/blower (not shown) and used to generate the curtain wall flow (681).

Surprisingly, one or more jet pulses of several milliseconds can be superimposed on curtain flow and suction cycles of one to several seconds, during which the flow regime conforms to the conditions required for use of stacked aerodynamic lenses as shown.

Figure 18:
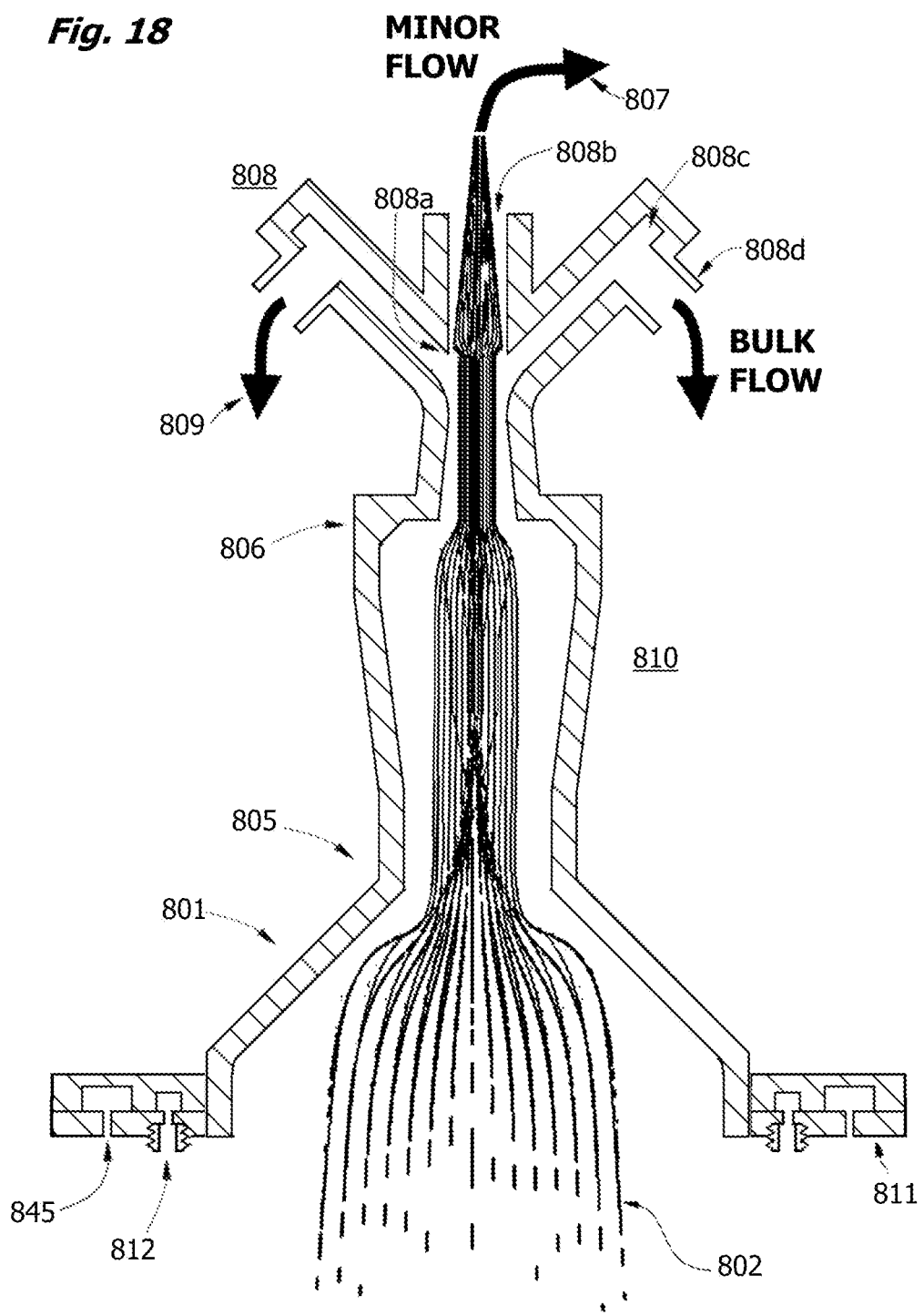

FIG. 18 depicts a cross-sectional view of a combination sampler head and particle concentration device with suction intake having a generally conical geometry (801). As shown here, the intake bell receives a particle-loaded suction return flow and focuses particle tracks (802) in a pair of aerodynamic lenses (805,806). A virtual impactor (808) is used to separate minor flow (807) and bulk flow (809). Minor flow is channeled to a particle concentrator and then recombined with bulk flow for recycling to curtain wall flow (681). As described previously, the sniffer head consists of a forward face (811) with jet nozzles (812), annular slit nozzles (845) and a central suction intake member (801).

The virtual impactor (808) is comprised of a skimmer mouth (808a), a collector duct (808b), a discoid chimney duct (808c) for routing the bulk flow (809) to nipples (808d) adapted, as shown here, for a hose connection to a vacuum source. Aerosolized particulate material is collected in a trap associated with the minor flow. Explosives materials for example are frequently crystalline or solid and are detected when aerosolized by a pressurized jet. Flow splits of greater than 100× are readily achieved with annular devices of this type, dramatically leveraging detection sensitivity by several orders of magnitude.

Multiple aerodynamic lenses may be used. For example by stacking four lenses, concentration of particles over a broad range of particle sizes can be achieved. Beginning with the first lens, which acts on larger particles, the remaining lenses in the stack progressively act on smaller particles in steps of 2× to 4×. Thus by example, a four lens stacks may focus particles of 100, 30, 10, and 5 microns respectively, while not limited thereto.

In order to increase particle velocities in the collector duct and reduce elutriative effects, the intake duct or "bell" geometry may be aerodynamically shaped to minimize particle impact, for example as per a NACA duct, Laval duct, elliptical duct intake, bell shaped duct intake, parabolic horn intake, exponential horn intake, quadratic convergent duct intake, power series convergent duct intake, or other tapered geometry of the intake. Fins or airfoils for minimizing turbulence, reducing deadspace and increasing linear velocities of the streamlines may also be used. As the lenses are improved by contouring to relieve eddy separation and particle wall impaction, performance is also seen to improve significantly, particularly in the collection of larger particles, which problematically are otherwise lost to sedimentation and rebound following wall impaction in the sampler head and concentrator.

Figure 19:
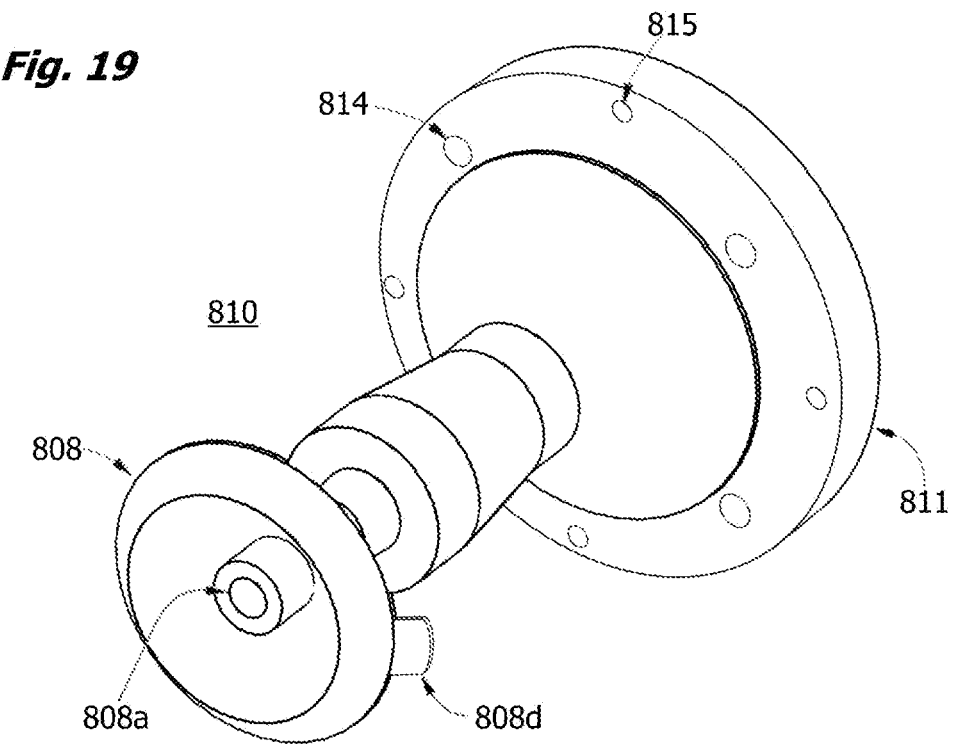

FIG. 19 is a CAD drawing of the combination sampler head and annular aerodynamic lens with skimmer assembly (810) of FIG. 18. The forward face (811) of the intake bell is pointed away from the viewer in this case so that the discoid skimmer assembly (808) is more clearly depicted. A collector duct with skimmer mouth (808a) and bulk flow exhaust hose nipple (808d) are labeled. Also shown are mounting points on the lower sampler head for gas jet feed (814) and for a curtain air slot feed (815). Tubulations are not shown for simplicity.

Figure 20:
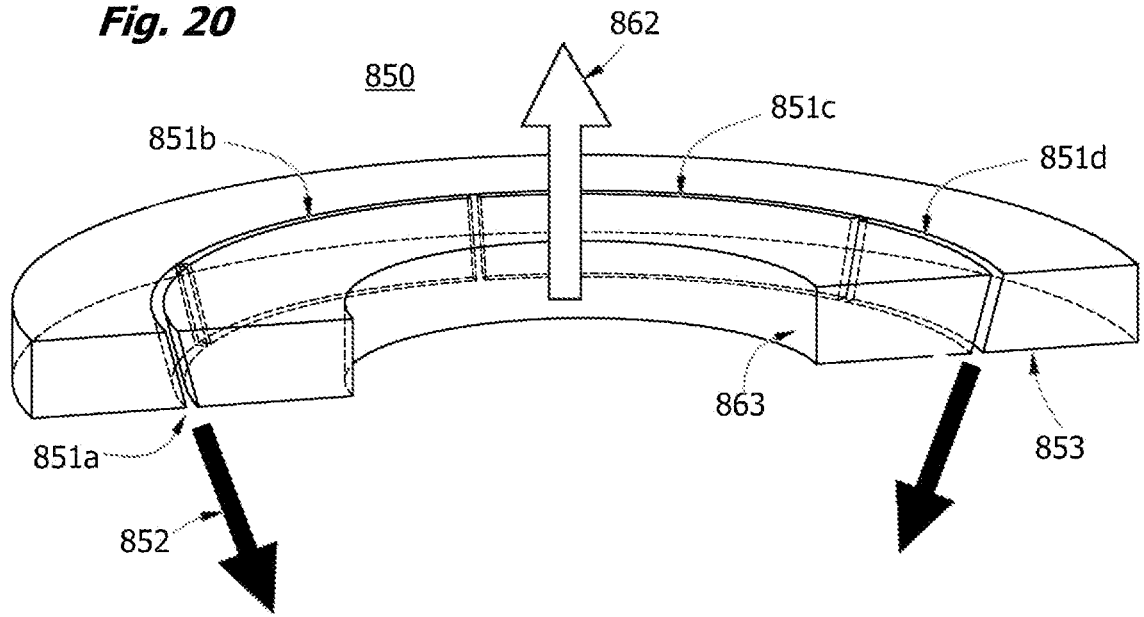

FIG. 20 is a cutaway CAD view of a jet nozzle array with slit geometry. Here the architecture of the jet nozzles is modified and integrated into the material of the sampler head (850). The forward face (853) of the sampler head is configured for emitting fan-shaped jets (852) via a ring of slits (851a,b,c,d). Central suction intake port (863) for receiving sampling flow stream (862) is shown in cutaway view, where the front half of the sampler head is not shown.

Devices and systems of the invention have applications for sampling and detection of explosives residues. A wide range of analytes must be detected. Surveillance systems for selective sampling and detection of only a few explosives-associated analytes or families of analytes would have significant vulnerabilities. Nitro- and nitrate-based materials are the most numerous, but materials such as perchlorates, peroxides, azides, incendiaries, propellants, and hydrocarbons must also be considered. Mixtures and combinations, such as of fuel oil and ammonium nitrate, are also of interest. Detection of crystalline ammonium nitrate in combination with fuel oil vapor is significantly more conclusive than detection of either a nitrate (such as from a prescription tablet) or a fuel oil vapor (such as from dirty shoes) alone. Also of particular interest are mixtures including taggants and other explosives-associated chemicals (XAM) indicative of processed explosives.

Figures 21, 22:
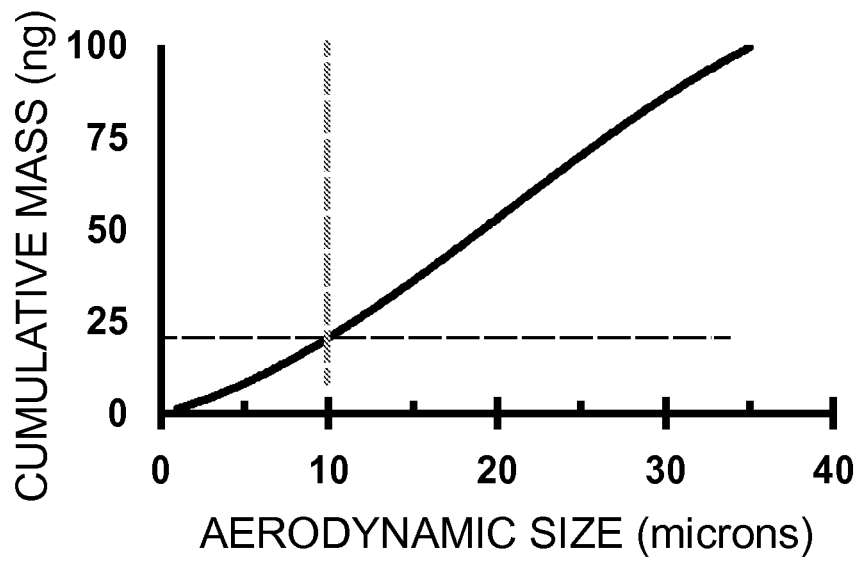
Figure 23:
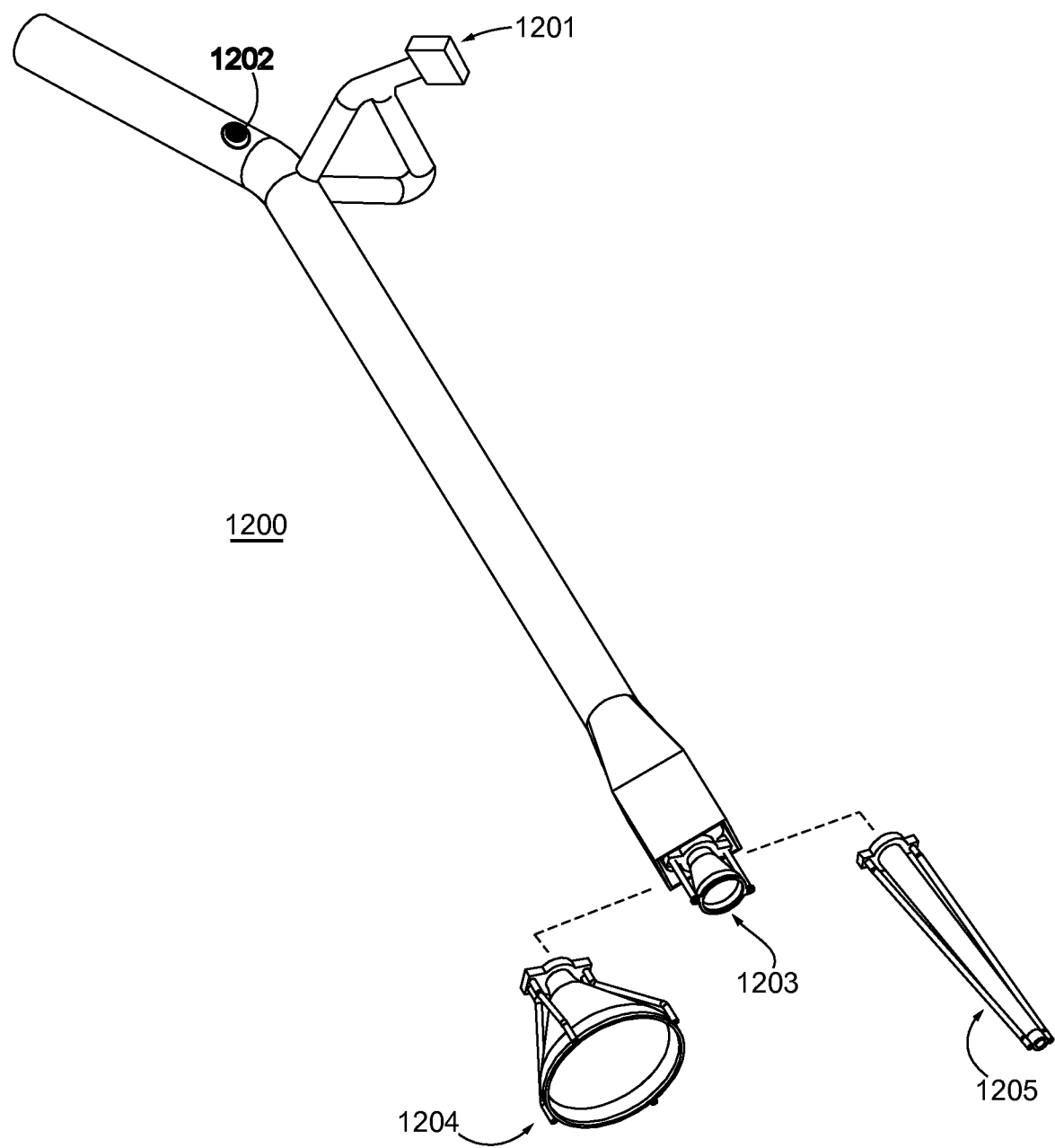
Figure 24:
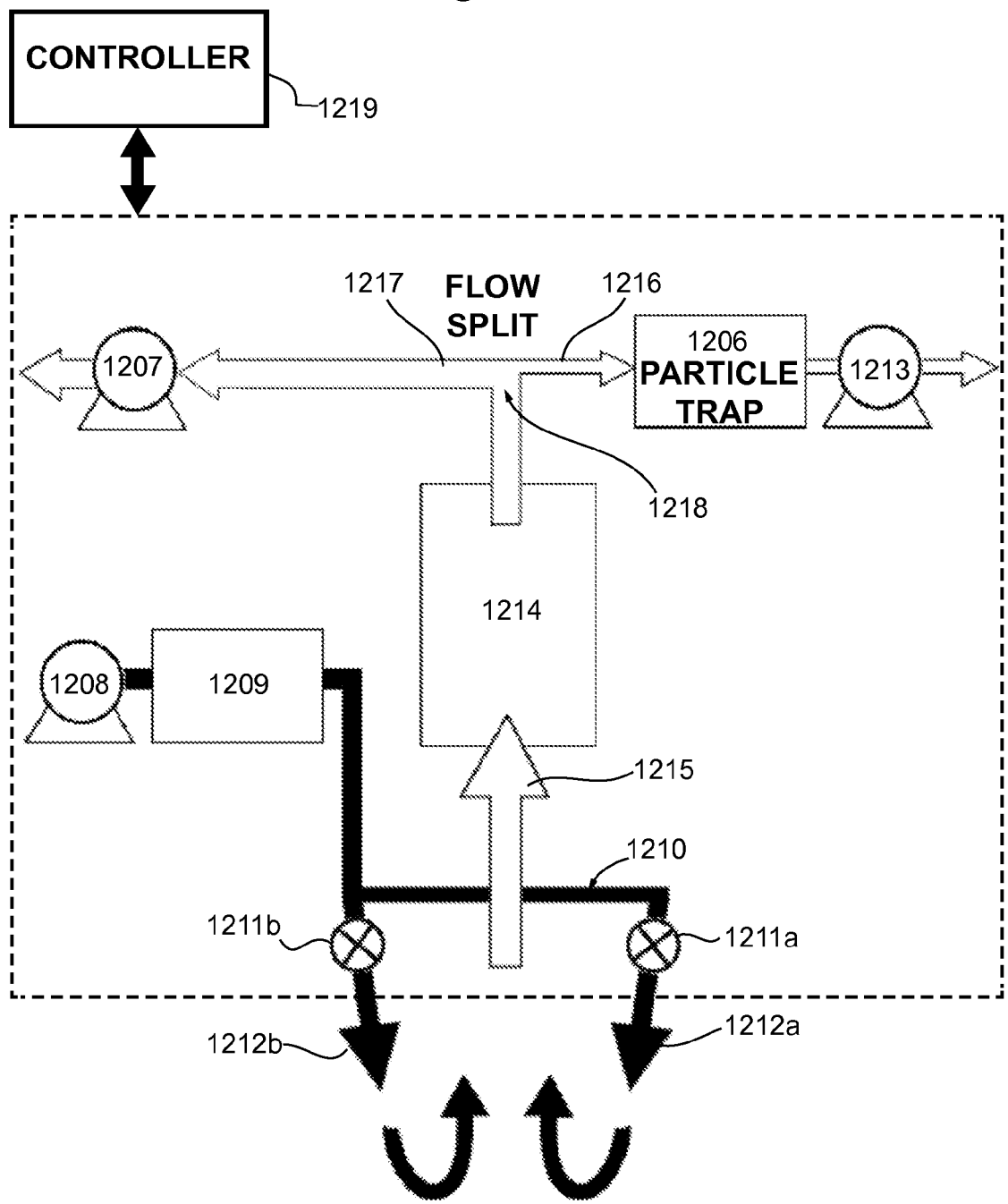

As can be seen from FIG. 21, vapor pressures for explosives and explosives-associated materials vary over many orders of magnitude. Several important classes of high explosives and primary explosives, including RDX, HMX, PETN, TATP, and HMTD, have essentially undetectable vapor components. Taggants have been proposed to facilitate detection of low vapor pressure explosives. Taggants include ethylene glycol dinitrate (EGDN), 2,3-dimethyl-2,3-dinitrobutane (DMDNB), and 4-nitrotoluene (para-NT). These compounds were chosen because they do not occur in nature, they do not tightly adhere to common substrates, and because they continue to release their vapors for 5 to 10 years [J. Yinon. 1995. Forensic Applications of Mass Spectrometry, CRC Press, Boca Raton, Fla.]. Other odiferous "fingerprint compounds" such as cyclohexanone (CXO-used in recrystallization of RDX), benzoquinone, 2-ethyl hexanol (2-EH, used in manufacture of plasticizers), triacetin, and diphenylamine also may be present in significant amounts for detection [Williams et al, 1998, Canine detection odor signatures for explosives, Proc SPIE 35:291-301; WIPO Doc. No. 2010/095123]. These odor fingerprint compounds can be captured for example using gas phase SPME and detected by IMS [US Pat. Doc. 2009/0309016; Perr et al, 2005, Solid phase microextraction ion mobility spectrometer interface for explosive and taggant detection, J Sep Sci 28:177-183; Lai et al, 2008, Analysis of volatile components of drugs and explosives by solid phase microextraction-ion mobility spectrometry. J Sep Sci 31: 402-412]. However, taggants are generally not used by illicit explosives manufacturers and thus any negative vapor detection event must always be viewed with uncertainty.

Vapor traps and particle traps are operated most effectively under conditions that are inherently incompatible. Where vapors are to be collected, very large quantities of air must be sampled, generally more than a single particle trap can readily accommodated in series (with a necessarily higher pressure drop), resulting in larger traps and lower preconcentration. Furthermore, particles interfere with vapor collection, not only because particles adsorb vapors, but also because particles can rapidly foul vapor sorbent beds, poisoning the sorbent and preventing regeneration and cleardown. The excess heat required to fully bake off or incinerate particulates on a sorbent bed can exceed the thermal stability of the resin. Thus the interest in exchangeable cartridges. Although this is a satisfactory solution in some applications, other solutions to the problem of explosives sampling and detection are needed.

Use of upstream air-to-air concentrators has unexpected benefits. Particle-enriched air is supplied to a downstream particle trap at reduced volume, so that the particle trap may be smaller without an increase in pressure drop, resulting in more efficient collection of particles. Routing most of the air away from the particle trap permits higher flow rates in the intake, high enough that elutriative losses of the most information-rich explosives particles (from 5 to 200 microns in apparent aerodynamic diameter) are minimized, an advance in the art.

Air-to-air concentrators may be operated a flow split of 30:1, 50:1, 100:1 or even 250:1 and at particle cut sizes (in the concentrator) of 5 to 10 microns (or even 1 micron if desired), thus shunting very large amounts of particle-depleted air around the particle trap and dramatically reducing the need for a larger particle trap. Operational systems have been achieved at more than 1000 sLpm and are readily scaled for higher throughputs. These flow splits allow the use of much smaller particles traps; the hollow trap volume of the particle traps (i.e., the deadspace volume of the trap) may be reduced to sub-milliliter dimensions in this way. Miniaturization of the particle trap has not previously been realized at high throughput. Stripping operations for harvesting particle constituents from a miniaturized particle trap can be conducted with a correspondingly small volume of stripping agent, resulting in geometric increases in preconcentration and sensitivity.

One implication of this new direction is suggested by FIG. 22, which suggests, paradoxically, that a particle-only detection system with air-to-air particle preconcentrator, when used as one layer of a surveillance network, has increased detection sensitivity for a broader range of explosives than could be achieved with a combined particle and vapor trap operated by thermal desorption. Particles are the primary information-rich content of any sample, and include not only explosives crystals and residues, but also fibers, dust and skin cells saturated with adsorbed vapors from contact with explosives and explosives associated materials (XAM), including taggants. A rigorous, jet-assisted sampling apparatus, with capacity for accumulating particles in a particle trap from a larger volume of aspirated air, will improve surveillance and reduce false negatives.

For example, in a fingerprint containing 100 ng of crystalline explosive (as shown in FIG. 22), solid particles of size greater than 10 microns will contain 85% of the mass (i.e., information content) of the sample. This data is representative of crystals of RDX, HMX or PETN. However, for that same fingerprint where the explosive residue is RDX, the vapors present in a liter of equilibrated air above the fingerprint are expected to have a mass of less than 8 femtograms of explosive. In other words, the solid residues have approximately seven orders of magnitude more mass than the equilibrated vapors, dramatically shifting the probability of detection in favor of the investigator who can detect the presence of particles. Thus the sampling of particles must be a part of any comprehensive surveillance strategy for detecting explosives.

A single particle of diameter of 10 microns may have a mass of about 1 picogram; a particle of diameter 25 microns a mass of about 13 picograms; a particle of diameter 50 microns a mass of about 105 picograms: thus a single particle may be sufficient for detection of an explosive having 200-400 MW—absent any vapor at all.

The relevance of particles in detecting explosives is readily apparent. One technical solution uses an air-to-air particle concentrator for focusing and concentrating particles from a high volume throughput suction intake, accumulating particles (and any adsorbed vapors) from the suction stream in a particle trap, and analyzing only the contents of the particle trap. A real time detection platform for particulate explosives residues at high throughput is achieved by combining jet-assisted aspiration with skimmer-assisted separation of particles prior to particle capture and analysis, and advantageously overcomes technical problems that occur where separation of a particle-enriched flow and a particle-depleted bulk flow is not provided. In this simple and robust system, only accumulated particles are analyzed, but adsorbed vapors on those particles are also detected. For analysis, constituents of interest are typically stripped from the accumulated mass in the particle trap using liquid elution or thermal volatilization. And strategies for selective stripping may be employed to reduce interferents which can degrade sensitivity.

FIG. 23 shows a portable sampling system configured for concentrating, collecting, and analyzing particles. Analysis of particle and particle-associated constituents (such as adsorbed vapors) forms the primary basis for explosives detection in this apparatus. Essentially all of the free vapors aspirated in this system are vented to atmosphere. The sampling apparatus 1200 comprises a wand with handle and control or display interface 1201, jet suction head attachments, each jet-suction head with forward facing jet nozzles and central suction intake, and internal suction pumps for pulling a bulk flow and a particle-enriched minor flow. Interchangeable sampling nose attachments (1203, 1204, 1205) are shown. Particles in a suction gas stream entering the nose are concentrated in an air-to-air particle concentrator and accumulated in a particle trap for analysis at the end of each sampling cycle. A jet pulse actuation control 1202 is used to manually initiate a jet pulse or an analytic cycle.

FIG. 24 is a schematic of the internal pneumatics of a wand or sampler head. Shown are a particle trap 1206, a compressor 1208 and a pressure reservoir 1209 for charging pressurized gas to operate a jet pulse system with distribution manifold 1210, solenoids 1211 for actuating jet pulses 1212, a battery or other power supply, a suction blower 1207 for drawing a bulk flow, a vacuum pump 1213 for drawing a particle beam or ribbon through the particle trap 1206, tubulation for the conveyance of gas flows, control circuitry 1219, and any wiring harnesses as needed for powering and controlling the device. The wand or sampling head also includes an air-to-air particle concentrator 1214 (such as an aerodynamic lens or lens array) used to inertially organize a gas intake stream 1215 into a particle beam or ribbon (comprising the particle-enriched flow, also sometimes termed a "minor" flow 1216) and a bulk flow (also sometimes termed a "major flow" 1217) in combination with a skimmer (also sometimes termed a "virtual impactor" 1218). The skimmer may be of annular or of slit design. The bulk flow is particle-depleted due to the inertial focusing effect of the aerodynamic lens or lens array on particles and is separated from the particle-enriched flow in the skimmer according to a flow split. Inlet particle separators may also be used for separating a bulk flow from a particle-enriched flow according to a flow split. The systems are designed for particle sampling at high volume throughput.

Three pumps are shown and arrows represent gas flows; black arrows indicating positive pressure, open arrows indicating suction pressure. System timing is provided by a controller 1219 which optionally also supplies power to the component subsystems. For purposes of illustration, only two jets and paired solenoids are shown. During sampling, jet pulse outflows 1212 from the forward face or nose of the device are deflected by collision with an external surface and are aspirated, at least in part, as a suction intake flow 1215 through a suction intake in the sampling head and into the air-to-air concentrator 1214. A skimmer 1218 is used to separate the particle-enriched flow 1216 and a particle-depleted bulk flow 1217 at a flow split that is determined by the relative capacity of suction blower 1207 used to pull the bulk flow and vacuum source 1213 used to pull the particle ribbon or beam. The bulk flow contains the majority of the free vapors in the sample. Advantageously, the flow split between bulk flow and particle-enriched flow is typically greater than 50:1 or 100:1 and may approach or exceed 250:1. Pressure drops on the particle and bulk flow sides of the skimmer may be controlled separately.

The particle ribbon or beam flow 1216 is pulled through particle trap 1206 to capture any entrained particulate matter (and adsorbed vapors). The bulk flow is exhausted to atmosphere.

The capacity of a representative suction blower 1207 is typically in the range of 300 to 1500 liters/min at a suction head pressure of 5 inches of water, while not limited thereto. The required flow rates may be achieved with a centrifugal blower such as a Windjammer Model 116630E or a 5.7" regenerative blower (AMTEK Part No. 116638-08, Kent Ohio). The capacity is designed to be effective in aspiration of solid from up to about 1 foot (>30 cm) from the sampler head, typically with jet assist. For portable operation on DC power, a Microjammer 3.3" BLDC low-voltage blower (AMETEK Part No. 119497) may be used. Fans may also be used.

Particle ribbon or beam flow may be powered for example by a diaphragm vacuum pump 1213 such as a BTC-IIS Vacuum Diaphragm Pump obtained from Parker-Hargraves (Model No. C.1C60G1.1C60N1.A12VDC, Mooresville N.C.). Flow rate for the particle-enriched flow downstream from the skimmer is typically in the range of 10 to 15 L/min or less at a suction head pressure of about 20 to 30 inches of water.

Exhaust from the suction blower 1207 optionally may be used to power a curtain air flow through slits mounted peripherally on the sampler head, although not shown here.

Jet pressure is provided by a compressor 1208, typically a diaphragm pump such as a Parker-Hargraves D737-23-01 double diaphragm pressure pump or a Thomas (Part No. 11580056, Sheboygan Wis.). Optionally, any 100-120 psi air pressure source such as compressed air can be used. Pressure is typically accumulated in a pressure reservoir 1009, which may be a tubulation or an in-line tank and is distributed through a manifold 1010 to an array of jets; the manifold is configured to equalize pressurized gas feed to the individual jets.

Solenoids 1211 include Gem Sensors (Plainville Conn.) Part Nos. B2017-V-VO-C111 with a $C_v$ flow factor of 0.43 and 7 Watt coil; D2014-589 (D2014-SB1-V-VO-C111) with 0.21 $C_v$ body and 10 Watt coil; and A2016-V-VO-C111 with 0.24 $C_v$ body and 6 Watt coil operable at 100 psi. Also tested was an ASCO Part No. 8262H112 with a $C_v$ of 0.52 which is also available in DC configuration. These valves were selected for their fast reaction times in order to generate pulses of about 2 to 20 millisecond duration. For general purposes, a 10 ms pulse is useful.

Analytical systems may be supplied on board (not shown) or may be provided at a remote workstation. Thus the particle trap is optionally a cartridge that is placed in the gas flow and removed for analysis. Optionally, the skimmer nose may also be supplied as part of the cartridge and may include integral warming means. In integrated systems, the sampling system also includes an analytic module.

The jet-suction nose on a wand permits directional sampling while advantageously permitting the operator to maintain a distance from the subject, avoid bending over, or gain access to hard-to-reach and tight spaces. The sampling wand may contain a fully functional pneumatic mechanism on board, or may be supported by an umbilicus with pneumatic and/or electrical connections to a cart or a central utility facility. A control console 1219 is generally supplied in association with a handle grip for directing the sampling nose into proximity with a substrate to be sampled, the console with control and display interfaces. Interchangeable nose attachments permit optimization of the sampling regimen for surfaces, corners, baseboards, boxes, enclosed pallets, shoes, hands, and so forth, and are used to optimize the tool for varying sampling tasks.

Also provided are control circuits for powering and controlling operation of the apparatus. Control elements may include a microprocessor or microprocessors, RAM memory, complex logic instructions stored in non-volatile memory (such as EEPROM), optional firmware, and I/O systems with A/D conversion for collecting data and D/A conversion for transmitting instructions to analog subsystems such as pumps and valves and for controlling the flow of power to component systems of the pneumatics and any on-board analytic module(s).

Figures 25, 26:
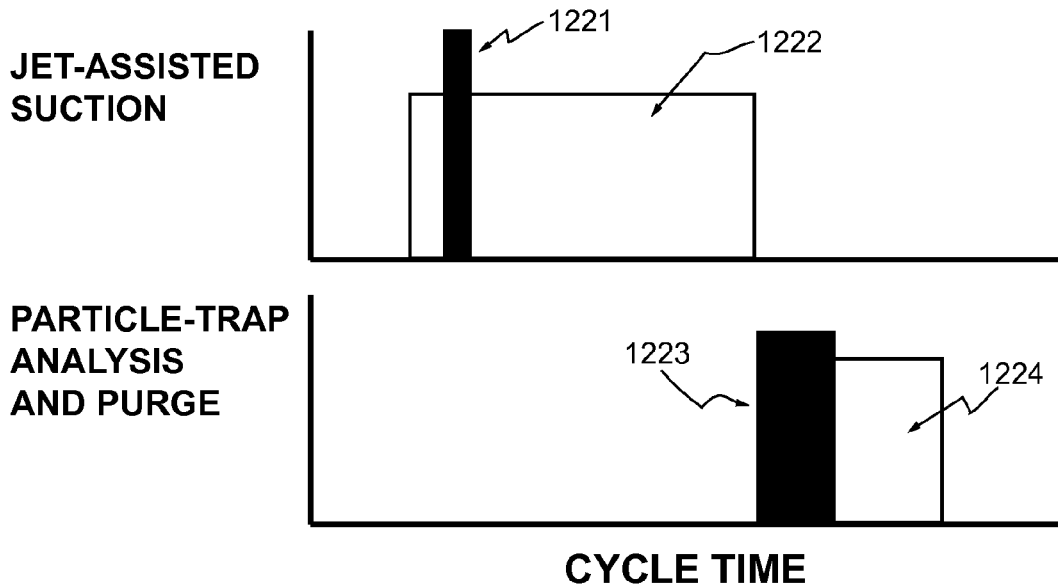

A representative analytical cycle is shown in FIG. 25. Typically suction 1221 is actuated first, followed in a few parts of a second by a jet pulse or pulse train 1222. The substrate being interrogated is agitated and eroded by the jet pulse and particles are mobilized. Fibers or moisture from the substrate are eroded and aerosolized by the action of the jets. These materials are entrained in the suction in-flow and are aspirated into the nose of the sampling head in the first step of obtaining a sample. During suction, particles entering the head are organized inertially into a particle beam or ribbon and diverted to a particle trap, where they are accumulated for the duration of the suction activity. The controller then cycles to analysis mode and any particulate contents of the trap are volatilized or eluted and conveyed to an analytic module for detection of constituents indicating a threat. During the analysis step 1223, the suction and jet flows are turned off. In a preferred mode, analytes captured in the particle trap are "stripped" from the trap and conveyed 1023 to an analytic module. The particle trap is pneumatically (or hydraulically) coupled so that a volume of a carrier gas (or liquid) can be passed through each trap, concentrating the analyte from each trap in a smaller free volume of a carrier for analysis. In the analytic module, analysis and detection of any signal from one or more constituents or analytes is by conventional means. Optionally, all or part of the "strippate" from each trap may be directed to a focusing trap for further concentration before analysis or may be captured on a sorbent for archiving if desired. Various analytes of interest may be selectively stripped from the particle trap by ramping heat or by injecting a series of solvents. Optionally, one or more separate stripping steps are provided to remove likely or potential interferents from the particle trap prior to harvest of analytes of detection interest.

There may also be an in situ detection step that will trigger a more comprehensive analysis. The controller may be programmed to assess the threat from preliminary in situ detection signals and to display an alarm if appropriate. During a cleardown step 1224, the particle trap is purged as necessary and the electronics are cleared in preparation for a next sample. The process of purging the traps and resetting the electronics is termed "cleardown". The apparatus may also display a message if no particulate matter is detected.

FIG. 26 (Table 2) tabulates detection performance for a "particle-only" detection system versus a "vapor-only" detection system, also comparing a thermal desorption-type particle analysis with a liquid elution-type particle analysis. Analytic detection of explosives and explosives-associated materials may be performed with any known detection systems, but for purposes of the table, mass spectroscopy is used. Mass spectroscopy has the capability to overcome the known blindness of IMS and DMS systems to non-nitrogenous materials and may be used with both ion chromatography and liquid chromatography to detect salts such as nitrate, perchlorate, high explosives such as RDX and TATP, and also volatiles such as acetone and diphenylamine. Because of the higher mass of particulates in a sample relative to free vapors, analytes are readily detected even for semi-volatile (high boiling point) compounds such as RDX and also peroxides such as TATP and APNC. Detection of TATP by electrospray ionization mass spectrometry (ESI-MS) is readily achieved [see for example Sigman E et al. 2007. Analysis of triacetone triperoxide (TATP) and TATP synthetic intermediates by electrospray ionization mass spectrometry. Rapid Comm Mass Spec 22:84-90]. For unstable compounds such as TATP and acetone peroxide, liquid extraction is superior to thermal volatilization because peroxides can readily decompose or deflagrate on heating, releasing carbon dioxide as the major decomposition product, which is difficult to detect over background. Hence detection of TATP is marked (±) by hot carrier gas and (+) by liquid extraction in the table of FIG. 26.

Taggants detectable by association with particles include EGDN (decomposes 114° C.) and DMDNB (MP~200° C.). The "stickiness" of these materials to fibers and dust makes them ideal for detection in a particle trap. Taggants such as DMDNB and EGDN are detected by either a particle or a vapor detection system because taggants are incorporated into their explosives substance at 1-5% by mass. Less frequently detected are explosives-associated materials (XAM) such as 2-ethylhexanol (2-EH) and cyclohexanone (CXO). These residues are sometimes constituents of the sample matrix and are just as much an explosives "fingerprint" as any taggant.

TNT is perhaps more readily detected by thermal evaporation as DNT, the dinitro-degradation product, which has a higher volatility, but is also readily detected by liquid extraction in a solvent such as acetonitrile. In contrast, "vapor-only" detection is not fully reliable (±) for TNT, which has a lower vapor pressure than nitroglycerin, and which is difficult to detect at low concentration and in old samples. Sorbent materials used in vapor traps frequent resist releasing larger or more polar molecules; so that much of the TNT in a sorbent bed is effectively lost from detection, and in fact it can be difficult to regenerate a trap that has been exposed to TNT or RDX because of slow persistent bleedout over hours or days, for example. Liquid extraction of solvent bed resin has been accomplished with patience, but is generally considered inferior (not preferred, "np") for routine surveillance because of the time involved in soaking the resin and evaporating the solvent. Certain explosives such as RDX, PETN and TATP, and also HMX are not generally detectable using vapor traps (FIG. 26; not generally detectable is denoted by "−").

By eliminating the need for a vapor trap in the sampling system, much faster sampling turnaround and lower maintenance systems are realized. Even explosive materials such as nitroglycerin and fuel oil (which have characteristic odors) have vapors that associate strongly with particles. Materials associated with NC (nitrocellulose) are more likely to be detected as fibers than as a free vapor. At sufficient temperature, the fibers will release nitrate and any XAM; the nitrate can be detected by luminescence, in an electron capture detector, or by MS with or without ion chromatography.

PETN is also difficult to detect as a free vapor and is best detected as a particle. PETN is used to make C4, Semtex, Hexilene, Plastrite, PE4, and Demex. PETN, however, is commonly formulated as a mixture, and hence should be suspected whenever RDX, TNT, propellants, explosives-associated polymers or plasticizers, or hydrolysis products such as pentaerythritol dinitrate, pentaerythritol mononitrate and pentaerythritol are detected. Also indicative of PETN, are 2-ethylhexanol and phthalates, and the taggants DMDNB and EGDN (where EGDN can be transferred to PETN by shared storage with other explosives). But not all PETN contains taggants, particularly those batches from illicit sources, so direct detection of particles is the most reliable means. Even a non-detection of PETN in the analytic apparatus may be overcome by positive detection of any of a broader genus of explosives or explosives-associated materials in the particle trap, and an explosive device should always be suspected if plasticizers and solvents are detected in the particle trap. The solvent 2-ethylhexanol is frequently used in the manufacture of diester bis(2-ethylhexyl) phthalate (DEHP), a plasticizer commonly found in the matrix of plastic explosives. Complex signatures of selected solvents or plasticizer in the particle trap are not coincidence and can be indicative of a false negative when no actual explosive substance is detected, requiring a more invasive search.

Gunpowder is an interesting case. Potassium nitrate, charcoal and sulfur are not generally volatile, but they are readily detected in liquid by ion chromatography (generally as the oxides), by electrospray mass spectroscopy, or by luminescence of nitrates.

While Table 2 is not intended to be inclusive of all explosives detectable with a system of the invention, one skilled in the art will appreciate that the particle-associated detection patterns are robust and hold for a broad range of explosives, taggants and explosives-associated materials, including not only nitro-, nitrate, nitramine materials but also non-nitrogenous materials. Even when taggants are not present, as in "home-made" explosives, the presence of degradants and chemicals used in chemical processing will yield particle-associated complex fingerprint patterns consistent with explosive devices or recent handling of explosive residues. Devices with machine intelligence for functioning as "learning systems" for predicting the presence of unconventional explosives or suspicious materials (including for example narcotics powders or crystals and large amounts of fibers from cash) from chemical spectrograms are also foreseen. Thus false negatives and false positives are reduced to a small number of instances, a likely advance in the art and much needed for high throughput surveillance such as in airports, ports, and at borders.

Interestingly, liquid elution from a particle trap is expected to successfully detect a full range of potential explosives, explosives-associated materials, and explosives vapors adsorbed to incidental particles such as fibers and skin cells, and has an added advantage that microelution achieves a very high preconcentration factor. This is a technical advance in the art that has not previously been recognized.

Figure 27A:
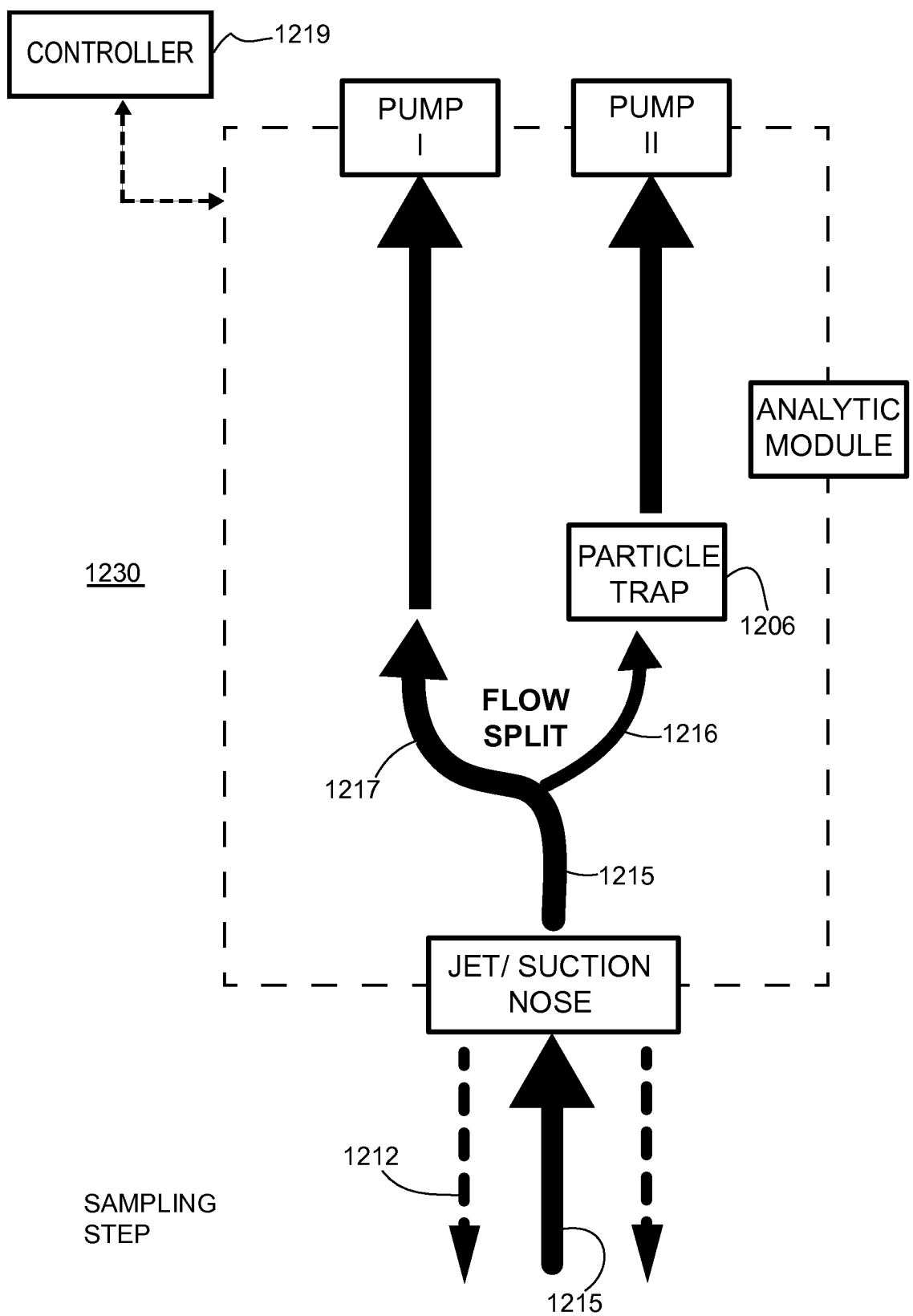
Figure 27B:
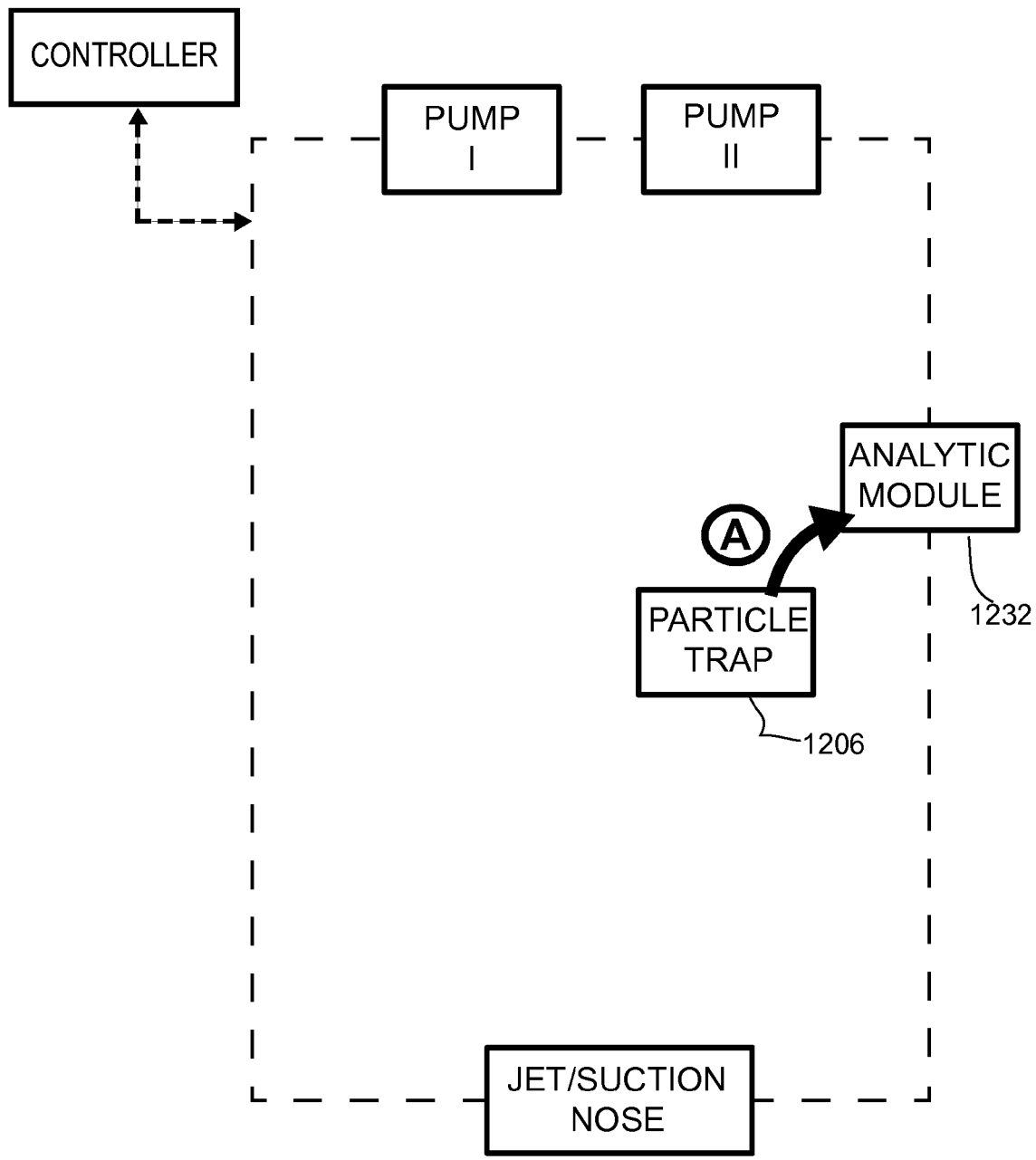
Figure 27C:
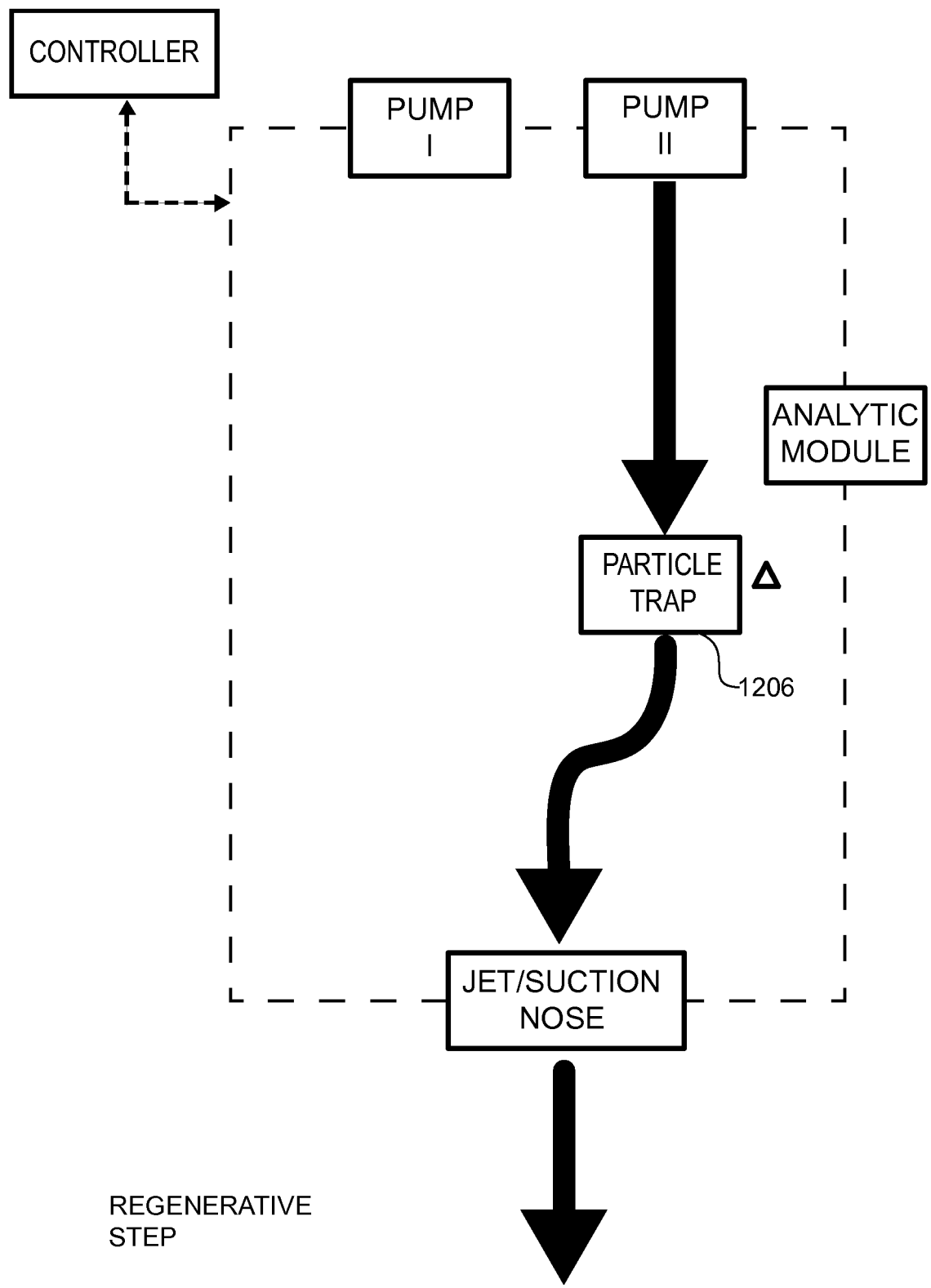

Referring to FIGS. 27A, 27B, and 27C, shown are three schematics depicting the stepwise, cyclical operation of an explosives particle detection apparatus 1230 with a particle trap 1206 downstream from an air-to-air particle concentrator. A sampling and detection cycle involves A) a sampling and capture step, B) an analysis and detection step, and C) a regeneration and cleardown step.

In a first step (FIG. 27A), jet outlets 1212 and suction intake 1215 are actuated by a controller 1219 to mobilize and aspirate a sample at a flow rate sufficient to prevent most particles in the 5 to 100 micron, or even 200 micron, range from settling. These are higher value targets with higher information content because particle solid mass is significantly greater than the mass of any accompanying vapors. The suction intake flow 1215 is focused and accelerated in an air-to-air particle concentrator and split into i) a bulk flow 1217 and ii) a particle-enriched flow 1216 in a skimmer (at the bifurcation indicated by arrows) according to the flow split established by the geometry and the relative suction pressures of Pumps I and II. The bulk flow is directed to atmosphere at low pressure drop and high throughput; the smaller particle ribbon or particle beam flow is directed through a particle trap at a higher pressure drop and a lower throughput. Captive particles accumulate in the particle trap during the suction phase of the analytical cycle.

Next, during an analytical phase (FIG. 27B), constituents of interest are stripped from the particle trap and any matrix materials prior to analysis. Particles and any adherent volatiles may be volatilized in full or in part by heat or are eluted from the particle trap 1206 in a solvent or solvent mixture. Constituents of interest are conveyed to an analytic module 1232 as shown. Comparing a dual particle and vapor analyzer with a device of the invention, the systems complexity is substantially reduced. The analytic module 1232 contains one or more conventional means for analyzing and detecting one or more analytes of interest.

Because the particle fraction is a mixture of materials, desorption temperature is advantageously ramped to selectively volatilize constituents of interest or remove potential interferences such as water. Flash or ramped heating may be supplied by a resistive element, by a strobe lamp, by an IR diode, or by microwaves, and so forth. Peltier devices may be used. Hot gas convective heating may also be used. Alternatively, solvents may be used to selectively elute certain analytes, thus avoiding the need for high temperatures which can damage sensors and sorbents, and can decompose certain substances of interest such as TATP (which degrades ultimately to $CO_2$ when heated) and EGDN.

If a positive signal is detected in the analysis step, an alarm is sounded. If the analysis is not conclusive, any harvested constituents may then be transferred to a secondary detection system for secondary inspection, or a sample can be archived in a cold trap for subsequent forensic analysis.

By selecting a primary detector for speed of analysis, large numbers of boxes or articles can be surveilled, working the sniffer between the items, and individual items associated with a signal above background are readily tagged for further inspection.

In a third stage of a sampling/analytical cycle, the particle trap 1206 is regenerated if necessary as depicted in FIG. 27C. Heating with reverse flow is the most direct means of purging the particle trap. Ports to the analytic module and between the particle and vapor trap are closed and the pump exhausts are engaged so as to flow clean air through the sampler head, preferably in a reverse direction, clearing any volatiles and deposited materials from the traps, associated channels and internal surfaces of the device. Particle traps having heat resistant construction may be incinerated to ash common contaminants such as dust or cellulose fibers that would otherwise clog the trap. Liquid flush solutions may also be used. Embedded ultrasonic or microwave cleaning elements are also assistive in clearing the traps of any interferents before a next sample is collected. Means for stripping generally have application for purging and regenerating the traps. Electronics are also reset during cleardown.

More detail of a particle concentrator and particle trap assembly is shown in FIG. 28. The sampling head combines an aerodynamic lens for focusing a particle-rich core flow and a skimmer for separating the particle enriched flow and a particle depleted bulk flow. The lateral arms of the skimmer are for receiving the bulk flow; the skimmer nose is formed around a virtual impactor and collector duct, and a particle trap is disposed in the collector duct.

Figure 28A:
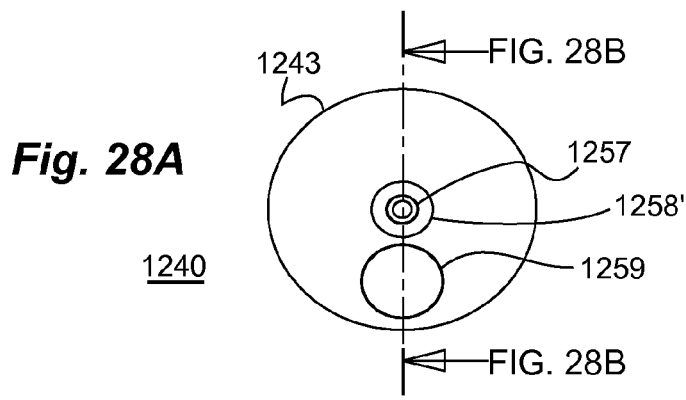
Figure 28B:
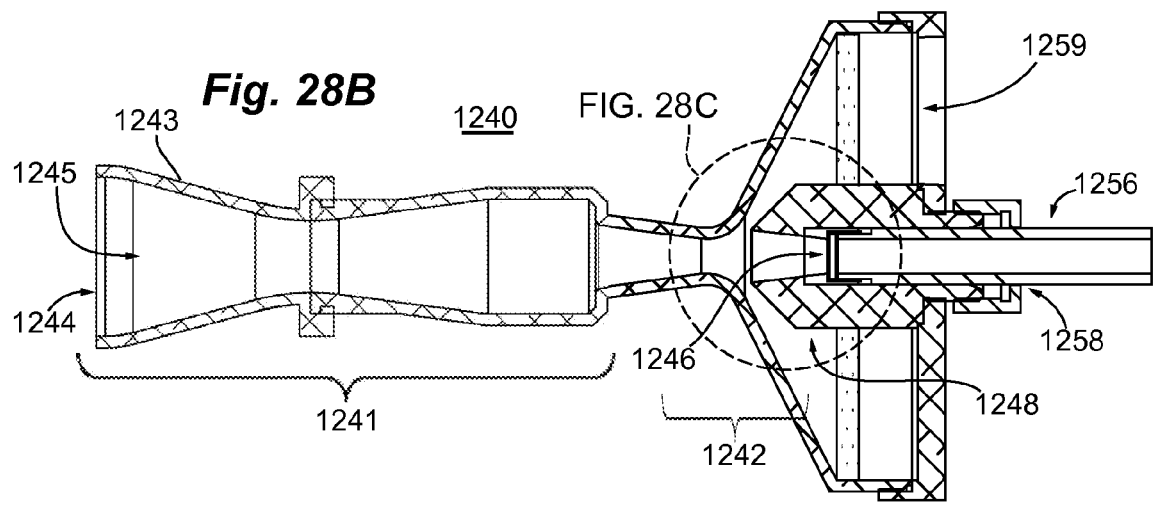

FIGS. 28A and 28B are plan and cross-sectional views of a sampler head 1240, with particle concentrator (1241, 1242) having a sampling bell 1243 with suction intake 1244 connected to a central channel 1245. A particle trap 1246 is positioned downstream from the skimmer to intercept and capture the particle concentrate. Optionally the sampler head can be mounted on a wand as shown in earlier figures.

Figure 28C:
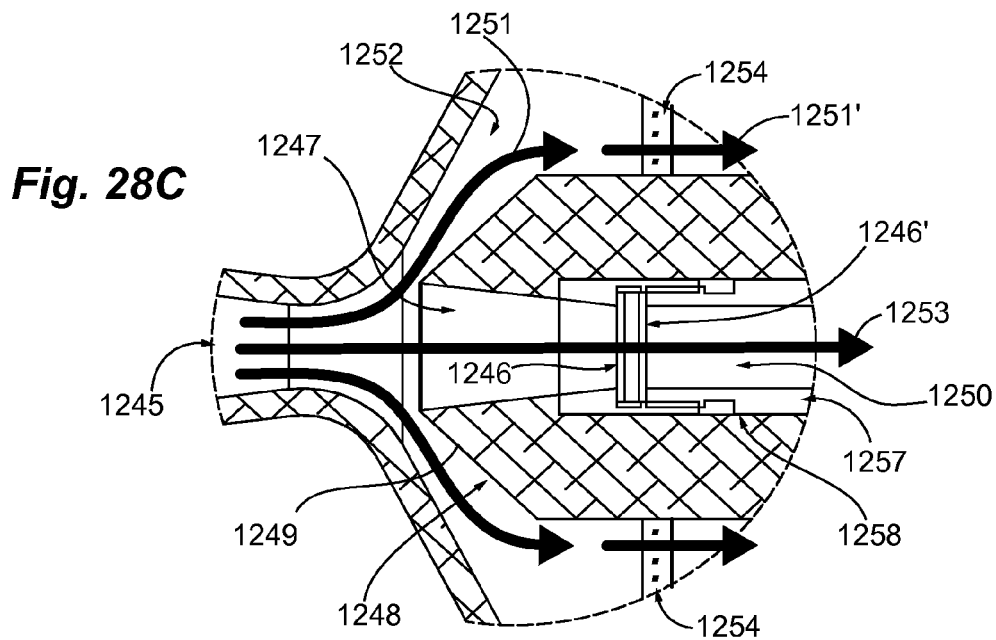

As shown in more detail in FIG. 28C, particles are concentrated as a particle beam or ribbon of flowing gas by the focusing action of one or more aerodynamic lens elements 1241 lining the central channel. The gas stream is accelerated as the channel narrows upstream from the skimmer 1242 and encounters a virtual impactor 1247 with skimmer body 1248, skimmer nose 1249, and collector duct 1250. The bulk flow 1251 streamlines are deflected on the skimmer nose 1249 into lateral flow channels 1252 while the particle-enriched flow 1253 with particle concentrate flows into the mouth of the nose, also termed the mouth or void of the virtual impactor 1247. The particle-enriched stream is then stripped of particles by impactor 1246 with multiple layers of mesh 1246' before exhausting through collector duct 1250.

Downstream pumps for pulling the bulk flow 1251 and the particle concentrate flow 1253 are separately controllable. The downstream pressure drop in each channel establishes a flow split between the two flows and also the overall suction intake rate and velocity. Baffle element 1254 equalizes the pressure drop in a plenum formed by the lateral flow channels; exhaust gas 1251' is directed to a single port 1259 connecting to the suction blower 1207.

The particle trap 1246 shown here is built as a cartridge assembly 1256 constructed to be withdrawn from the apparatus. The cartridge comprises a cylindrical sleeve 1257 and inserts into a receiving port 1258 with cap 1258' at the base of the sampling head. The receiving port is co-axial with the long axis of flow of the particle beam. The cartridge is removable for remote analysis or archiving.

FIG. 29 is an exploded view of a removable cartridge subassembly 1256 as mounted in the sampler head. The nose end 1260' of the skimmer body 1260 is formed with a collector duct 1261 and virtual impactor void 1262 for receiving a particle beam. The nose end is shown here with conical forward face for diverting the bulk flow around the nose. The skimmer body is enclosed in a housing (not shown) which channels the bulk flow through exhaust port 1263 in coverplate 1264. The coverplate, forming the back side of the particle trap, is removable. Only a half a coverplate is shown for purposes of illustration. The particle beam with associated air flow is directed axially through particle trap member 1246, which includes as shown here three layers of non-conductive mesh. The trap, a capping thimble nut 1256a and tubular sleeve 1256b form cartridge assembly 1256. Flow is exhausted at rightmost axial port 1265. Rearmost nut 1266 secures the tubular sleeve to the coverplate, and is threaded for removal. The internal sleeve, cap and particle trap (i.e., cartridge assembly 1256) are removable for remote analysis or archiving. The concentrated volatiles or eluate from the particle trap cartridge may be presented to an analytic module off line for detection of explosives residues.

Pervious filter or mesh members 1246 generally are heat resistant and are selected from glass or ceramic where electrical interference is to be avoided, such as for certain in-situ detectors. However, conductive stainless steel or carbon materials may also be used if desired. Encased carbon fiber materials may also be used as a coarser supporting matrix to improve heat transfer. In special circumstances, such as disposable cartridges, plastic filters or meshes may be used, and analytes may be stripped from the plastic with vapor or solvent rather than by heat treatment if desired.

Figure 30:
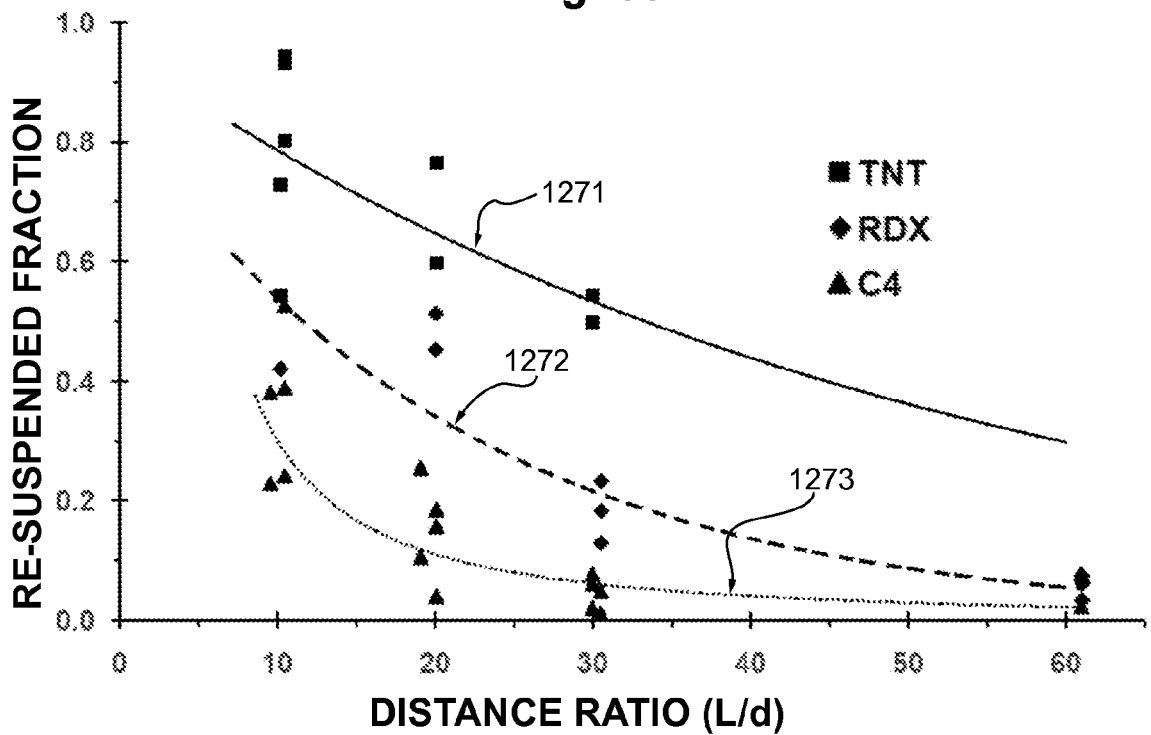

FIG. 30 demonstrates particle mobilization and aerosolization with a jet-assisted suction head of the invention. Experimental data are plotted for jet aerosolization of solid explosives residues from a surface. The data was collected using the widemouth sampling bell of FIG. 36 and illustrates the effect of the distance ratio L/d on resuspension efficiency, where an explosives residue is applied to a surface and the residues are mobilized and eroded by the action of the jet pulse and then aspirated under suction.

Under choked flow conditions with fast valve actuation, jet pulse energy may be varied by selecting nozzle size (or critical dimension). Nozzles may be circular or may have asymmetrical shapes, such as fan or chisel shapes. Data shown is for a series of circular nozzles. The distance ratio is defined as L/d, where L is the distance between the jet nozzle orifice and the substrate and d is the critical dimension of the jet nozzle. The ratio is found to have a correlation with particle removal efficiency and can be seen to scale linearly. At length/diameter ratios of 30×, recovery is still sufficient to detect all three explosives. At 10× jet length to diameter ratios, recovery (1271, solid line) approaches unity for more crystalline materials such as TNT, but is less for C-4 (1273), which is a plastic explosive and is more clay-like, containing aliphatic oils which are sticky. RDX, the active crystalline component of C-4, is shown to be more readily aerosolized (1272). Studies by others have shown that fingerprints of persons handling RDX and C-4, for example, typically contain crystals larger than 10 microns, and these crystals contain most of the total mass, underlining the value of collecting particulate solids.

Figure 31:
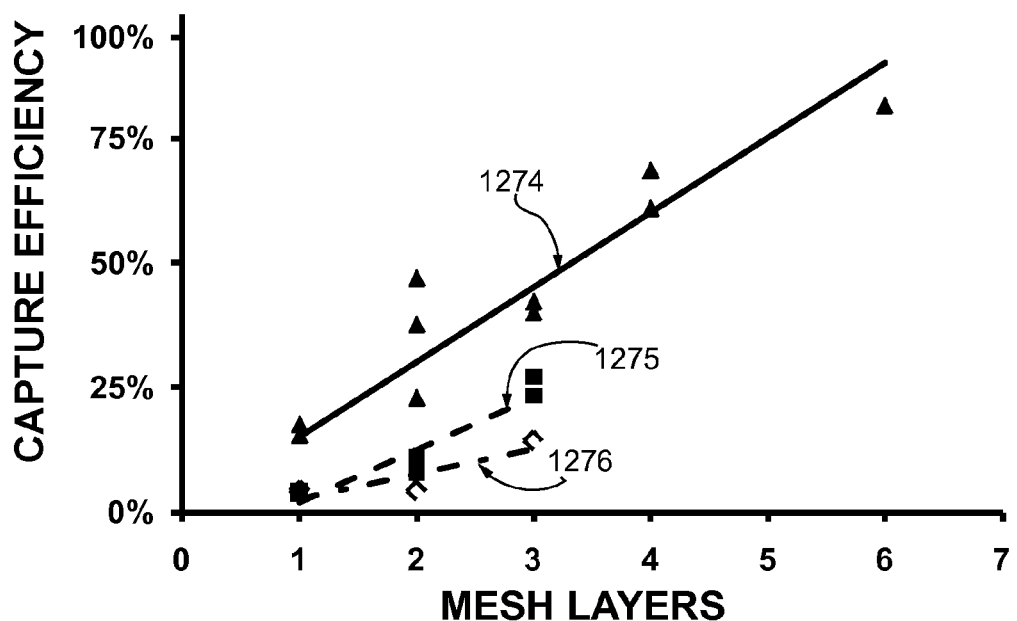

Effects of number of layers of filter or mesh on particle capture efficiency are shown in FIG. 31. Mesh illustrated here may be one, two, three, five or seven layers thick for example; exhibiting increasing efficiency of capture. Capture efficiencies approaching 100% can be obtained; coarse mesh in fewer layers has lower efficiency than finer mesh in multiple layers. Experiments were performed with dried crystalline residues of TNT 1274 applied to a surface and sampled. Similar experiments were performed with RDX crystals 1275 and with C-4 1276, a more sticky substance which contains plasticizers.

Because the bulk of the air volume aspirated has been diverted in the skimmer, lower pressure drops, smaller particle traps, and higher particle capture efficiencies are achieved.

Figure 32:
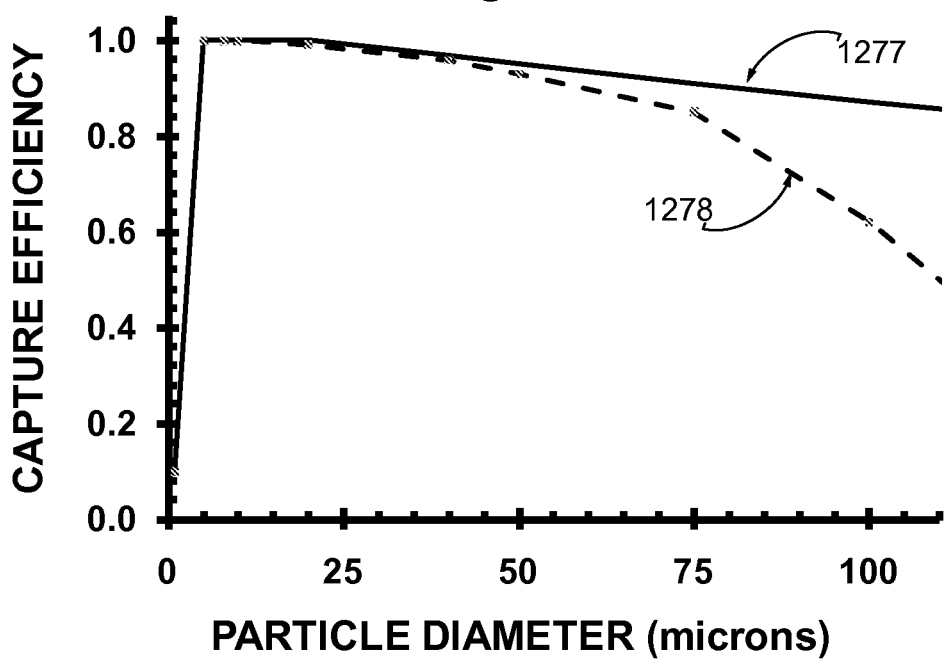

Particle capture efficiency is negatively impacted by particle scattering and elutriative losses. FIG. 32 demonstrates the effect of settling in flight on capture efficiency. When operating at distances of a few inches or more than ten to twelve inches from a suspicious residue, particles dislodged by a jet pulse can be drawn into a suction intake but will also tend to resettle. Elutriative effects are readily apparent for larger particles and higher density particles. The solid line 1277 indicates capture efficiency in a particle trap with a cut size of about 5 microns when the sampling head is held vertically downward; the dotted line 1278 when the head is horizontal to ground plane. Whereas capture efficiencies are quantitative for the vertical orientation in the range of 10 to 40 microns, a small loss of sampling efficiency is noted in the horizontal head position. These data are taken at a suction intake rate of 800 sLpm in a conical head with a 5.5" mouth. More significant losses are noted at slower suction intake rates. Higher collection efficiencies are achieved at higher velocities in the intake bell or nose.

For portable surveillance systems, it would be common for a sampler head to be held at a somewhat horizontal orientation. The data indicate the need for higher linear flow velocities in the intake nose to minimize settling dropout. In heads with bell size maximal diameter of greater than about 5 inches, for example, a linear in-flow velocity is at least 0.8 m/is deemed sufficient to efficiently aspirate the majority of particles of 5 to 100 microns aerodynamic diameter without major settling losses. Higher linear intake velocity with acceptable pressure drops across a smaller cross-sectioned particle trap is realized, happily, by inserting an air-to-air particle concentrator between the suction intake and the particle trap. Further increases in volume throughput may be achieved by reducing the pressure drop for the bulk flow and by increasing the flow split.

Figure 33:
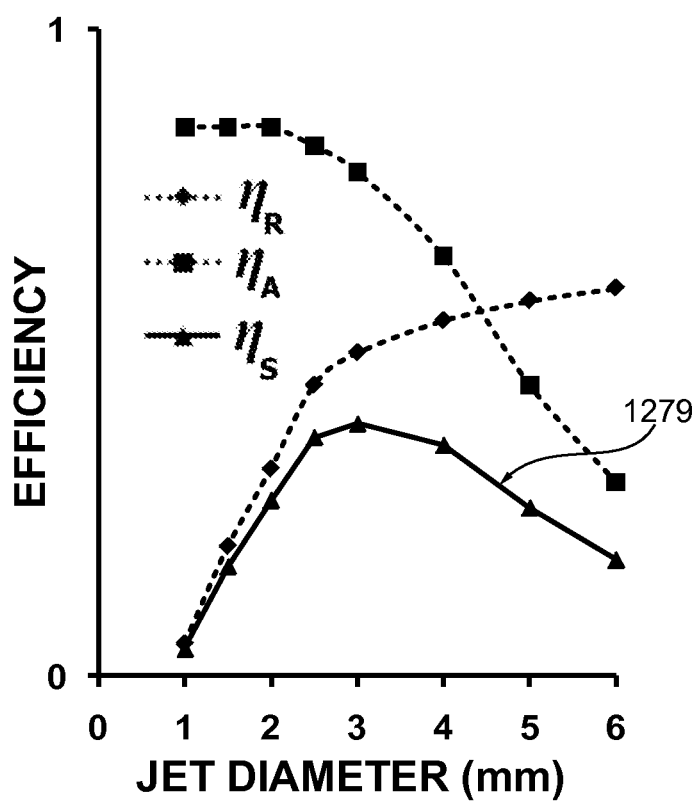

Efficiency data are useful in optimizing jet and suction configurations for efficient particle resuspension and aspiration. FIG. 33 plots optimization of jet diameter by measuring overall sampling efficiency $\eta_S$ (1279, solid line) for explosives residues from a solid surface at a constant distance. Even at distance ratios of 30× or 40× nozzle diameter, however, removal efficiency is a substantial percentage and particulate and particulate-associated explosive residues are readily detectable.

As jet diameter increases under choked flow conditions, particle removal efficiency $\eta_R$ is seen to increase, indicating greater kinetic energy of the jet pulse; however, aspiration efficiency $\eta_A$, indicating particle capture, decreases almost inversely, indicating that particles are scattered outside the sampling zone. In this example there is an optimum balance, as seen by a peak in overall sampling efficiency $\eta_S$ is apparent at a jet diameter of about 3 mm. This result has been repeated under a number of experimental conditions and represents a useful approach for optimization of sampler head configuration.

Figure 34A:
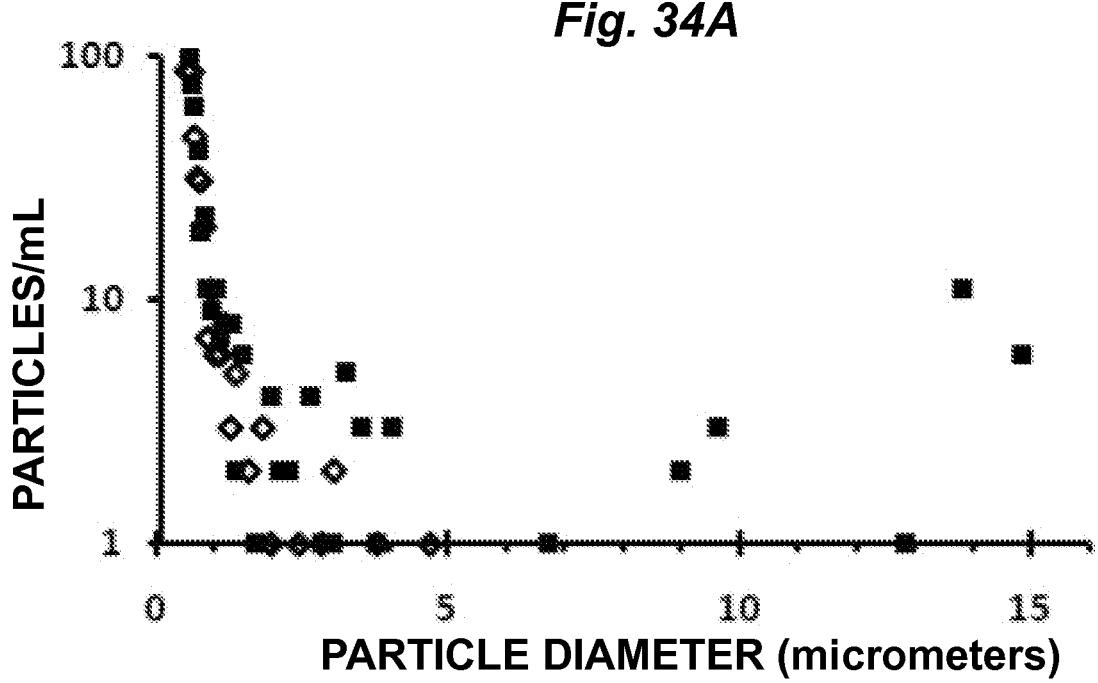
Figure 34B:
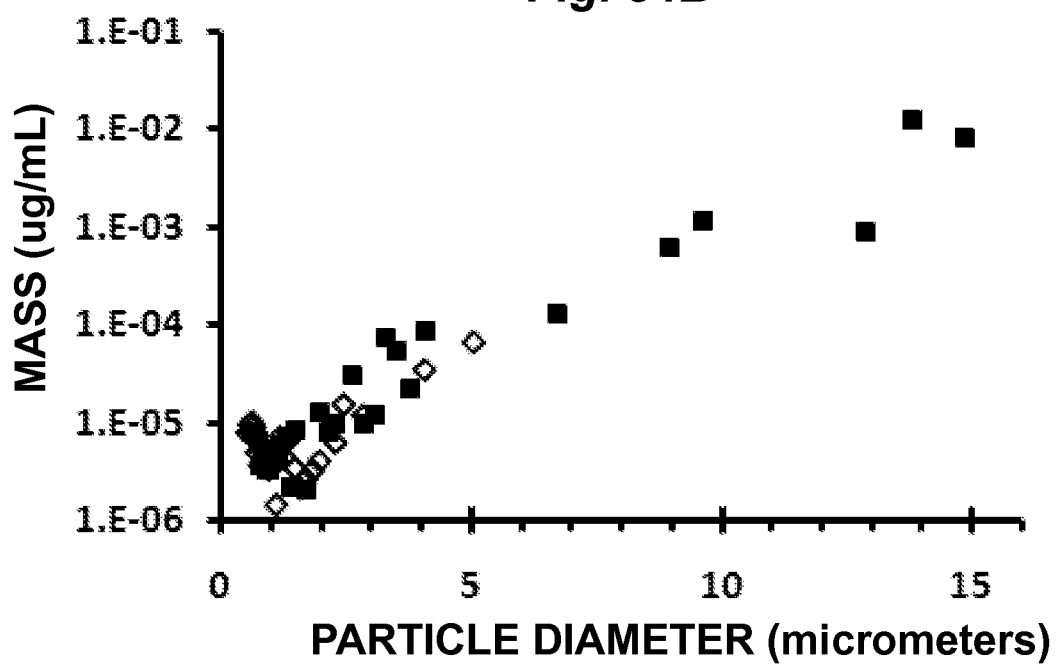

The force of the jets in eroding materials from a surface is illustrated in FIGS. 34A and 34B. Aerosolization of standing water on a surface with a three millimeter jet array at a standoff of 6 inches is shown. Open diamonds indicate background particle content of aspirated air as measured with a laser scattering particle counter. Solid squares indicate aerosolized material from the same surface with standing water after impact of a single jet pulse. The increment in particles detected, FIG. 34A, indicates an increased concentration of 10 and 15 micron particles (i.e., mist) in the aerosol sampled from the wet surface. Similarly, in FIG. 34B, overall aspirated mass is greater from the wet surface, indicating that standing water is aerosolized by the impact of the jets and microscopic water droplets in the 5-15 micron range are aerosolized in this way and may be sampled in the suction in-flow of the sampling device. The force of the jets is graphically illustrated and demonstrates the beneficial erosive effects of high velocity gas jets in obtaining samples from contaminated surfaces.

Figure 35:
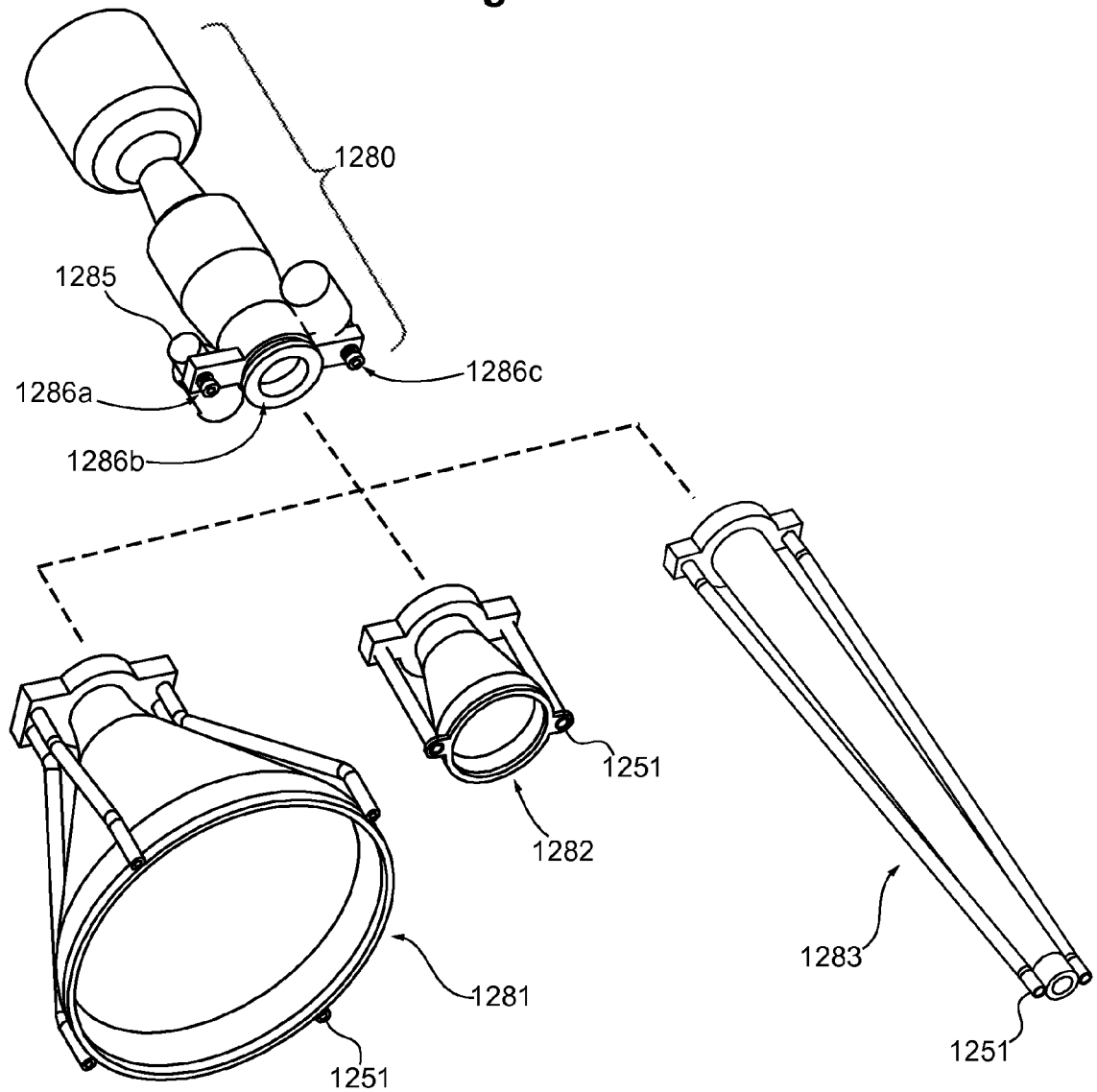

Interchangeable detector heads are provided, as is useful to increase flexibility in use. FIG. 35 shows a sampler head 1280 having three interchangeable nose attachments (1281,1282, 1283). Each tool is adapted to a particular kind of sampling, a first nose attachment 1281 with four jets 1251 and a wide intake bell for surface sampling (generally for fixed or robotic emplacement), a second attachment 1282 with smaller intake bell and two jets 1251 for portable use in surveilling surfaces, and an extended narrow nose 1283 with paired jets 1251 for interrogating narrow or hard to reach spaces. The "general purpose" interchangeable head depicted centermost is also useful for surveillance of persons and can be directed at clothing, hands, shoes and so forth.

The narrow elongate nose 1283 depicted rightmost in FIG. 35, is useful for probing narrow cracks, corners, and also for insertion into holes such as through a layer of shrink wrap surrounding goods on a pallet, where the enclosing wrapping layers ensure that particles and vapors that are mobilized by the jet pulse are not scattered away from the suction intake but are instead deflected into the suction intake.

Figure 3A:
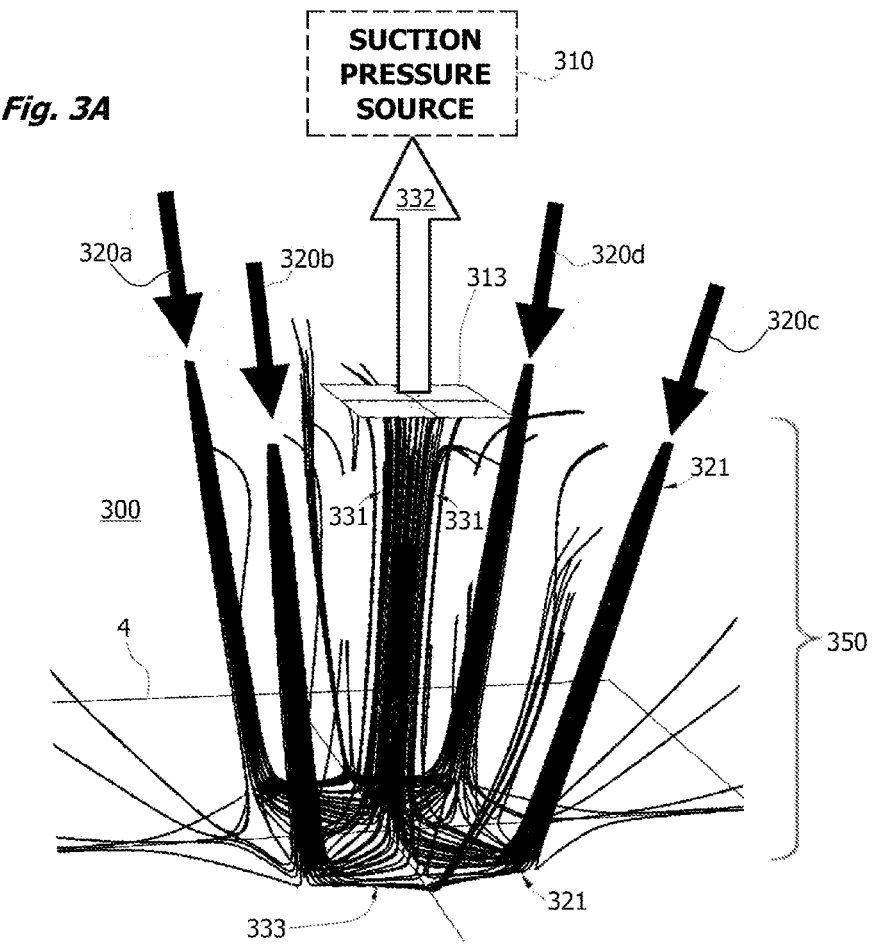
FIG. 3A is a computational model of a four-jet virtual sampling chamber formed by a sampler head of a device of the invention. The lines represent streamlines of air.
Figure 3B:
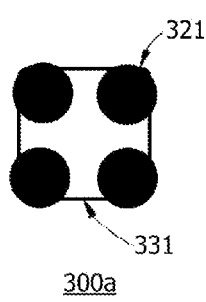
FIGS. 3B through 3D depict the footprint on the interrogated surface established by various configurations of jets, showing quad-, tri- and octa-jet configurations.
Figure 3C:
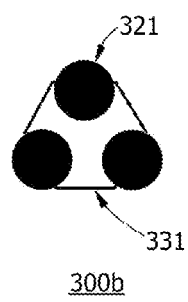
Figure 3D:
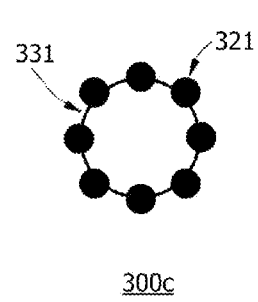

Nose attachments with four jets and two jets are shown, but the number of jet nozzles (1251) may be varied as indicated in FIG. 3B-3D or reduced to two jets or even one jet where it is desirable to insert the sampling nose into a tight space.

The sampler head body 1280 generally also includes any control mechanisms for pulsatile emission of jets (here a pair of solenoids 1285 are shown), any pressure reservoir and manifold useful for supplying and distributing pressurized gas feed to the jets, an air-to-air particle concentrator, a collector duct, pumps and any power supplies as required. Thus any wiring connections need not extend into the sampling nose attachments. The body is provided with a generic interconnect mechanism (here three nipples 1286a,b,c) so that each of the nose tools are engaged with a sealed and air-tight connection. Other suitable connectors are known in the art.

For enclosed spaces, two jets are typically sufficient although it may be desirable to control or vary jet incidence angle to better sample the walls of any crevice or cranny that is being interrogated. For larger surfaces and for situations where a sampler head traverses a surface (or a surface is moved beneath a sampler head) four, six or eight jets may provide additional efficiency in particle removal.

Because the jet pulses have a kinetic energy, any flexible walls or wrappings of parcels, letters, luggage and boxes are readily collapsed by the propulsive force of the jet and then reflated under vacuum, causing fractions of air to be expelled from inside the package or bag. Serial pulse trains are particularly useful in exploiting this percussive effect. The jet-suction head thus is superior to plain suction in mobilizing residues from inside parcels. In this way, false negatives are more readily avoided.

Figure 36:
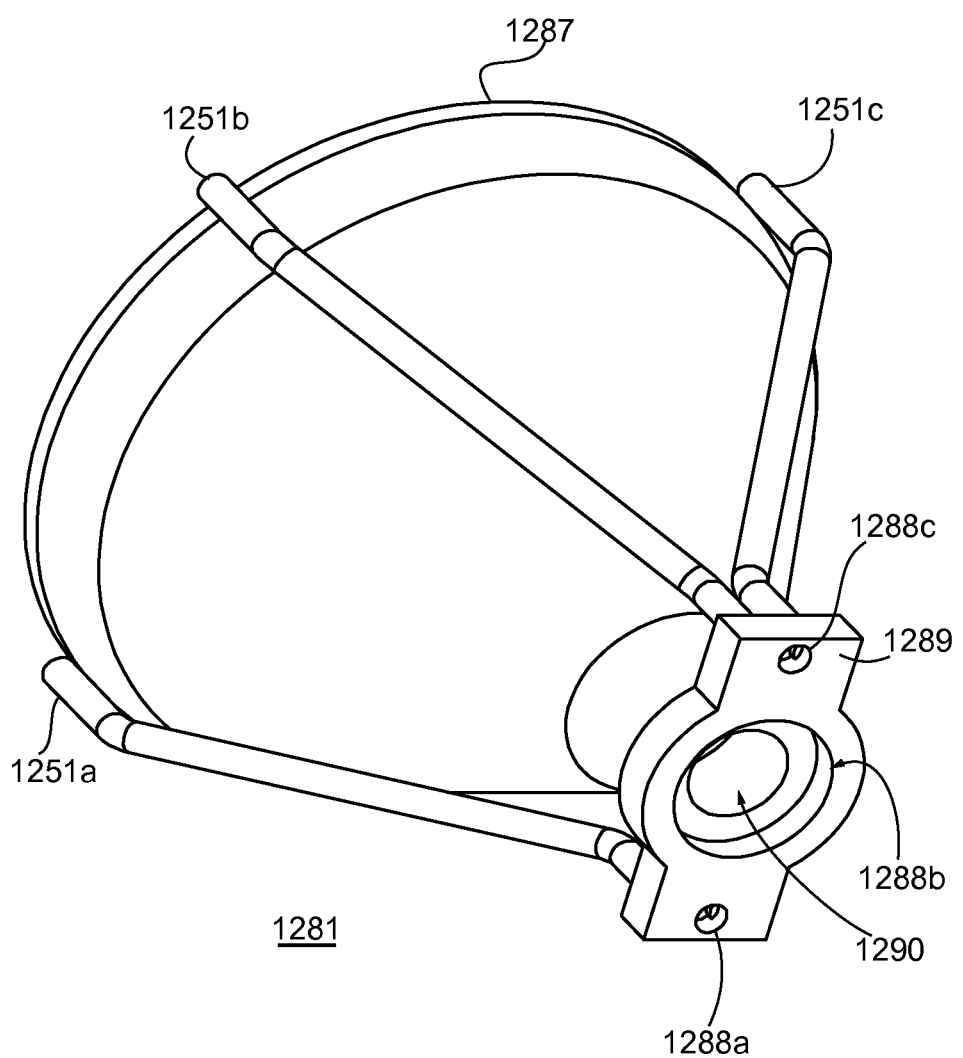

FIG. 36 is a first sampling nose 1281 configured as a widemouth surface sampler with quad jets 1251a,b,c mounted on a sampling bell 1287. In this view, the sampling end of the bell is pointed away so that an interconnect manifold 1289 is visible. Gas entering the sampler head at ports 1288a,c is distributed to each of the four jet nozzles mounted on tubulations around the bell. When attached, central intake 1290 with socket 1288b is in fluid communication with the air-to-air particle concentrator and the suction blower.

In one realization, the widemouth bell has an internal diameter of about 5.5 inches at the inlet end and a conical profile, terminating in central intake duct 1290 with an internal open diameter of about 1.77 inches. The suction velocity at the wide end (of the sampler cone is about 1 m/s at 1000 L/min. The suction velocity at the narrow end (1.77 inch diameter) of the cone, at the point of entry into the particle concentrator, is about 10 m/s under these conditions.

Aaberg lateral flows may be employed to extend the forward reach of the suction low pressure zone and more parallelly align in-flow streamlines. Since a large-volume regenerative air flow is readily available for feeding lateral flows (the bulk flow exhaust from the sampler head), the Aaberg effect can be readily achieved at little to no energetic cost for device operation.

Figure 37A:
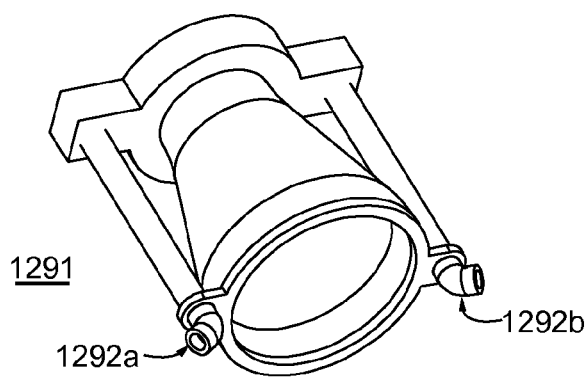

FIG. 37A illustrates a sampling nose 1291 modified for sampling from crevices and enclosed volumes, where the jet orifices are provided with directional jet nozzles 1292a,b. Jet nozzles with other angulations and shapes may be used. For interrogation of tight and enclosed spaces, which may be spaces between or inside boxes, under pallets, along the baseboards of walls, and inside trunks of cars, for example, the jet will impinge on the surrounding surfaces with a variable angle. Because of the enclosing geometry of the sampling space, the dispersive angle of the jets is not an impediment to aspirating materials that are dislodged.

Figure 37B:
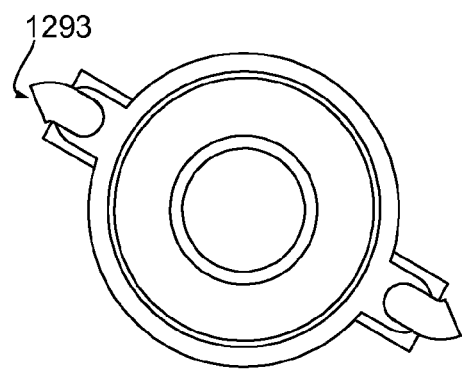

As suggested by FIG. 37B, the jets can be configured with a compoundly bent directional nozzle 1293 to propel the sampling nose in a spinning, circular motion so as to dislodge residues from the surfaces enclosing a space.

Figure 38A:
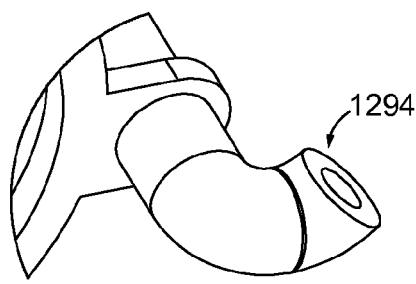
Figure 38B:
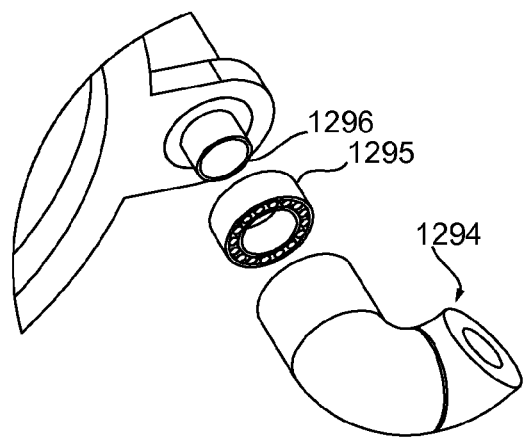

FIGS. 38A and 38B are perspective and exploded views of a spinning jet nozzle. The directional nozzle 1295 itself may spin, for example a jet nozzle having journalled surfaces and bearing means for rotating, where a complexedly bent jet nozzle 1294 is mounted with needle bearings 1295 on a journalled nipple 1296 and fluidly supplied with pressurized air so that it spins in reaction to the jet pulse exhaust. When sampling in enclosed spaces, an actively spinning jet with variable incident angle is an assist in dislodging and mobilizing materials from various surface orientations encountered as probe advances. The angle of the jet may be orthogonal to, oblique to, or, more preferably, acutely angled relative to the directional axis of the sampling nose at any given time. Alternatively, the head may be fitted with flexible hose tips as varidirectional jet nozzles for sampling enclosed spaces. The flexible hose tips have a elasticity that promotes a whip action that promotes mobilization and erosion of any particulate or vapor analytes on the walls or floor of the enclosed space.

Figure 39:
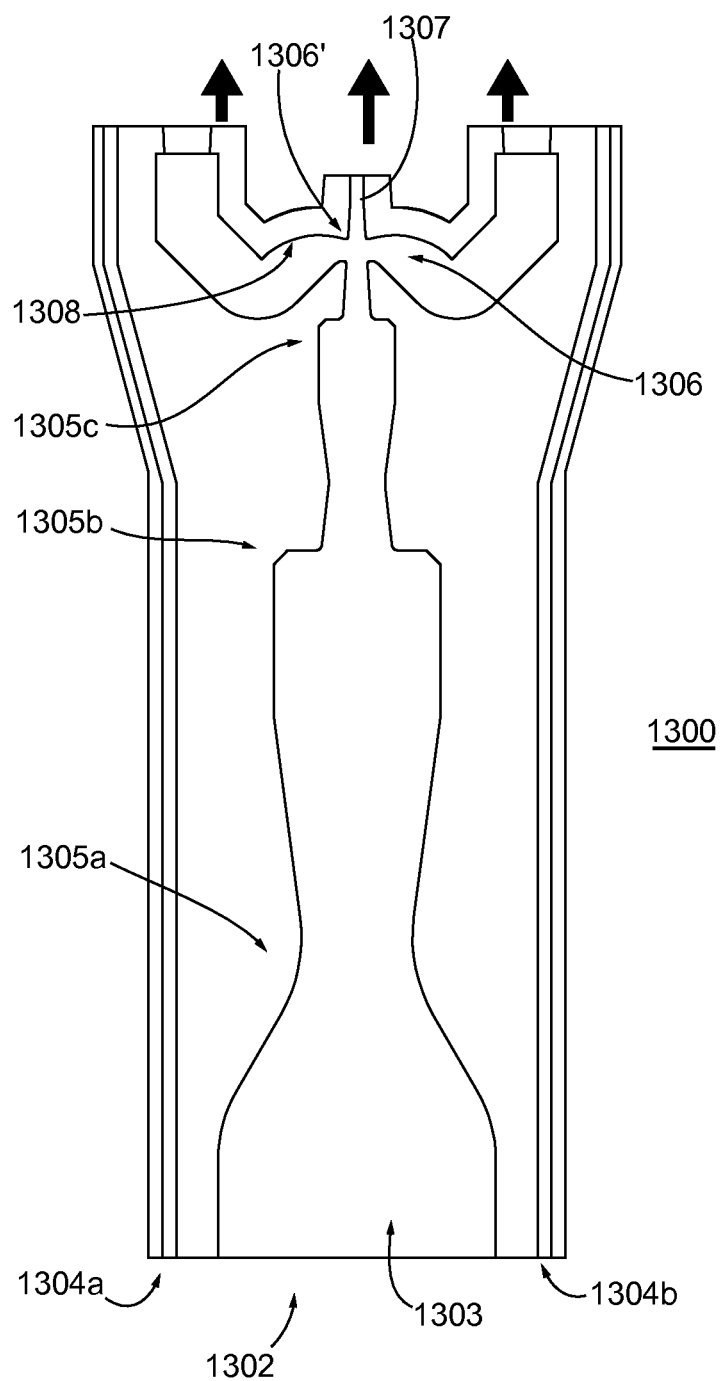

FIG. 39 is a view of another sampler head 1300 with internal pneumatics shown. The forward face 1302 of the jet-suction nose, which may be directed into a narrow crack, corner or orifice, contains a central suction intake 1303 and a pair of peripherally disposed jet nozzle outlets 1304a,b. Emitted jet pulses are directed with a forward velocity and strike any exposed surfaces within proximity, dislodging adherent materials and stripping away any vapors in the boundary layers. The entrained materials are pulled into the suction intake by a suction blower operatively connected to the sampler head. The suction intake flow is formed into a particle-enriched flow and a bulk flow by the action of aerodynamic lenses (1305a,b,c) and the progressively narrowing intake channel which functions as an accelerator. A slit-type skimmer 1306 is used to separate the particle ribbon flow from the bulk flow. Particles are directed into a collector duct 1307 and accumulate in a trap downstream from the skimmer for periodic analysis.

Functionality of skimmers having concavoconvexedly reverse curved lateral channels 1308 for the bulk flow is described in more detail in U.S. Pat. No. 7,875,095 and co-pending U.S. patent application Ser. No. 12/964,700, which are co-assigned and are incorporated in full by reference.

Briefly, the downstream walls of the lateral channels 1308 are shown to support the bending streamlines of the bulk flow in turning more than 90 degrees from the long axis of flow of the gas streamlines in the suction intake, the downstream wall support serving to reduce eddies and wall separation instabilities so as to promote a cleaner separation of the bulk flow from the particle-enriched flow. The bulk flow and particle-enriched flow streams diverge above the virtual impactor mouth, shown here with a generally "cross-tee" configuration 1306' with four channel arms in section. This geometry is useful for both slit-type and annular (axisymmetrical) skimmers.

Figure 40A:
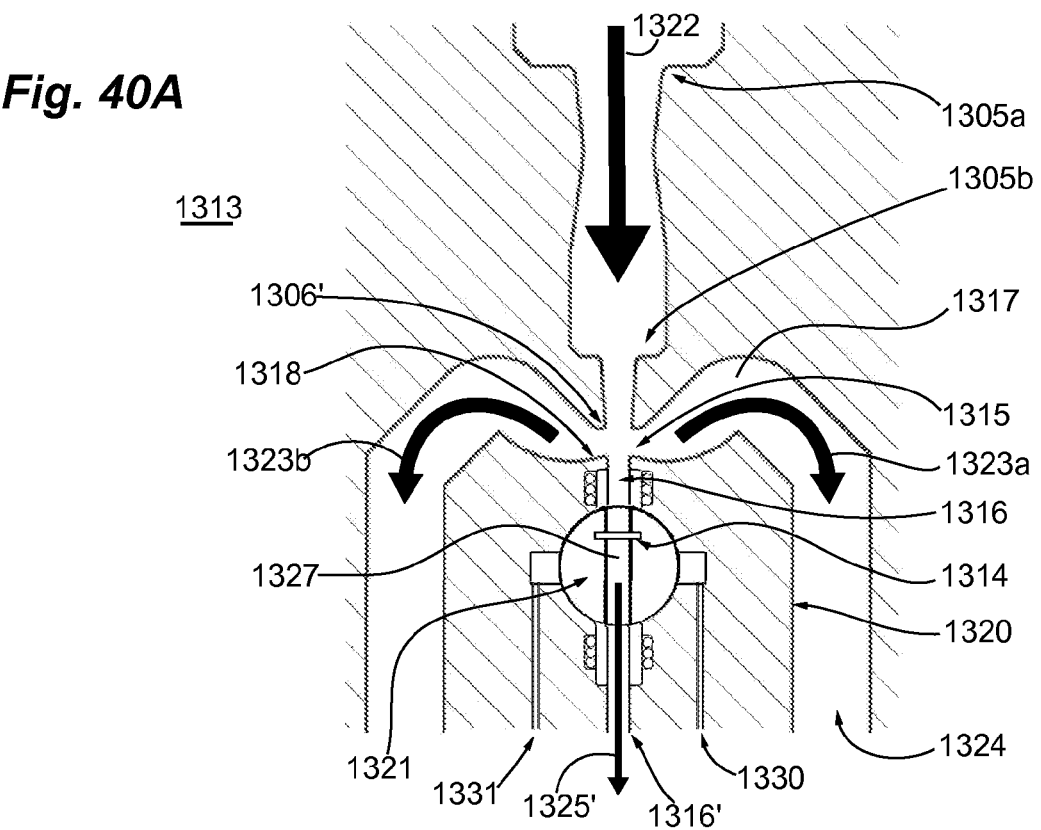
Figure 40B:
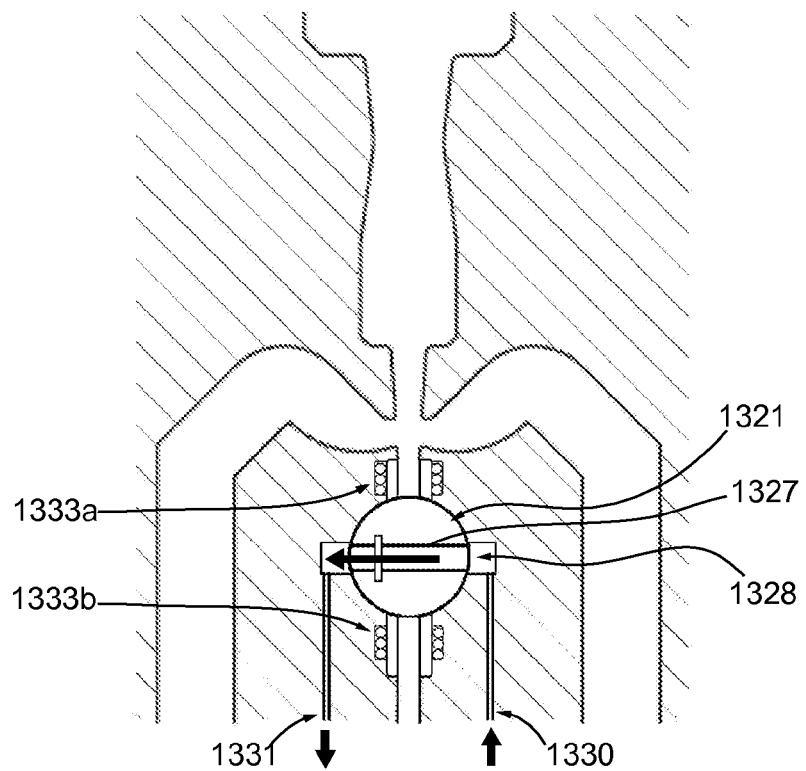

FIGS. 40A and 40B are cross-sectional views of a particle concentrator assembly 1313 with integrated particle trap 1314 (here shown as a single pervious sieve element) and air-to-air particle concentrator with aerodynamic lenses (1305*a,b*) and skimmer "tee" (1306'). Close proximity of the trap to the virtual impactor mouth 1315 is found to reduce deposition losses in the collector duct 1316.

Serendipitously, forming the lateral arms 1317 of the skimmer with a concavoconvex reverse turn (i.e., greater than 180 degrees) away from the long axis of flow through the skimmer nose 1318 as shown provides more lateral space in the skimmer body 1320 for a particle trap mounted in a stopcock-like rotatable cylinder body 1321 directly below the virtual impactor mouth. In these views, the particle trap is rotatable on an axis and may be turned from a position coaxial with the long axis of flow to a secondary position for desorption and analysis. The suction intake gas stream 1322 is split above the virtual impactor mouth 1315 into two arms of a bulk flow 1323*a/b* (which is diverted into the lateral flow channels 1324) and a particle ribbon flow 1325' (which is directed down the collector duct 1316 and through particle trap 1314, where it is harvested for particles before being exhausted at 1316').

Also occupying the skimmer body 1320 is an injection circuit or loop with inlet 1330 and outlet 1331. The injection circuit is a pneumatic (or hydraulic) injection channel or loop and interfaces with rotatable cylinder 1321 that houses the particle trap. In FIG. 40A, the cylinder is in a first position so that center passageway (termed the "trap hollow volume" 1327) is fluidly confluent with the long axis of the collector duct 1316; in FIG. 40B, the cylinder has been rotated 90 degrees to a second position and the trap hollow volume is oriented crosswise. In the second position, the trap hollow volume is confluent with injection ducts (1330, 1331) and the movement of an injectate through the trap hollow volume is shown as a black arrow. The injection duct is provided with a pump or suction for conveying the injectate to a detector in a small volume and is heated if necessary. Alternatively the injection circuit may convey any analyte recovered from the particle trap to a secondary focusing trap for further concentration.

The two views thus correspond to two steps of a sampling and analysis cycle. In a first, "normal" position, the trap hollow volume 1327 and particle trap 1314 are aligned with the long axis of the suction intake 1322 and are positioned to capture any particle concentrate in the intake flow for a defined period of time, for example one minute. In a second "orthogonal" position, the trap hollow volume is aligned crosswise to release constituent volatiles (or solutes) from the particle trap into the injection duct circuit within the skimmer body.

Advantageously, no separate valving is needed and, in both positions, flow is through the particle trap mesh, not crosswise over it. The particle "cut size" of the mesh or filter is generally about 5 microns. Reliable collection of particulates in the range of 5 to 100 microns is associated with a higher degree of detection sensitivity at a reasonable energy cost. The system has been shown to be operable at suction intake flow rates of 500 to 1500 sLpm, while not limited thereto, but the flow of particle concentrate through the particle trap is substantially less (as dictated by the flow split) and may be 5 to 15 sLpm or less, for illustration. The overall preconcentration factor on a volume basis can thus be about 750,000× or more. The preconcentration factor is equal to the total aspirated volume 1322 (which can be up to 1500 liters or more per minute) divided by the hollow trap volume 1327 of injectate plus any volume in the injection loop. For slit-type traps trap deadspace will be perhaps 1-3 milliliters, but for annular traps, sub-milliliter traps are readily achieved (see US Pat. Doc. No. 2010/0186524, which is coassigned).

The small volume realized by this construction achieves significant improvement in preconcentration over systems lacking an air-to-air particle concentrator. Since only a single particle of sufficient mass is required for detection, the lower limit of detection is the limit of the analytical detector itself per person, container, pallet, vehicle, and so on. Thus a limit of detection by mass spectrometry is conservatively 100 picograms or less per sample [Committee on Assessment of Security Technologies for Transportation, 2004, Mass Spectrometry for Trace Detection of Threat Agents, In, Opportunities to Improve Airport Passenger Screening with Mass Spectrometry. The National Academies Press, Washington, D.C., pp 15-28.] Importantly, reduction of interferents by selective stripping (either selectively stripping analytes of interest or selectively stripping interferents, such as by solvent elution or thermal ramping) may improve sensitivity by eliminating or reducing background signals.

In FIG. 40B, the particle mesh is shown to be mounted in a cylindrical stopcock or body 1321 and by turning the cylindrical body, the mesh is now aligned parallel to the long axis of flow in the collector duct, but in line with secondary injection ductwork for collecting volatiles (or an eluate). By heating the skimmer body and associated ducts (shown are heating elements 1333*a/b*), any particulate materials can be warmed in a very small volume of carrier gas to a temperature where they evaporate. Hot carrier gas (or liquid) can also be used to heat the particles convectively, as in a circulating closed loop. The warm gas mixture (or liquid) can then be conveyed, by positive pressure or by aspiration, directly or indirectly into a detection apparatus such as a mass spectrometer, or into a focusing trap.

Following desorption, the mesh can be returned to the first "normal" position and heated more aggressively to incinerate or char remaining particulate materials. The ash and residues can then be blown from the system, either with suction or more preferably by reversing the pump so as to blow the material out the front end of the apparatus. Optionally, the cylindrical body is a disposable cartridge and can be removed from the particle concentrator assembly for off-line analysis or archiving.

In one explosives detection system, the particle concentrator assembly 1335 may include a centrifugal impactor 1336 as shown in FIG. 41, skimmer assembly 1337, and aerodynamic lens elements (1338*a, b, c*). As shown here, the centrifugal impactor is integrated into the skimmer body. Various centrifugal impactors have been described in more detail in co-pending and co-assigned U.S. patent Ser. Nos. 12/833,665 and 12/364,672, which are incorporated herein in full by reference. Advantageously, aligning the lateral arms of the skimmer "tee" (1339) in a reverse concavoconvex curvature increases the space below the virtual impactor for positioning the sinusoidal bends 1340 of the centrifugal particle trap proximate to the virtual impactor mouth.

Particles are first concentrated as a particle beam in the focusing section of the particle concentrator (shown here as a series of three aerodynamic lens elements in an intake channel). The particle beam is then separated from the bulk flow where the channel bifurcates in the skimmer assembly 1337, (shown here with a virtual impactor mouth opening to a collector duct 1342 for receiving the particle beam or ribbon and with lateral channels 1343 for receiving the bulk flows 1344). Bulk flows exit the skimmer in channels disposed contralaterally around the central "tee" in section, the head of the tee forming the mouth of the virtual impactor. Bulk flow is driven by a suction blower disposed downsteam from the skimmer. The particle beam or ribbon enters the virtual impactor mouth and continues along collector duct 1342, shown here with conical intake section. The particle concentrate stream is then subjected to bending of gas streamlines so that particles inertially impact the walls of the particle trap (shown here as a double "U" 1340) in a curved section or loop of the trap, where they are captured. The dimensions and operational configuration of the particle trap determine the size of the particles that will be captured according to a Stoke's number. The particle trap exhaust 1345 is fluidly connected to a downstream suction pressure source. The particle-enriched flow 1346 is exhausted of larger particles in this way and may be discarded.

Figure 41:
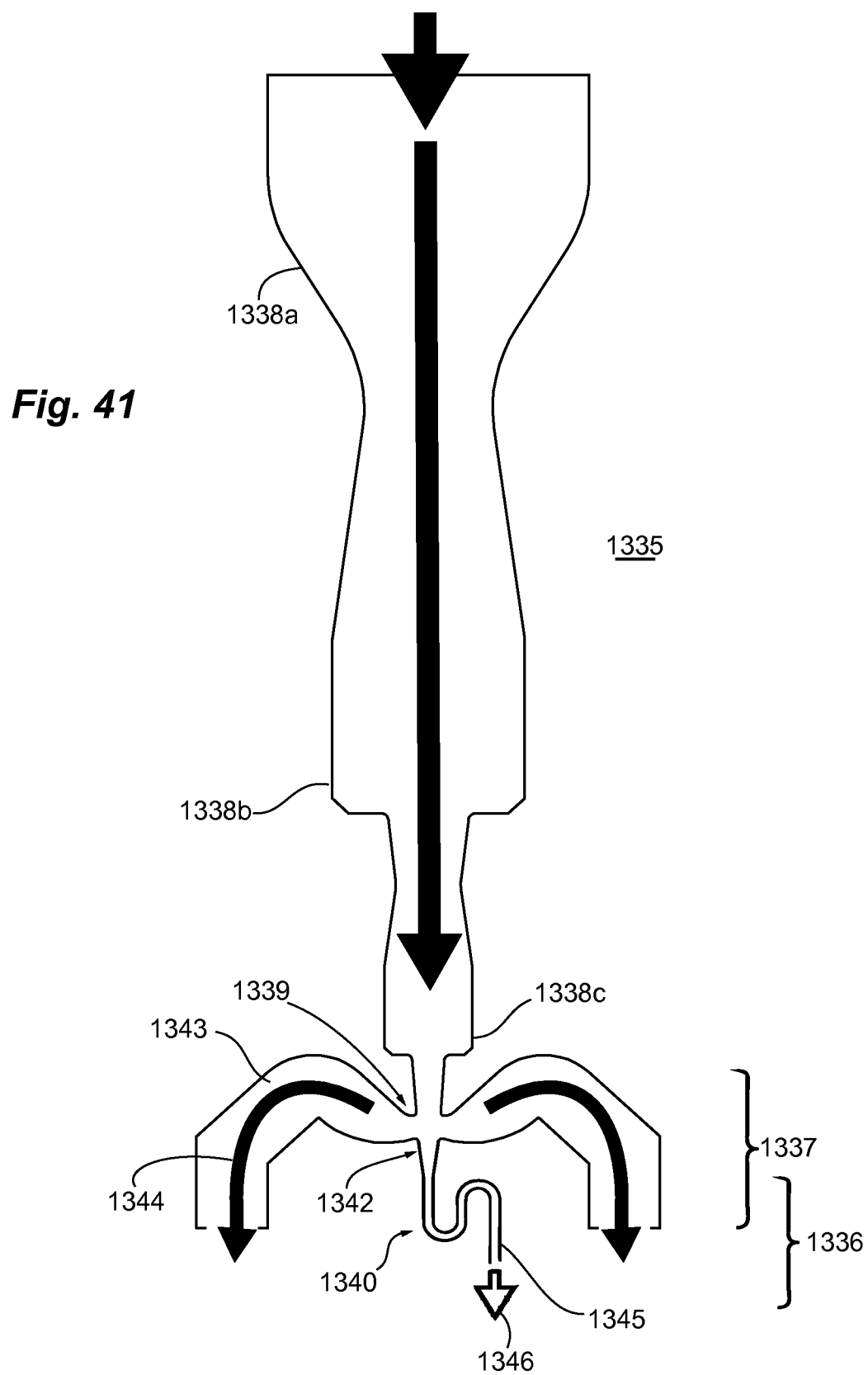

With suitable detectors, particulate material can be analyzed directly in the trap by spectrometric or pyrometric means. Or constituents that are stripped from the particle trap are conveyed to an analytic module for analysis. In a preferred system, the particle traps of FIGS. 40 and 41 can instead be sampled by injecting a small volume of solvent for liquid extraction. A liquid sample results. Liquid elution of particular analytes or classes of analytes may be accomplished using one or more chemically selective solvents. Selective elution can be advantageous in that insoluble interferences are left in the trap for subsequent incineration or purging, thus achieving not only preconcentration but also pre-purification. Ultrasound may be used to enhance elution and may also be used to clean fouled surfaces of the particle trap. Such liquid samples are compatible with liquid chromatography, including reverse phase and ion chromatography, and with electrospray mass spectroscopy, for example. The repertoire of liquid-based detection methods available are vast and are not reviewed here. Alternatively, a liquid sample may be vaporized for gas phase analysis or may be subjected to solid phase extraction in a focusing trap prior to analysis. Advantageously, solvents may be selected exclude insoluble materials such as minerals, ash, and hair but readily and selectively solubilize constituents of interest associated with the skin particles, hairs, dust, explosives crystals, and so forth. In our hands, acetonitrile has proved a useful solvent for elution of explosives, successfully eluting both RDX and TATP, for example. Dimethylformamide, tetrahydrofuran, butyrolactone, dimethylsulfoxide, n-methyl-pyrrolidinone, propylene carbonate, acetone, ethylacetate, methanol, water, and chloroform are also useful and may also be used to selectively remove interferences in some instances. Also useful are solvent mixtures and gradients thereof, as have been described by DL Williams and others.

A coating of carbon in the particle trap may be used to enhance capture of volatiles and vapors associated with the particle-enriched stream. While carbon has a very high affinity for many vapors, hot solvents are generally more effective in releasing adsorbed vapors than heat alone.

Figure 42A:
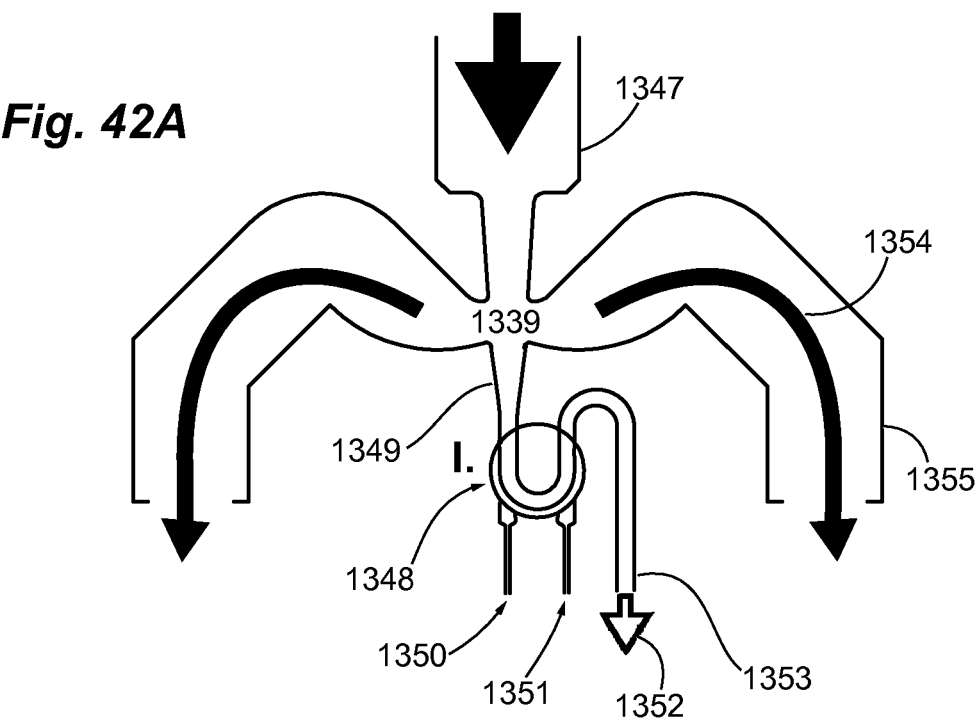

FIG. 42A illustrates a centrifugal particle trap integrated into a stopcock-like rotatable cylindrical body in the collector duct immediately downstream and proximate to a skimmer "tee" 1339 and ADL outlet 1347. At the high throughput of suction gas flow needed for effective surveillance, miniaturization of this sort is not possible with earlier technologies. Without a suitable flow split, as obtained by upstream air-to-air preconcentration of the particle beam or ribbon, an acceptably low pressure drop and velocity of the airstream transiting the particle trap would be impossible to achieve, resulting in particle losses. As shown in FIG. 42A, the cylindrical body 1348 is in a first position (I) fluidly confluent with the collector duct 1349 and in FIG. 42B in a second position (II, rotated 180 degrees) fluidly confluent with small bore inlet 1350 and outlet 1351 injector ducts that form an alternate pathway or loop for an elution solvent or for a hot carrier gas. The skimmer body and stopcock are optionally heatable on demand.

In FIG. 42A, a suction flow is established, bulk flow is diverted at skimmer tee 1339, and air bearing the informationally rich particle concentrate is introduced into the particle trap (first position, I). Particle-exhausted air 1352 exits the particle trap at 1353 and is discarded (or may be routed to a vapor trap if desired). Particles are trapped inertially in the curved "U" of the particle trap, the internal volume of which constitutes a "trap hollow volume". Bulk flows 1354 are drawn through lateral arms 1355 by a downstream suction blower.

Figure 42B:
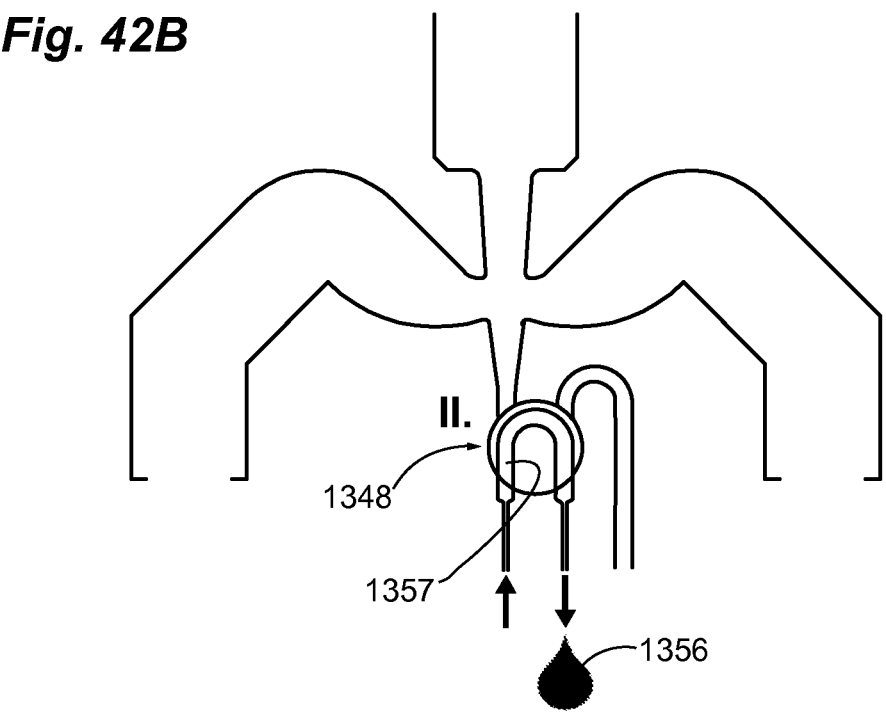

In FIG. 42B, the "stopcock" has been rotated 180 degrees so that the fluid path is now confluent with the sampling ducts. Suction flows are stopped for the duration of an analytical cycle, where constituents of any particle concentrate in the trap are analyzed. In this second position (II), elution solvent or hot carrier gas is injected through the particle trap and conveyed to an analytic instrument, to a focusing trap, or to a device for archiving or secondary processing. A highly concentrated liquid volume (or carrier gas volume) is generated 1356. Since the trap hollow volume 1357 of the rotating member 1348 is generally less than a milliliter, the overall preconcentration factor PF is minimally 5000× for a two second aspiration at 300 L/min, and 1,000,000× for a 60 sec aspiration at 1000 L/min (a one million-fold preconcentration by volume). In short, efficient aspiration of a single particle can result in a positive detection event.

In a fully integrated system, the system combines a jet-suction nose for drawing a suction flow, an air-to-air particle concentrator for separating a bulk flow from a particle-enriched flow, a particle trap with integrated mechanism in the skimmer nose for collecting explosives-associated residues, and valveless means for conveying captive volatiles or vapors from the particle trap to a detection means. Yet more compact systems with detection means for screening particulate residues incorporated in situ in the particle trap, such as described in WIPO Pat. Doc 2004/027386 and by spectrometric in situ detection, are also conceived.

Figure 43A:
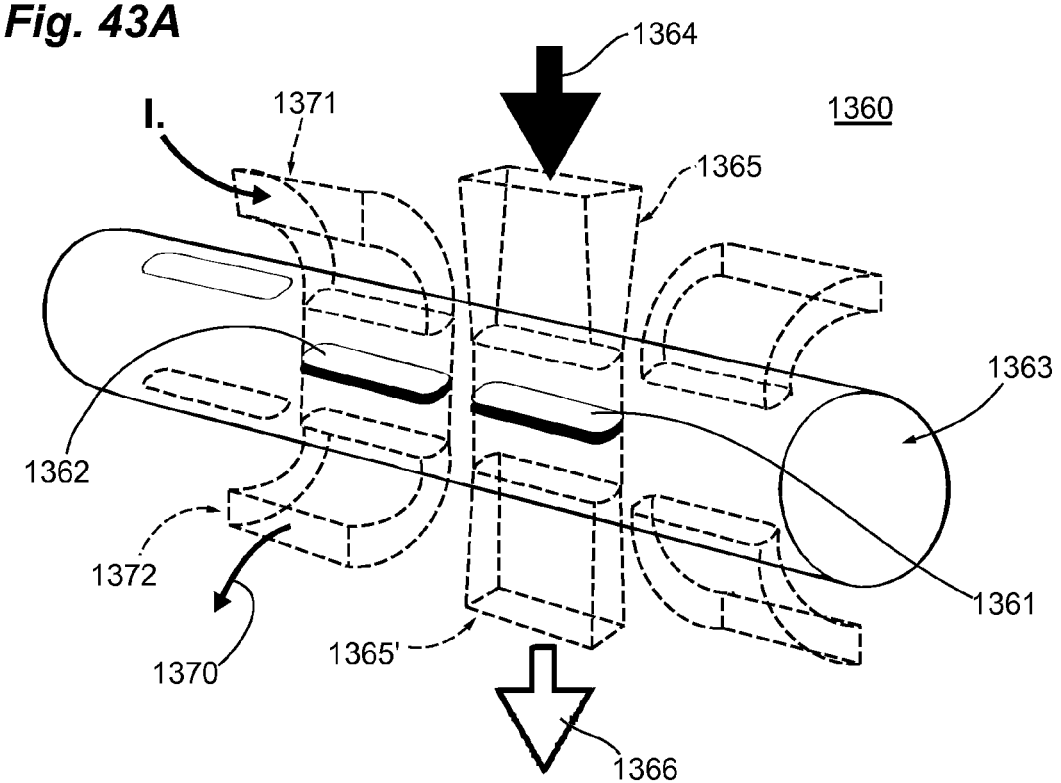
Figure 43B:
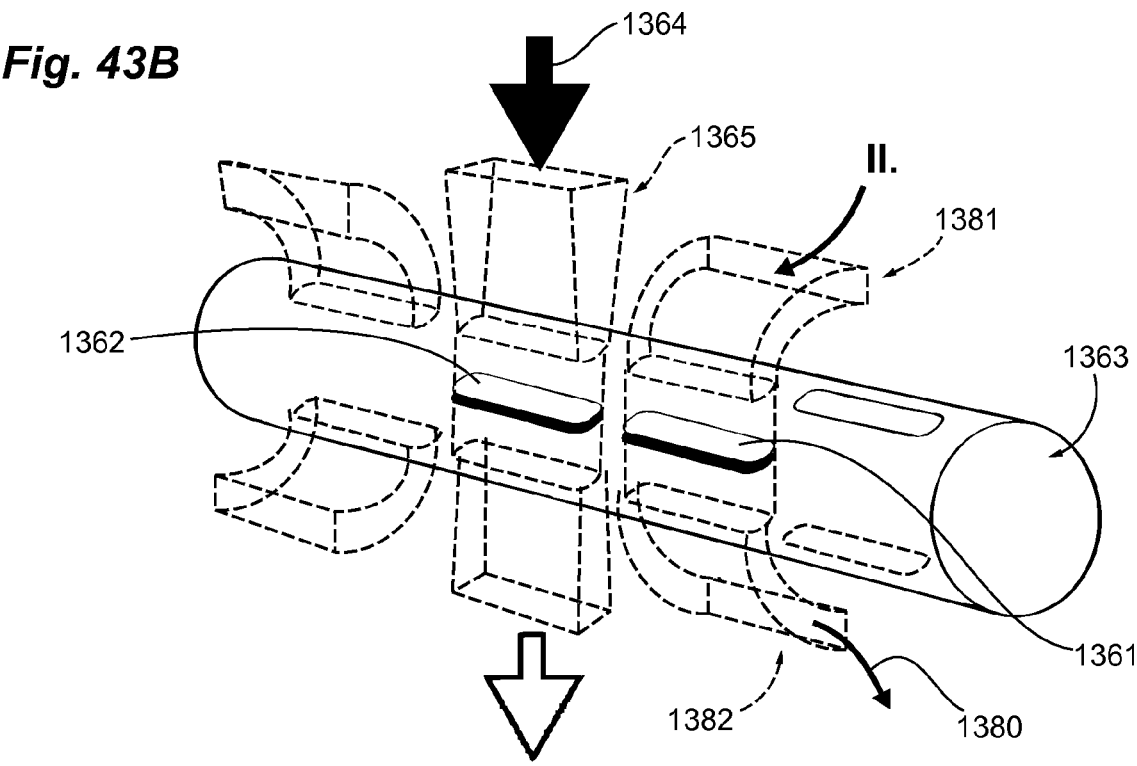

FIG. 43 depicts a second valveless system 1360 for eluting or thermally desorbing explosives-associated residues from a pair of particle traps (1361, 1362) disposed in a trap hollow volume within a reciprocating member 1363. For illustration, particle trap members in this device are sieve or mesh-type members that are generally rectangular in shape for receiving a particle-enriched ribbon from a slot-type virtual impactor via collector duct. Suction intake gas 1364 enters a collector duct 1365 at the top as a particle-rich flow and exits at the base of the collector duct 1365' as a particle-exhausted flow 1366; particles are trapped on one of the pervious filter elements (1361, 1362) in alternation, depending on the position of the reciprocating body. The reciprocating body has translational freedom to slide transversely between a first position (FIG. 43A) and a second position (FIG. 43B).

In FIG. 43A, the first particle trap 1361 is situated in line with the collector duct 1365 and the second particle trap 1362 is situated in fluid communication with an injector duct, the injector duct flow (black arrow, 1370) traversing inlet 1371 and outlet 1372. While the first particle trap is accumulating particles, the second particle trap is in analysis mode. Carrier gas or solvent (I) is injected at inlet 1371 through the particle trap and constituents of interest are conveyed from pervious member 1362 to a downstream analytic module.

In FIG. 43B, the stations are reversed: while the second particle trap is accumulating particles and suction 1364 is flowing, the first particle trap is in analysis mode. Carrier gas or solvent flow (black arrow, 1380) is injected (II) through a second injection duct with inlet 1381 and outlet 1382. The flow contacts pervious member 1361 and constituents of interest are conveyed to an analytic module. During this operation, the particle-enriched flow is directed through the second particle trap 1362 and more particles are accumulated.

The system is thus capable of essentially continuous operation by alternating collection and analysis modes between the two particle traps. Conditions during the dissolution or volatilization part of the cycle may be intensified so that stripping and regeneration of each trap is accomplished before the trap is returned to the collection station. As required, the body surrounding the trap and the cylindrical sliding body may be heated. When not in use, the injector pathways are blocked by the body of the reciprocating member, thus there are only two passages through the reciprocating body, each constituting a trap hollow volume. This feature eliminates the need for supplementary valving. Not shown is a cavity in the sampling head for receiving the reciprocating member. O-rings, gaskets, and registration features as would be useful in operation of the device are well known and are not shown for simplicity of illustration.

Figure 44:
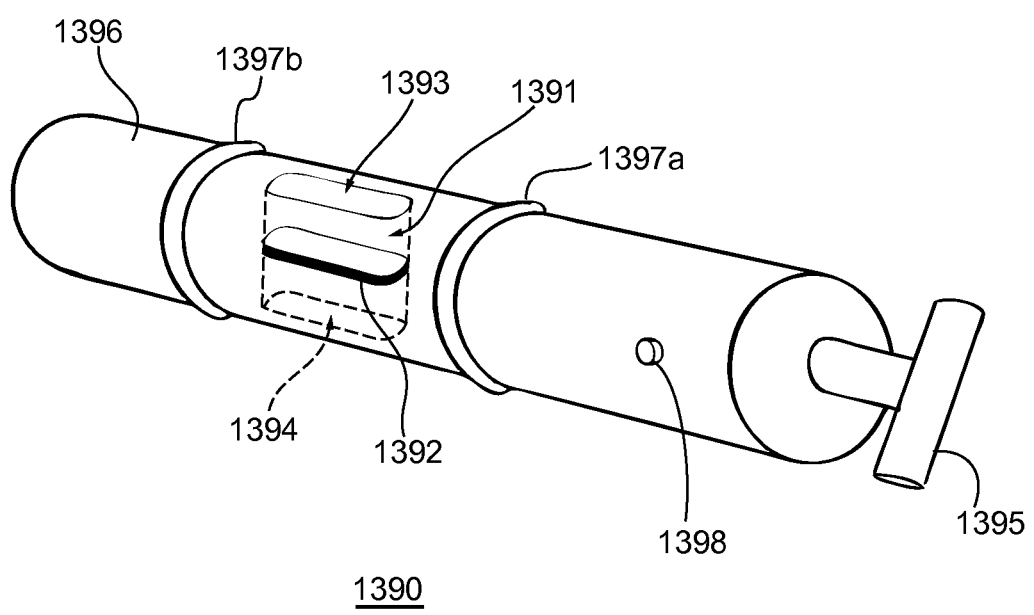

FIG. 44 illustrates a cartridge body 1390 formed with a single passageway or "trap hollow volume" 1391 with particle trap 1392 disposed therein. The particle trap is depicted as a pervious filter member in a channel through the cartridge body, the channel with inlet 1393 and outlet 1394 for aligning with a collector duct of a skimmer body. The cartridge body is adapted to be sealably inserted into a receiving cavity of a sampling head and includes a handle 1395 for easy removal. The walls 1396 of the cartridge body are adapted with seals 1397*a,b* and a key pin 1398 so that the cartridge may be inserted and locked in place in a cartridge receiving cavity of the sampling head, the trap hollow volume aligning itself to be sealed and fluidly confluent with the collector duct of a skimmer (as depicted previously) so that a particle-enriched gas stream must pass through the pervious filter member during particle concentration and collection. Cartridge bodies of this type may be periodically replaced so that the used cartridge with any accumulated particles may be handled off-line and inserted into a specialized sample receiving vessel of an analytical instrument for detailed analysis of particle constituents.

Figure 45:
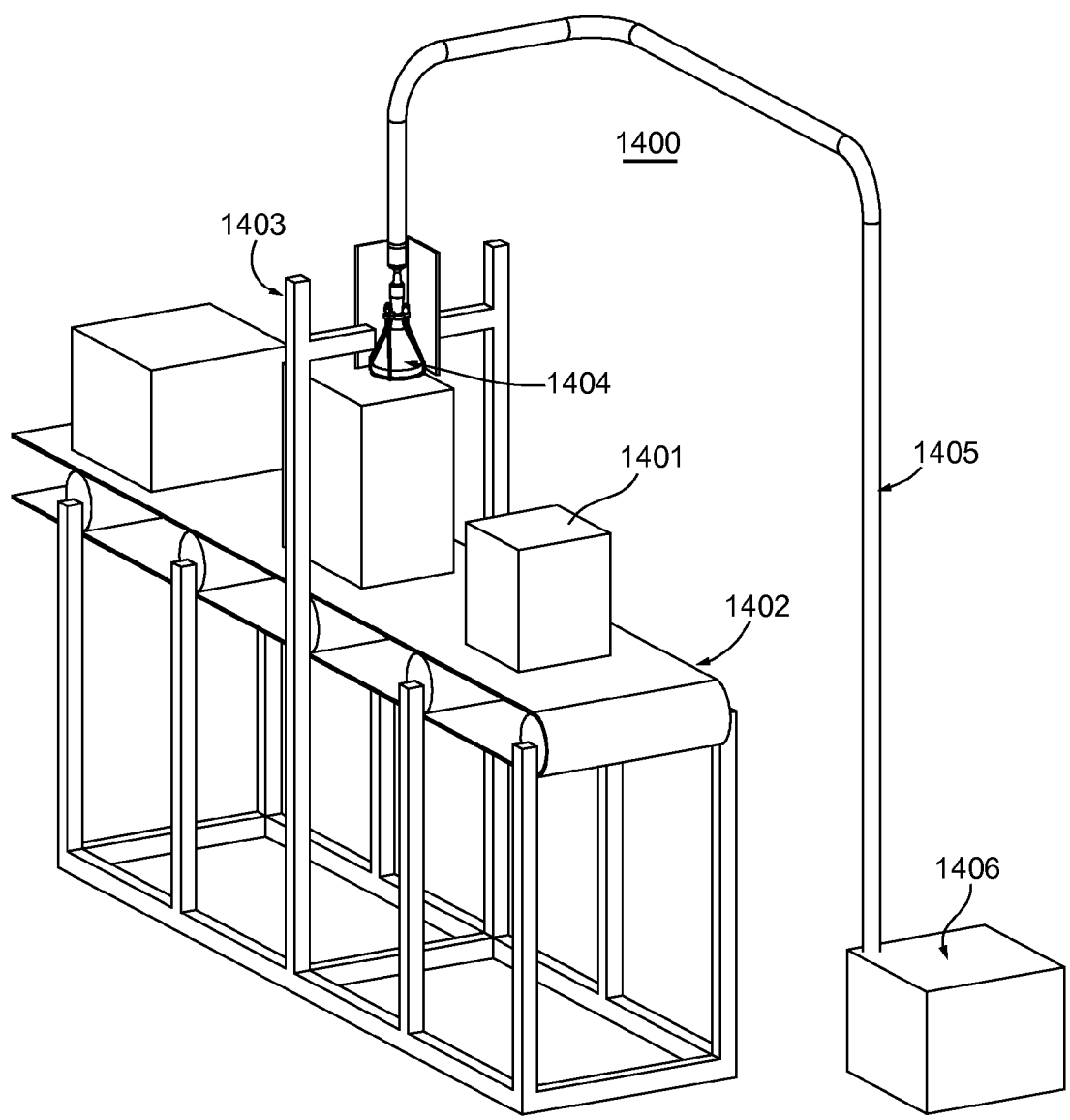
FIG. 45 pictorially depicts implementation of a sampling device for automated inspection of parcels.

FIG. 45 is a schematic view depicting implementation of a sampling apparatus 1400 for automated inspection of parcels. Parcels 1401 advancing on a conveyor belt 1402 pass under or through a supporting frame 1403, here shown configured with a single sampler head 1404. The sampler head is configured for emitting a train of jet pulses at high velocity against the packages from a distance of up to about 30 cm, so that particle and vapor residues associated with external and internal surfaces the parcels are mobilized. A suction intake is operated simultaneously to aspirate any particles eroded from the parcel surfaces by the action of the jets. Power and any positive and negative air pressures are supplied via an umbilicus 1405 from remote support module or cart 1406. Analysis may be performed within the sampler head or remotely. Multiple sampler heads may be used to inspect multiple faces of the baggage stream. Similarly, a portal with passageway for surveilling persons may be constructed.

FIG. 46 is a schematic view depicting deployment of a sampling apparatus with sampler head array for inspection of vehicles. Vehicles 1411 advance through an overhead frame 1412 fitted with multiple sampler heads 1413 of the invention. The sampler heads 1413 focus a pattern of jet pulses on the exterior surfaces of the vehicle to aerosolize any residues deposited thereon and aspirate any aerosols that are generated. Power and positive and negative air pressures are supplied via an umbilicus 1414 from remote utilities and control module 1415. Each sampler head is generally configured to trap particles within the head. Analysis may be performed within the sampler head or remotely, optionally with evaporative collection of volatiles for conveyance to a central analytic module in heated lines. Preliminary detection is preferred, where a detection means is incorporated in the individual detection head. Cartridges requiring more detailed analysis may be removed from the sampling head(s) and analyzed at a remote workstation. Cyclical regeneration of the trap(s) between each vehicle inspected, typically by reversing the air flows, may be necessary to avoid fouling of the particle traps. Incineration and ultrasound may also be used to keep particle traps clear in the presence of large amounts of road dust. Use of ultrasound is described in one or more of our co-pending applications.

A number of methods may be used to augment the capacity of the sampler head to strip off particles from substrates. One such technique is a jet gas feed ionized by contact with a source of ions, such sources including but not limited to a "corona wire," a source of ionizing radiation, a glow discharge ionization source, or a radio-frequency discharge. The ionized gas stream is used to neutralize electrostatic associations of particles with surfaces and improve lift off of particles.

Collisions of higher molecular weight gas atoms or molecules results in improved desorption of residues. The carrier is typically air, argon or nitrogen and the gas or solvent is a high molecular weight molecule sufficient to aid in dissociation of particles and volatile residues from the object or environmental surface of interest. Pressurized gas tanks eliminate the need for an on-board compressor, thus reducing power requirements for portable applications. The presence of organic vapors also can aid in volatilizing chemical residues such as explosives and will compete with organic molecules for binding to solid substrates. Heated jet pulses or infrared lamps directed from the sampling head have been proposed by others for improving sampling efficiency for vapors, however, it should be recognized that premature heating can reduce particle collection efficiency. Near sonic jet pulses are preferable to hot air for aerosolizing particles from substrates.

Hot solvent also increases the specific heat capacity of a hot carrier gas stream and can improve convective heating of sorbent beds, aiding in desorption of constituents of interest and in cleardown.

Example

In one study, 20 nanograms of TNT trace explosive was deposited on a glass surface using a dry transfer technique from a Teflon® Bytek strip and interrogated with a surface sampler of the invention. The dry transfer technique was performed essentially as described by Chamberlain (U.S. Pat. No. 6,470,730). Particle size distribution (crystal size distribution) was about 10-200 microns. The apparatus was operated with a 3 mm jet array at 80 psig back pressure. The dislodged TNT particles were aspirated at a 1000 sLpm flow rate into a high flow air-to-air particle concentrator with aerodynamic lenses and skimmer and captured in a particle trap formed of a 13 mm pervious member. Explosives constituents of captive particles were dissolved by injection of 100 μL of acetonitrile, of which 10 μL was injected into an IMS detector. A measurable TNT signal was observed. The experiment demonstrates detection of trace explosive residues at a nanogram detection level using a jet-assisted non-contact sampling head of the invention.

While the above is a complete description of selected embodiments of the present invention, it is possible to practice the invention use various alternatives, modifications, combinations and equivalents. All of the U.S. patents, U.S. patent application publications, U.S. patent applications, foreign patents, foreign patent applications and non-patent publications referred to in this specification are incorporated herein by reference in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. An apparatus for sampling and concentrating a trace residue of an explosive or explosive-associated material from an object, structure, surface, cavity, vehicle or person, which comprises:
   a) a sampler head with directional nose, said nose having an intake port and upstream channel for receiving a first sample as a suction gas flow having a volume and a velocity and for conveying said suction gas flow to an air-to-air particle concentrator, said air-to-air particle concentrator for accelerating and inertially dividing said suction gas flow according to a flow split into a particle-enriched flow in a first downstream channel and a bulk flow in a second downstream channel;
   b) a particle trap with trap hollow volume disposed in said first downstream channel, said particle trap for immobilizingly accumulating particles from said particle-enriched flow in said trap hollow volume;
   c) a means for stripping any constituent or constituents of said accumulated particles from said trap hollow volume of said particle trap in a carrier volume; and
   d) a means for analyzing said carrier volume to detect a trace residue of an explosive or explosive-associated material.

2. The apparatus of claim 1, wherein said air-to-air particle concentrator is characterized as a combination of an aerodynamic lens and a skimmer, said skimmer having a lateral flow channel for receiving said bulk flow into said second downstream channel, a virtual impactor mouth for receiving said particle-enriched flow into said first downstream channel, a skimmer body with a skimmer nose and a collector duct, wherein said collector duct fluidly conjoins said virtual impactor mouth and said first downstream channel, and said particle trap with trap hollow volume is disposed in said collector duct.

3. The apparatus of claim 1, wherein said particle trap is a centrifugal impactor.

4. The apparatus of claim 1, wherein said particle trap is a pervious screen, and wherein said pervious screen is selected from a ceramic filter or mesh, a glass filter or mesh, a plastic filter or mesh, or a metal filter or mesh.

5. The apparatus of claim 2, wherein said skimmer body comprises a cartridge body receiving chamber for receiving an insertably removable cartridge body, said removable cartridge body with said trap hollow volume disposed therein, and wherein said trap hollow volume of said cartridge body is configured for sealedly aligning with said collector duct during suction gas flow, and further wherein said removable cartridge body receiving chamber is coaxially disposed in said collector duct or transversely disposed across said collector duct.

6. The apparatus of claim 5, wherein said removable cartridge is coaxially disposed in said collector duct and comprises a skimmer body nose.

7. The apparatus of claim 2, wherein said skimmer body comprises a cylindrical body transversely disposed across said collector duct, said cylindrical body having a long axis orthogonal to said collector duct and said trap hollow volume disposed therein, said cylindrical body further having a first rotational position wherein said trap hollow volume is confluently aligned with said collector duct and a second rotational position wherein said trap hollow volume is confluently aligned with an injector duct, said injector duct with inlet and outlet, and said trap hollow volume of said cylindrical body rotates therewith for valvelessly cycling between said first rotational position for collecting particles in said particle trap and said second rotational position for stripping said particle constituent or constituents from said trap hollow volume.

8. The apparatus of claim 2, wherein said skimmer body comprises a slideable crosswise body transecting said collector duct, said slideable crosswise body having a long axis orthogonal to said collector duct and a particle trap with trap hollow volume disposed therein, said crosswise body further having a first transverse position wherein said trap hollow volume passageway is confluently aligned with said collector duct and a second transverse position wherein said trap hollow volume is confluently aligned with an injector duct inlet and outlet, and wherein said trap hollow volume slides with said cylindrical body and is slideably positioned therewith for valvelessly cycling between said first transverse position for collecting particles in said particle trap and said second transverse position for stripping said particle constituent or constituents from said trap hollow volume.

9. The apparatus of claim 8, wherein said slideable crosswise body comprises a second trap hollow volume therethrough, said second trap hollow volume having a first transverse position wherein said second passageway is confluently aligned with said collector duct and a second transverse position wherein said second passageway is confluently aligned with an injector duct inlet and outlet, and further wherein said first passageway and said second passageway are configured for reciprocally collecting and stripping a first sample and a second sample in alternation.

10. The apparatus of claim 2, wherein said means for stripping comprises heating said skimmer body, injecting a carrier gas, a solvent, or a mixture of a carrier gas and a solvent into said trap hollow volume, or a combination thereof.

11. The apparatus of claim 1, wherein said means for stripping said particle constituent or constituents comprises a means selected from:
   a) means for introducing a volume of a hot carrier gas into said particle trap and conveying any volatiles released therefrom to an analytic module for analysis;
   b) means for directing an infrared emission, a microwave emission, or a laser emission at said particle in said particle trap and conveying any volatiles released thereby to an analytic module for analysis;

c) means for resistively heating said particle trap and conveying any volatiles released therefrom to an analytic module for analysis;

d) means for injecting a solvent and conveying any solutes released therein to an analytic module for analysis;

e) means for sensing a particle constituent in situ in said particle trap and stripping said constituent thereafter; or f) a combination of one or more of the above means.

12. The apparatus of claim 1, wherein said means for analyzing is selected from a) means for performing a liquid chromatographic step; b) means for performing a gas chromatographic step; c) means for performing an affinity binding step; d) means for performing an ionization step; e) means for performing an electrophoretic step; f) means for performing a spectrometric, fluorometric, or photometric step; g) means for performing a mass spectroscopic step; h) means for performing an electron capture step; i) a combination of one or more of the above means; or j) other analysis and detection means known in the art.

13. The apparatus of claim 1, further comprising an array of two or more gas jet nozzles disposed pericentrally on said nose, wherein said jet nozzles are configured for emitting a jet pulse or train of jet pulses at a nozzle velocity of greater than Mach 0.5, said jet pulses for mobilizing and eroding residues on a surface impacted thereby; further wherein said jet pulses have a pulse width of less than 100 milliseconds, more preferably less than 10 milliseconds, and a stagnation distance of greater than 10 inches; said jet nozzles are directional jet nozzles; and optionally wherein said sampler head comprises at least one interchangeable head attachment.

14. A method for sampling trace residues from an object, structure, surface, cavity, vehicle or person to detect a threat, which comprises:

a) aspirating a first sample with a volume and a velocity into a suction intake of a sampling head and conveying said volume as a suction gas flow through an upstream channel, said volume containing particles and free vapors;

b) inertially dividing said suction gas flow into a particle-enriched gas flow containing a particle concentrate and a bulk gas flow containing the bulk of said free vapors, and directing, according to a flow split, said particle-enriched gas flow to a first downstream channel and said bulk flow to a second downstream channel, wherein said first downstream channel and said second downstream channel bifurcate from said upstream channel;

c) immobilizingly accumulating said particles for a time in a particle trap disposed in said first downstream channel; and d) analyzing any constituents of said accumulated particles to detect a threat indicated by detection of an explosive or explosive-associated residue therein.

15. The method of claim 14, wherein said step for analyzing comprises stripping said particle constituents in said particle trap in a liquid carrier volume.

16. The method of claim 14, wherein said step for analyzing comprises stripping said particle constituents in a gas carrier volume.

17. The method of claim 14, further comprising a step for cleardown wherein said particle trap is regenerated or replaced without disassembly before receiving a second sample.

18. The method of claim 14, further comprising mobilizing and aerosolizing said particles and said free vapors by impacting said object, structure, surface, cavity, vehicle or person with a jet pulse or pulse train directionally emitted from said sampling head, and optionally wherein said jet pulse or pulse train and suction gas stream form a virtual sampling chamber.

19. The method of claim 14, wherein said flow split and said velocity are configured to reduce elutriative losses of particles having an apparent aerodynamic diameter of 5 to 200 microns in said suction intake and wherein said flow split is generally greater than 100:1, said particles being informationally rich, and further wherein said bulk flow is discharged to atmosphere without analysis.

20. An apparatus for sampling and concentrating a trace residue of an explosive or explosive-associated material from an object, structure, surface, cavity, vehicle or person, which comprises:

a) a sampler head with directional nose, said nose having an intake port and upstream channel for receiving a first sample as a suction gas flow having a volume and a velocity and for conveying said suction gas flow to an air-to-air particle concentrator, said air-to-air particle concentrator for accelerating and inertially dividing said suction gas flow according to a flow split into a particle-enriched flow in a first downstream channel and a bulk flow in a second downstream channel;

b) a particle trap disposed in said first downstream channel for immobilizingly accumulating particles from said particle-enriched flow, said particle trap having a hollow trap volume;

c) a means for analyzing a constituent or constituents of said accumulated particles in said particle trap; wherein said means for analyzing is an in situ detection means, a hydraulically coupled detection means, a pneumatically coupled detection means, or a remote detection means: and d) a means for stripping a constituent or constituents of said accumulated particles from said particle trap in a carrier volume.

* * * * *